US005747352A

United States Patent [19]
Yan et al.

[11] Patent Number: 5,747,352
[45] Date of Patent: May 5, 1998

[54] REAGENTS AND METHODS FOR THE RAPID AND QUANTITATIVE ASSAY OF PHARMACOLOGICAL AGENTS

[75] Inventors: Cheng F. Yan, Irvine; Chan S. Oh, Chino Hills; Anthony K. Cheng, Anaheim, all of Calif.

[73] Assignee: Beckman Instruments, Inc., Fullerton, Calif.

[21] Appl. No.: 248,479

[22] Filed: May 23, 1994

[51] Int. Cl.$^6$ .................................................. G01N 33/547
[52] U.S. Cl. .......................... 436/533; 436/805; 436/815; 436/816
[58] Field of Search ................................. 436/533, 805, 436/815, 816

[56] References Cited

U.S. PATENT DOCUMENTS

| | | | |
|---|---|---|---|
| 3,935,074 | 1/1976 | Rubenstein et al. | 435/7.9 |
| 4,067,774 | 1/1978 | Rubenstein et al. | 435/7.9 |
| 4,130,462 | 12/1978 | Rubenstein et al. | 435/7.9 |
| 4,134,792 | 1/1979 | Boguslaski et al. | 435/4 |
| 4,228,237 | 10/1980 | Hevey et al. | 435/7 |
| 4,238,565 | 12/1980 | Hornby et al. | 435/7.7 |
| 4,243,749 | 1/1981 | Sadeh et al. | 435/7 |
| 4,298,685 | 11/1981 | Parikh et al. | 435/7.5 |
| 4,506,009 | 3/1985 | Lenhoff et al. | 435/7 |
| 4,550,075 | 10/1985 | Bacquet et al. | 435/7.5 |
| 4,582,789 | 4/1986 | Sheldon, III et al. | 435/6 |
| 4,582,810 | 4/1986 | Rosenstein | 436/528 |
| 4,604,365 | 8/1986 | O'Neill et al. | 436/528 |
| 4,608,336 | 8/1986 | Benovic et al. | 435/7.7 |
| 4,687,732 | 8/1987 | Ward et al. | 435/6 |
| 4,711,955 | 12/1987 | Ward et al. | 536/29 |
| 4,722,906 | 2/1988 | Guire | 436/501 |
| 4,760,142 | 7/1988 | Primes et al. | 544/287 |
| 4,791,067 | 12/1988 | Sheiman et al. | 436/513 |
| 4,868,104 | 9/1989 | Kurn et al. | 435/6 |
| 5,103,021 | 4/1992 | Khanna | 548/542 |
| 5,132,242 | 7/1992 | Cheung . | |
| 5,168,057 | 12/1992 | Oh et al. | 435/174 |
| 5,180,828 | 1/1993 | Ghazarossian et al. . | |
| 5,196,351 | 3/1993 | Harris et al. | 436/501 |
| 5,374,516 | 12/1994 | Sutton et al. | 436/531 |

FOREIGN PATENT DOCUMENTS

| | | |
|---|---|---|
| 0 177 191 A1 | 4/1986 | European Pat. Off. . |
| 0 183 901 A3 | 6/1986 | European Pat. Off. . |
| 0 203238 A1 | 12/1986 | European Pat. Off. . |
| 0 220 899 A1 | 5/1987 | European Pat. Off. . |
| 0 310 361 A2 | 9/1988 | European Pat. Off. . |
| 0 315 317 A2 | 5/1989 | European Pat. Off. . |
| 0 315 317 A3 | 5/1989 | European Pat. Off. . |
| 0 315 317 B1 | 5/1989 | European Pat. Off. . |
| 0 344 578 A1 | 5/1989 | European Pat. Off. . |
| 0 405 578 A3 | 6/1990 | European Pat. Off. . |
| 0 451 810 A1 | 4/1991 | European Pat. Off. . |
| 2 029 011 | 3/1980 | United Kingdom . |
| 2 084 317 | 4/1982 | United Kingdom . |
| WO 87/04794 | 8/1987 | WIPO . |
| WO91/19980 | 12/1991 | WIPO . |

OTHER PUBLICATIONS

Baugh, L.D. et al., "Evaluation of Immunoassay Methods for the Screening of Cocaine Metabolites in Urine," J. Forens. Sci. 36:79–85 (1991).

Cone, E.J. et al.,"Validity Testing of Commercial Urine Cocaine Metabolite Assays: IV Evaluation of the EMIT® D.A.U.™ Cocaine Metabolite Assay in a Quantitative Mode for Detection of Cocaine Metabolite," J. Forens. Sci. 35:786–791 (1990).

Damien, J.M. et al., "Amikacin Assay: Correlation Between Rapid Bioassay Enzyme Immuno–Assay (EMIT) and Fluoro–Immuno–Assay (FIA)," Ann. Biol. Clin. 42:217–220 (1984).

Edinboro, L.E. et al., "Determination of Serum Acetaminophen in Emergency Toxicology: Evaluation of New Methods: Abbott TDx and Second Derivative Ultraviolet Spectrophotometry," Clin. Toxicol. 29(2):241–255 (1991).

Fytche, L.M. et al., Ion Mobility Spectrometry of Drugs of Abuse in Customers Scenarios: Concentration J. Forens. Sci. 37(6):1550–1566 (1992).

Lee, D.H. et al., "Does Amerlite Chemoluminescence Immunoassay (CIA) for Digoxin Have Lesser Positive Bias Than TDX Fluorescene Polarization Immunoassay (FPIA)," Clin. Chem. 36(6):1121 (1990). Abstract only.

Schwartz, J.G. et al., "Accuracy of Common Drug Screen Tests," Amer. J. Emerg. Med., 9(2):166–170 (1991).

Standefer, J.C. et al., "Drug Screening with EMIT Reagents: A Quantitative Approach to Quality Control," Clin. Chem. 37(5):733–738 (1991).

Ujhelyi, M.R. et al., "Free Digoxin Concentrations Using Three Immunoassay Methods in Patients Receiving Digoxin FAB Antibodies (FAB)," Clin. Parmacol, Therap. 49(2):131 (1991), Abstract only.

Wernly, P. et al., "Drug of Abuse Confirmation in Human Urine Using Stepwise Solid–Phase Extraction and Micellar Electrokinetic Capillary Chromatography," Anal. Chem. 64(18):2155–2159 (1992).

Bailey, D.N. et al., "Plasma Cocaethylene Concentrations in Patients Treated in the Emergency Room or Trauma Unit," Amer. J. Clin. Pathol. 99:123–127 (1993).

Bartolone, J.B. et al., "Immunochemical Analysis of Acetaminophen Covalent Binding to Proteins," Biochem. Pharamcol. 37(24):4763–4774 (1988).

(List continued on next page.)

Primary Examiner—Mary E. Ceperley
Attorney, Agent, or Firm—William H. May; Gary T. Hampson; Margaret A. Kivinski

[57] ABSTRACT

Bidentate reagents for rapidly and quantitatively assaying the concentration of pharmacological agents in biological samples are described. The reagents are used in an immunoassay format for determining the concentration of desired, preselected pharmacological agents, such as benzoylecgonine, cocaine, an opiate, PCP, digoxigenin, acetaminophen, carbamazepine, phenytoin, primidone, theophylline, an aminoglycoside antibiotic, vancomycin, quinidine or a cannabinoid.

25 Claims, 13 Drawing Sheets

OTHER PUBLICATIONS

Campbell, R.S. et al., "Experience With an Homogeneous Immunoassay for Paracetamol Acetaminophen," *J. Clin. Chem. Clin. Biochem.* 24:155–159 (1986).

Frowe, D.J. et al., "The Clinical Use and Measurement of Theophylline," *Ann. Clin. Biochem.* 25:4–26 (1988).

Helper, B. et al., "Homogeneous Enzyme Immunoassay of Acetaminophen in Serum," *Amer. J. Clin. Pathol.* 81(5):602–610 (1984).

Hill, M., "Evaluation of an Office Method of Measuring T–heophylline Serum Concentration," *J. Allergy Clin. Immunol.* 82:30–34 (1988).

Klotz, U., "Comparison of Theophylline Blood Levels Measured by the Standard TDx Assay and a New Patient–side Immunoassay Cartridge System," *Ther. Drug. Monitor.* 15:462–464 (1993).

Koizumi, F. et al., "Plasma Paracetamol Concentrations Measured by Fluorescence Polarization Immunoassay and Gastric Emptying Time," *Tohoku J. Exper. Med.* 155:159–164 (1988).

Mak, A. et al., "Technicon® Digoxin Assay: A Fully Automated Enzyme Immunoassay for the Detection of Digoxin in Human Serum," *Clin. Chem.* 36(6):1103 (1990). Abstract only.

Okurodudu, A.O. et al., "Evaluation of the Abbott TDx/FLx for Therapeutic Drugs and Quantitative Toxicological Assays," *Clin. Chem.* 38(6):1040 (1992). Abstract only.

O'Leary, T.D. et al., "Improvement in a Radioimmunoassay for Digoxin", *Clin. Chem.* 25(2):332–334 (1979).

Roberts, D.W. et al., "A Sensitive Immunochemical Assay for Acetaminophen–Protein Adducts," *J. Parmacol, Exper. Therap.* 241(2):527–533 (1987).

Rosenberg, N.M. et al., "Occult Cocaine Exposure in children," *Amer. J. Dis. Child.* 145:143. (1991).

Welch, C. et al., "Stratus® II Immunoassay System Evaluated for Analysis of Theophylline and Digoxin," *Clin. Chem.* 36(6):1187 (1990). Abstract only.

Wong, S.H.Y. et al., "Performance of Urinary Benzoylecgonine and Barbiturates Screening by a Rapid Visual Immunoassay," *Clin. Chem.* 38(6):996 (1992). Abstract only.

Brigati, et al. "Detection of Viral Genomes in Cultured Cells . . .", *Virology* 126:32–50 (1983).

Perelson, A.S., "Receptor Clustering on a Cell Surface", *Mathematical Biosciences* 49:887–110 (1980).

Sternberg, James C., "Rate Nephelometry", *Manual of Clinical Laboratory Immunology*, American Society of Microbiology, (1986).

Ashihara, et al. "Homogeneous Enzyme Immunoassay for Macromolecular Antigens . . . ", *Journal of Clinical Laboratory Analysis*, 1:80–82 (1987).

Nardelli, Bernardetta et al., "Polyacrylamide–streptavidin: a novel reagent for simplified construction . . . ", Journal of Immunological Methods, 120:233–239 (1989).

Green, N.M. et al., "The Use of Bifunctional Biotinyl Compunds . . . ", *Biochem. J.* 125, 781–791 (1971).

Davis, Bernard et al., "Microbiology", 3d Ed. pp. 292–295, 298–317, 324–327, 354–355.

Bush, M.E. et al., "Antigen Recognition and the Immune Response . . . ", *J. Esp. Med.* 136:1478–1483 (1972).

"Electron Microscopy of Complexes Between IgA (MOPC 315) and a Bifunctional Hapten", *Journal of Molecular Biology*, 56, 203–206 (1971).

Woods, V. et al., "The Capacity of Bifunctional Antigens . . . ", Immunochemistry 12, 379–382 (1975).

Oh, C. et al., "Nephelometric Inhibition Immunoassay for Small Molecules", pp. 457–476 (1988).

Tang, S.C. et al., "Chromium (III) azidoaquo complexes . . . " *Chem. Abs.*, Section 78—Inorganic Chem. 77:147107p(1992).

Larsson et al., "Affinity Precipitation of Enzymes", *Elsevier/ North–Hollard Biomedical Press*, 98(2), 330–338 (1979).

Lee, et al. "Synthesis of the Bifunctional Dinucleotide AMP–ATP and its Application in General Liand Affinity Chromatography", J. Solid Phase Biochem. 2(1), 31–39 (1977).

Flygare et al., "Affinity Precipitation of Dehydrogenases", *Anal. Biochem.* 133, 409–416 (1983).

Gibbons et al., "Homogeneous Enzyme Immunoassay for Proteins Employing B–Galactosidase", *Anal. Biochem.*, 102, 167–170 (1980).

Morris, et al., "Flavin Adenine Dinucleotide as a Label in Homogenous Colorimetric Immunoassays", *Anal. Chem.*, 53(4), 658–665 (1981).

Ngo, et al. "Enzyme Modulators as Tools for the Development of Homogeneous Enzyme Immunoassays", Elsevier/ North–Holland Biomedical Press, 116(2), 285–288 (1980).

Oellerich, "Enzyme–Immunoassay: A Review", *J. Clin. Chem. Biochem.*, 22, 895–904 (1984).

Sternberg, J. "A Rate Nephelometer for Measuring Specific Proteins by Immunoprecipitin Reactors", Clin. Chem. 23(8), 1456–1464 (1977).

Flygare et al., "Affinity Precipitation of Enzymes", *Appl. Biochem. and Biotech.*, 7, 59–61 (1982).

Alkan, S.S. et al., "Antigen Recognition and the Immune Response . . . ", *J. Exp. Med.* 135:1228–1246 (1972).

Redeuilh, G., et al., "The Use of the Biotinyl Estradiol–Avidin System for the Purification of Nontransformed Estrogen Receptor by Biohormonal Affinity Chromatography", *J. Biological Chemistry*, 260(7):3996–4002 (1985).

LATEX-BASED BIDENTATE IMMUNOINHIBITION ASSAY – 3-REAGENT SYSTEM

LATEX-BASED BIDENTATE IMMUNOINHIBITION ASSAY – 2-REAGENT SYSTEM

ACETAMINOPHEN

SYNTHETIC SCHEME FOR BIOTIN-ACETAMINOPHEN

THC $\Delta^9$-THC-COOH

REAGENTS AND METHODS FOR THE RAPID AND QUANTITATIVE ASSAY OF PHARMACOLOGICAL AGENTS

FIELD OF THE INVENTION

The invention concerns reagents and methods for rapidly and quantitatively assaying the concentration of pharmacological agents in biological samples. More specifically, the invention concerns the formation and use of biotinylated bidentate reagents and immunoassay formats capable of determining the concentration of desired, preselected pharmacological agents, such as cocaine, acetaminophen or digoxin.

BACKGROUND OF THE INVENTION

The ability to assess whether an individual has been exposed to a pharmacological agent, and a capability of determining the concentration of such an agent in a biological sample is of broad importance in medicine, law enforcement and other areas.

In particular, the medical and societal ramifications of substance abuse (cocaine, cannabinoids, opiates, etc.) has necessitated the development of assays capable of detecting such substances. Direct usage of cocaine has increased dramatically during the last decade (Rosenberg, N. M. et al., *Amer. J. Dis. Child.* 145:1430–1432 (1991)). Such usage has increased the prevalence of occult cocaine exposure in neonatals, young children and adolescents to levels approaching 5% in some urban areas of the United States (Rosenberg, N. M. et al., *Amer. J. Dis. Child.* 145:1430–1432 (1991)).

Even otherwise beneficial drugs, such as the analgesic acetaminophen, or the cardioactive glycoside digoxin, can induce life-threatening symptoms if abused or mis-dosed. Indeed, the hepatotoxicity of acetaminophen overdoses has been well-documented (Black, M., *Gastroenterol.* 78:382–292 (1980)). Acetaminophen has also been reported to be nephrotoxic in some individuals (Nelson, S. D., *J. Med. Chem.* 25:753–765 (1982)). Digoxin intoxication or overdose can result in ventricular arrhythmias or tachycardias. In view of the wide use of these pharmacological agents, and the importance of accurately assaying their concentration, a variety of methods have been developed to permit the screening of large numbers of patients.

Immunoassays are assay systems that exploit the ability of an antibody to specifically recognize and bind to a particular target molecule. The region of a molecule that is recognized by an antibody, and to which the antibody binds is referred to as an "epitope." Although large molecules, such as proteins or other "antigens" possess multiple epitopes, low molecular weight molecules, such as most pharmacological agents possess only a single epitope. Such low molecular weight molecules are referred to herein as "haptens." Immunoassays are used extensively in modern diagnostics (Fackrell, *J. Clin. Immunoassay* 8:213–219 (1985)). A large number of different immunoassay formats have been described (Yolken, R. H., *Rev. Infect. Dis.* 4:35 (1982); Collins, W. P., In: *Alternative Immunoassays*, John Wiley & Sons, NY (1985); Ngo, T. T. et al., In: *Enzyme Mediated Immunoassay*, Plenum Press, NY (1985)). Immunoassay formats have been developed that are amenable for such large scale usage (for review, see Lee, T. T. T. et al., European Patent Application Publn. No. 203,238, herein incorporated by reference).

The simplest immunoassay involves merely incubating an antibody that is capable of binding to a predetermined molecule (i.e. the "analyte") with a sample that is suspected to contain the analyte. The presence of the target molecule is determined by the presence, and is proportional to the concentration, of any immune complexes that form through the binding of antibody and analyte. In order to facilitate the separation of such immune complexes from the unbound antibody initially present, a solid phase is typically employed. In more sophisticated immunoassays, the concentration of the target molecule is determined by binding the antibody to a support, and then incubating the bound antibody in the presence of the analyte-containing sample.

Target molecules that have become bound to the immobilized antibody can be detected in any of a variety of ways. For example, the support can be incubated in the presence of a labelled, second antibody (i.e. a "sandwich" immunoassay) that is capable of binding to a second epitope of the target molecule. Immobilization of the labelled antibody on the support thus requires the presence of the target, and is proportional to the concentration of the target in the sample. In an alternative assay, the sample is incubated with a known amount of labelled target and antibody binding site. The presence of any target molecules in the sample competes with the labeled target molecules for the antibody binding sites. Thus, the amount of labelled target molecules that are able to bind the antibody is inversely proportional to the concentration of target molecule in the sample. This is known as a competitive immunoassay.

The various immunoassay formats can be further divided into two main classes, depending upon whether the assay requires the separation of bound species from unbound species. Heterogeneous immunoassays require such purification, and hence entail a separation or isolation step. In contrast, homogeneous assays are designed such that the removal of bound from unbound species is unnecessary. Because homogeneous assays lack a separation step, and are more easily automated, they are more desirable than heterogeneous assays in applications that entail the screening of large numbers of patients.

A heterogeneous assay for digoxin has been developed by Technicon and Triton Biosciences. The assay uses a capture antibody, a digoxin-enzyme conjugate, and a magnetic particle solid phase. The assay is reportedly designed for automated use with the Technicon Immuno-1™ Immunoassay Statem (Mak, A. et al., *Clin. Chem.* 36:1103 (1990)). The use of an alternative automatable immunoassay format (Stratus®, Baxter Healthcare Corp.) to assay digoxin concentration is described by Welch, C. et al., *Clin. Chem.* 36:1187 (1990)). Although such assays are generally useful, their use in patients receiving digoxin FAB antibody therapy may lead to significant misinterpretation of digoxin levels (Ujhelyi, M. R. et al., *Clin. Pharmacol. Therap.* 49:131 (1991)).

The above-described immunoassay formats are generally vulnerable to the sensitivity of the antibody being employed. Thus, where antibody sensitivity is low, closely related metabolites may be incorrectly identified by the assay. Hence, such assays are prone to a significant "false-positive" detection rate (Schwartz, J. G. et al., *Amer. J. Emerg. Med.* 9:166–170 (1991); Cone, E. J. et al., *J. Forens. Sci.* 35:786–781 (1990)). Moreover, for heterogeneous assays, any failure to remove all of the unbound labelled analyte will affect the assay's error rate. For these reasons, immunoassays (especially those for cocaine and other substances of abuse) have generally been used as a preliminary qualitative screen, rather than as a quantitative assay (Cone, E. J. et al., *J. Forens. Sci.* 35:786–781 (1990); Standefer, J. C. et al., *Clin. Chem.* 37:733–738 (1991)). Additional confirmatory methods of assessing cocaine concentration include mass spectroscopy and chromatography (Lee, T. T. T. et al., European Patent Application Pubin. No. 203,238; Schwartz, J. G. et al., *Amer. J. Emerg. Med.* 9:166–170 (1991); Fytche, L. M. et al., *J. Forens. Sci.* 37:1550–1556 (1992); Wernly, P. et al., *Anal. Chem.* 64:215–2159 (1992); Bailey, D. N. et al., *Amer. J. Clin. Pathol.* 99:123–127 (1993)).

Regardless of immunoassay format, the utility of an immunoassay in detecting an analyte depends upon its capacity to report the extent of the formation of immune complexes between the antibody employed and the analyte whose presence or concentration is being measured. In general, two independent approaches exist for increasing this capacity. The first approach involves labeling one or more of the reagents. The second approach involves increasing the size of the immune complex.

A wide array of labels (such as radioisotopes, enzymes, fluorescent moieties, chemiluminescent moieties, or macroscopic labels, such as a bead, etc.) have been employed in order to facilitate the detection of immune complexes (see, Chard, T., et al., In: *Laboratory Techniques and Biochemistry in Molecular Biology* (Work, T. S., Ed.), North Holland Publishing Company, NY (1978); Kemeny, D. M. et al. (Eds.), *ELISA and Other Solid Phase Immunoassays*, John Wiley & Sons, NY (1988)). Radioisotopes have long been used in immunoassays. O'Leary, T. D. et al., for example describe a radioimmunoassay ("RIA") for digoxin serum concentrations (O'Leary, T. D. et al., *Clin. Chem.* 25:332–334 (1979)). RIAs have the advantages of simplicity, sensitivity, and ease of use Radioactive labels are of relatively small atomic dimension, and do not normally affect reaction kinetics. Such assays suffer, however, from the disadvantages that, due to radioisotopic decay, the reagents have a short shelf-life, require special handling and disposal, and entail the use of complex and expensive analytical equipment. The difficulty of handling such hazardous materials, and the problem of radioactive decay have led to the development of immunoassays that use other labels.

Enzymes, in particular, are now widely used as labels in immunoassay formats. An enzyme-multiplied immunoassay technique (EMIT®, Syva Co.) has been used to analyze the presence of cocaine in biological fluids. The procedure is based on a competition between an antigen (e.g. the cocaine metabolite benzoylecgonine) and an antigen-enzyme conjugate, for binding sites on an antibody present in limiting amounts (Cone, E. J. et al., *J. Forens. Sci.* 35:786–781 (1990); Baugh, L. D. et al., *J. Forens. Sci.* 36:79–85 (1991); Standefer, J. C. et al., *Clin. Chem.* 37:733–738 (1991)). The method has been found to have an efficiency of between 80–90%, with the majority of errors being false-positive results (Schwartz, J. G. et al., *Amer. J. Emerg. Med.* 9:166–170 (1991); Cone, E. J. et al., *J. Forens. Sci.* 35:786–781 (1990)). The EMIT® format has also been used to assay acetaminophen in serum (Helper, B. et al., *Amer. J. Clin. Pathol.* 81:602–610 (1984); Cambell, R. S. et al., *J. Clin. Chem. Clin. Biochem.* 24:155–159 (1986); Khanna, P., U.S. Pat. No. 5,103,021). Indirect assays of acetaminophen, based upon the recognition that acetaminophen toxicity is mediated by the formation of a protein-bound acetaminophen complex and that the concentration of such bound acetaminophen can be used to measure the severity of acetaminophen toxicity, have also been described (Roberts, D. W. et al., *J. Pharmacol. Exper. Therap.* 241:527–533 (1987); Bartolone, J. B. et al., *Biochem. Pharamcol.* 37:4763–4774 (1988)). Enzyme-linked immunoassays ("ELISAs") have the advantage that they can be conducted using inexpensive equipment, and with a myriad of different enzymes, such that a large number of detection strategies—calorimetric, pH, gas evolution, etc.—can be used to quantitate the assay. In addition, the enzyme reagents have relatively long shelf-lives, and lack the risk of radiation contamination that attends to RIA use. ELISAs are described in *ELISA and Other Solid Phase Immunoassays* (Kemeny, D. M. et al., Eds.), John Wiley & Sons, NY (1988), incorporated by reference herein.

In addition to enzymes, fluorescent moieties are frequently used as labels. A fluorescence polarization immunoassay format for cocaine (TDx®, Abbott Laboratories, Inc.) has been found to be approximately equivalent to the EMIT® formats (Schwartz, J. G. et al., *Amer. J. Emerg. Med.* 9:166–170 (1991)). The TDx® format has also been used to assay acetaminophen serum levels (Koizumi, F.et al., *Tohoku J. Exper. Med.* 155:159-(1988); Edinboro, L. E. et al., *Clin. Toxicol.* 29:241-(1991); Okurodudu, A. O. et al., *Clin. Chem.* 38:1040 (1992)), serum digoxin levels (Okurodudu, A. O. et al., *Clin. Chem.* 38:1040 (1992)) and theophylline levels (Klotz, U., *Ther. Drug. Monitor.* 15:462–464 (1993)). Wong, S. H. Y., et al., have described the use of an automated (OPUS) analyzer to measure digoxin concentration in a monoclonal antibody mediated, fluorescence-based assay protocol (Wong, S. H. Y. et al., *Clin. Chem.* 38:996 (1992)). Lee, D. H. et al. also disclose the use of a fluorescence polarization assay and a chemiluminescent assay format to assay digoxin levels (Lee, D. H. et al., *Clin. Chem.* 36:1121 (1990)).

As indicated, immunoassay sensitivity can be enhanced by increasing the size of the immune complex that is formed in the immunoassay. If the immune complex is large enough, it will become capable of scattering light, or of spontaneously precipitating. In such cases, agglutination, or nephelometric or turbidimetric immunoassay methods may be employed. Nephelometric methods measure the light scattered by a suspension of particles or reflected toward a detector that is not in the direct path of light (Sternberg, J. C., *Clin. Chem.* 23:1456–1464 (1977)). In contrast, turbidimetric methods measure the reduction of light transmitted through the suspension of particles or aggregates. The reduction is caused by reflection, scatter, and absorption of the light by the aggregates. In both nephelometry and turbidimetry, the rate of change in light scatter may also be measured, and provides an indication of the amount of antigen present. Agglutination assays measure the precipitation of antibody-antigen complexes. Such assays can be extremely sensitive, and are amenable to automation. Because nephelometric and turbidimetric methods do not require the separation of the initially present antibody from the immune complexes formed in the assay, such assays are homogenous immunoassays. An agglutination inhibition assay for cocaine is commercially available (OnTrak™, Hoffman-LaRoche) but appears to be substantially less efficient than the above methods (Schwartz, J. G. et al., *Amer. J. Emerg. Med.* 9:166–170 (1991)).

The requirement of producing large immune complexes has limited the applicability of nephelometric, turbidometric or agglutination immunoassays to high molecular weight molecules, such as proteins, that possess several epitopes (i.e. antibody binding sites). In particular, many pharmacological agents have only a single epitope, and as such are incapable of forming the large immune complexes needed for such immunoassays.

Two approaches have been exploited to define agglutination assays for small molecular analytes. One approach involved the agglutination of antibody-coated particles with a polyepitopic species or a developer antigen containing at least two covalently coupled hapten analogs (e.g., a protein carrier, such as BSA) (Mongkolsirichaikul, D. et al., *J. Immunol. Meth.* 157:189–195 (1993)). The agglutination reaction required the use of a developer antigen or a polyepitopic species because a molecule that has only one epitopic site cannot bind two antibodies, and hence cannot cross-link two antibodies together. Such cross-linking is however an essential step in the formation of large immune complexes. The second approach involved the agglutination of hapten-coated particles and antibody for the agglutination reaction.

With either method, the hapten or drug in the sample competitively binds to the antibody binding sites and results in inhibition or reduction of the imunoagglutination. Particle agglutination assays for therapeutic drugs and drugs of abuse which use hapten coated particles are commercially available. Examples of such assays are PETINIA (Du Pont) and AbuScreen (Roche), Advisor (Abbott) and that of Mitsubishi.

A third solution to this problem has recently been described by Oh, C. S. et al. in U.S. Pat. No. 5,168,057 and by Harris, P. C. et al. in U.S. Pat. No. 5,196,351, both herein incorporated by reference, and involves the use of bidentate or tridentate analyte reagents. The reagents are formed by linking an analyte of interest to one or two additional molecular moieties. The moieties are selected such that each can independently bind to an antibody or to a specific binding partner. Thus, for example, the monoepitopic molecule, theophylline can be converted to a theophylline-biotin conjugate. The theophylline portion of the molecule can bind to anti-theophylline antibodies, and the biotin portion of the molecule is able to bind to, for example, avidin. In this manner, the bidentate and tridentate reagents convert monoepitopic molecules into bi- or tri-epitopic molecules. The presence of the additional epitopes permits the reagents to form immune complexes that are large enough to participate in light scattering or agglutinization reactions.

Despite the success of the methods of Oh, C. S. et al. (U.S. Pat. No. 5,168,057) and Harris, P. C. et al. (U.S. Pat. No. 5,196,351) methods that would enhance both the rate of immune complex formation, and the size of the complex would provide more efficient and effective immunoassays for determining the concentration of medically important pharmacological agents. The present invention provides reagents and methods for conducting such improved immunoassays.

SUMMARY OF THE INVENTION

The invention relates to reagents, especially bidentate reagents that can be used to assay the concentration of preselected pharmacological agents in a biological sample. The invention also pertains to assay formats that employ such reagents.

In detail, the invention provides an assay for determining the presence of a target analyte in a test sample comprising the steps of:

(A) forming a reaction mixture by contacting a test sample with:
 (i) a soluble bidentate reagent comprising a biotin member, an analyte member, and a spacer member between the biotin and analyte members, wherein:
  (a) the biotin member of the reagent is capable of binding to a biotin-binding agent selected from the group consisting of avidin and streptavidin; the biotin-binding agent being immobilized to a solid support (especially a latex support);
  (b) the analyte member of the reagent is capable of specifically binding to an antibody capable of binding to the target analyte;
  (c) the intermediate spacer member is sufficient in length to permit the analyte member to bind to an anti-target analyte antibody and the biotin member to bind to a biotin-binding ligand;
 (ii) the anti-target analyte antibody; and
 (iii) the biotin binding agent;
(B) incubating the reaction mixture under conditions sufficient to permit the formation of a complex between the bidentate reagent, the anti-target analyte antibody, and the biotin binding agent; and
(C) measuring the extent of any formation of the complex, the extent being inversely proportional to the concentration of the target analyte in the sample.

The invention is particularly concerned with the embodiment of the above assay wherein the antibody is capable of binding an analyte such as benzoylecgonine, cocaine, an opiate, PCP, digoxin, acetaminophen, carbamazepine, primidone, phenytoin, an aminoglycoside antibiotic, vancomycin, quinidine or a cannabinoid.

The invention also provides an avidin-latex conjugate formed by incubating latex and avidin in the presence of N-hydroxysuccinimide and 1-ethyl-3-(3-dimethylaminopropyl) carbodiimide under conditions sufficient to immobilize the avidin to the latex.

The invention also provides a method for immobilizing avidin to latex comprising the steps:

(A) incubating an aqueous suspension of latex particles in the presence of a conjugating agent, and a water soluble carboiimide, at a pH of about 6;
(B) adding avidin to the incubation, and permitting the conjugating agent to conjugate the avidin to the latex particles at alkaline pH.

The invention also provides a method for preparing a bidentate reagent comprising a biotin member, an analyte member, and a spacer member between the biotin and analyte members, and sufficient in length to permit the biotin member to bind to a biotin-binding ligand, and the analyte member to bind to an antibody, the method comprising the steps:

(A) converting a reactive amine group of an analyte precursor into an isothiocyanate group; and
(B) condensing the isothiocyante group with an amine group of an alkyamidobiotin, the alkyamidobiotin comprising the spacer and biotin members.

The invention also provides a method for preparing a bidentate reagent comprising a biotin member, an analyte member, and a spacer member between the biotin and analyte members, and sufficient in length to permit the biotin member to bind to a biotin-binding ligand, and the analyte member to bind to an antibody, the method comprising the steps:

(A) converting a reactive amine group of an analyte precursor into a carboxyl group; and
(B) condensing the carboxyl group with an amine group of an alkyamidobiotin, the alkyamidobiotin comprising the spacer and biotin members.

The invention also provides a method for preparing a bidentate reagent comprising a biotin member, an analyte member, and a spacer member between the biotin and analyte members, and sufficient in length to permit the biotin member to bind to a biotin-binding ligand, and the analyte member to bind to an antibody, the method comprising the steps:

(A) converting a hydroxyl group of an analyte precursor into an amine group;

(B) converting the amine group into an amido group; and (C) condensing the amido group with an amine group of an alkyamidobiotin, the alkyamidobiotin comprising the spacer and biotin members.

The invention also concerns a bidentate reagent comprising a biotin member, an analyte member, and a spacer member between the biotin and analyte members, and sufficient in length to permit the analyte member to bind to an anti-analyte antibody and the biotin member to bind to a biotin-binding ligand, wherein the analyte member is benzoylecgonine, cocaine, an opiate, PCP, digoxin, acetaminophen, carbamazepine, primidone, phenytoin, an aminoglycoside antibiotic, quinidine, vancomycin or a cannabinoid.

DESCRIPTION OF THE PREFERRED EMBODIMENTS

Figure 1:
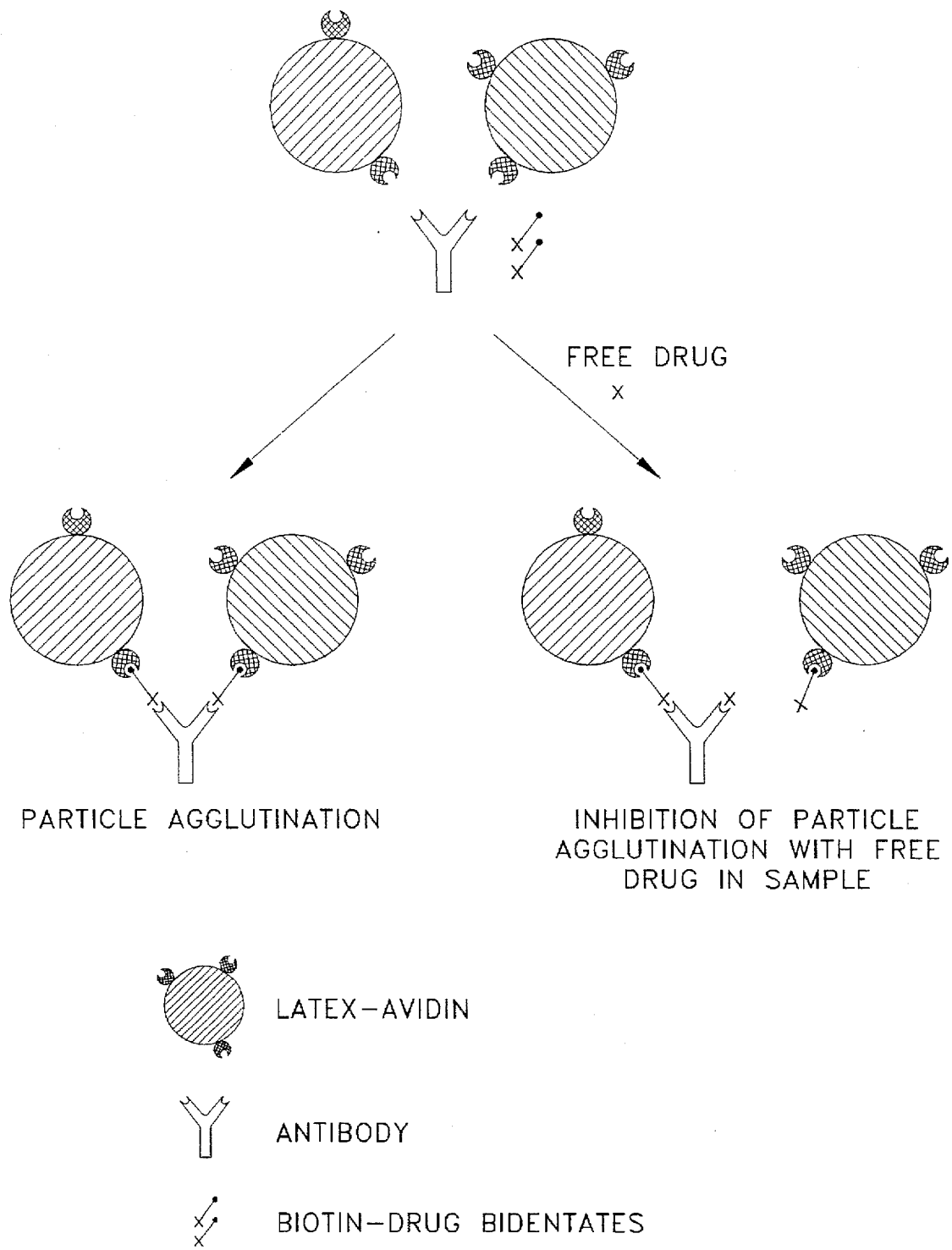
FIG. 1 shows a diagrammatic representation of the 3-reagent system for the particle-enhanced immunoassay of the present invention.

The present invention concerns assays and reagents that can be used in immunoassay formats to measure the concentration of a preselected agent in a sample. The invention is particularly concerned with the detection and quantification of low molecular weight molecules, such as pharmacological agents.

As indicated, Oh, C. S. et al. (U.S. Pat. No. 5,168,057) and Harris, P. C. et al. (U.S. Pat. No. 5,196,351) describe the synthesis and use of bidentate and tridentate reagents that can be used to define nephelometric and turbidometric immunoassays for low molecular weight, monoepitopic molecules. One embodiment of the present invention is directed to the use of macroscopic particles to increase the size of the immune complexes that are formed using bidentate reagents. A second embodiment of the invention is directed to improved methods for forming such bidentate reagents.

Thus, the present invention extends the accomplishments of Oh, C. S. et al. (U.S. Pat. No. 5,168,057) and Harris, P. C. et al. (U.S. Pat. No. 5,196,351) by providing improved immunoassay formats that use bidentate molecules, and by providing methods and reagents capable of measuring the presence or concentration of pharmacological agents such as benzoylecgonine, cocaine, digoxin, primidone, acetaminophen, vancomycin, carbamazepine, theophylline, aminoglycoside antibiotics, quinidine and cannabinoids.

I. THE IMMUNOASSAY FORMATS OF THE PRESENT INVENTION

In bidentate immunoassay methods (Oh, C. S. et al., U.S. Pat. No. 5,196,351; Harris, P. C. et al., U.S. Pat. No. 5,196,351; Oh, C. S. et al., In: Nonisotopic Immunoassay, Ngo, T. T. (Ed.), Plenum Press, NY, pp.457–476 (1988)) the immune complex forms through two distinct binding reactions. One reaction involves the binding of avidin to the biotin member of a biotinylated bidentate having a biotin member and an analyte member. The other reaction is the immunoreaction of an antibody to the hapten portion of the bidentate. Because antibody has two hapten binding sites, and avidin has four biotin binding sites, an immunocomplex is formed when the antibody, bidentate reagent, and avidin are mixed together. The formation of the immunocomplex is rapid and appears to be associated with the positive charge (pl 10) of the approximately thirty five lysine termini of avidin in addition to the strong binding of avidin and biotin. This specific charge-assisted immunoprecipitin reaction is a characteristic feature of the biotin-avidin methodology. Under similar conditions, streptavidin (pl 5) or charge neutralized avidin fails to produce the immunoprecipitin reaction with high rate.

In practice, steric hindrance between the Fab portion of the antibody (i.e., the hapten binding portion of the antibody) and avidin may block some of the avidin's four biotin-binding sites. Such blockage restricts both the rate and extent of immune complex formation. For example, if the spacer length between the hapten and biotin is less than about 27Å, steric hindrance between avidin and the Fab portion of the antibody will block two of avidin's four biotin binding sites (Oh, C. S. et al., In: Nonisotopic Immunoassay, Ngo, T. T. (Ed.), Plenum Press, NY, pp.457–476 (1988)). Such blockage causes the immune complex to be linear:

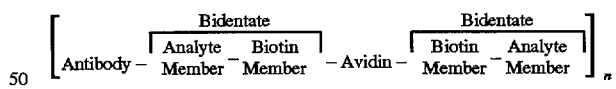

The linear polymer results in a turbidity change or in light scattering which can be monitored on a turbidimeter or nephelometer, respectively. If hapten is present in the sample, it will compete for antibody with the hapten member of the bidentate reagent. Such competition leads to a reduction in the rate of immune complex formation. Thus, the rate of the nephelometric or turbidimetric response becomes inversely proportional to the concentration of the hapten in the sample.

II. THE PARTICLE-ENHANCED IMMUNOASSAY FORMATS OF THE PRESENT INVENTION

The present invention is directed toward an improved immunoassay for detecting or quantitating the presence of small molecular weight analytes, especially haptens. The immunoassay exploits the biotin bidentate reagents described by Oh, C. S. et al. (U.S. Pat. No. 5,196,351) and by Harris, P. C. et al. (U.S. Pat. No. 5,196,351). The immunoassay further involves the use of particles that have been labeled with a biotin-binding agent. Any of a variety of methods may be used to accomplish such labeling (e.g., covalent, ionic or affinity binding).

The biotin binding agent may be an anti-biotin antibody (or a fragment of such an antibody), streptavidin or avidin. Avidin is a relatively large macromolecular protein found in egg whites; streptavidin is a structurally similar molecule isolated from bacterial sources.

Avidin is the most preferred biotin-binding agent of the present invention. Avidin contains four subunits. Each of the four subunits of an avidin molecule is capable of specifically binding to a molecule of biotin. The binding reaction between avidin and biotin is very strong, with the binding constant being approximately $10^{15}$ l/mole. The very strong nature of this bond has been found to persist even when biotin is conjugated, by means of its carboxyl group, to another molecule, or when avidin is attached to another molecule. When biotin is conjugated to another molecule, the resulting conjugate is usually referred to as a biotinylated compound; e.g., a biotinylated bidentate. A biotinylated molecule may, for example, quickly become strongly bound to a corresponding avidin-attached molecule. This feature of linking up biotinylated compounds with avidin conjugates has been employed, with varying degrees of success, mostly in heterogenous immunoassays. For example, in U.S. Pat. No. 4,228,237, a biotinylated specific-binding partner for the ligand to be measured is employed in conjunction with enzyme-labeled avidin in a sandwich immunoassay. In an alternative format, disclosed in U.S. Pat. No. 4,298,685, the biotin:avidin bond may be used at the insolubilized end of the sandwich formed in a sandwich immunoassay.

The particles employed in accordance with the methods of the present invention are macroscopic particles of plastic, latex, glass, metal, etc. The particles may be beads, cubes, etc. In one embodiment, the particles may comprise magnetic beads. The use of such macroscopic particles decreases the extent of complex formation needed to obtain a discernible change in light scatter or reflection. Thus, because of the presence of the macroscopic particle, immune complexes that would otherwise be too small to be detectable can be readily measured. The presence of the particles affects both the rate of detectable complex formation, and the lower limit of analyte that can be detected using nephelometric or turbidimetric methods.

Latex particles, and in particular, carboxylated latex particles, are the most preferred particles. The size of the latex particle can vary from less than 50 nm to more than 100 μm. The use of small particles (38–100 nm) is preferred for immunoassays that measure analyte concentration by turbidometric or nephelometric means. In such immunoassays, the use of 60–100 nm particles is particularly preferred. Such particles are obtainable from Seradyn, Inc., Indianapolis, Id., U.S. Each 60 nm particle contains on the average approximately 10,000 carboxyl groups and each 100 nm particle carries approximately 25,000 groups available for covalent coupling. The use of larger particles (10–100 μm), however, permits the immune complexes to adsorb infra-red radiation, and to thereby measure analyte concentration using near infra-red, infra-red or thermal detectors.

Optimal coupling of avidin to carboxylated latex particles can be attained by monitoring the avidin to latex ratio, the pH of the reaction medium, and inclusion of detergent. The preferred coupling procedure involves two steps: the activation of carboxyl groups with carbodiimide and N-hydroxysuccinimide followed by reaction with avidin. Since avidin has an isoelectric point (pI) of 10, the pH of the second step of the reaction is preferably maintained slightly basic (pH 8.5 to 9). Such conditions ensure that a sufficient number of avidin molecules will remain in their free base form, and will thus be available for nucleophilic reaction with the activated carboxylated groups on the latex particles. At pH 8 or lower, latex particles may begin to agglutinate as soon as avidin is added. Some agglutination occurs at low pH, perhaps due to the charge interactions between avidin and the latex particle or capture of the particles by avidin via physical adsorption. Overloading the particles with avidin at pH 8.5 to 9 can also result in particle agglutination. When Tween-20 is used as the detergent at 0.13% in the reaction mixture, a total of 150 molecules of avidin per latex particle has been found to be optimal for coupling to the 60 nm particles obtained from Seradyn, Inc. Unless more Tween-20 is used, avidin in excess of this amount can undesirably induce agglutination of the particles. The 100 nm particle has a larger surface area and, in spite of its lower carboxyl content per unit weight of latex, carries about twice the number of carboxyl groups as the 60 nm particles. With the 100 nm particles, as much as 700 avidin molecules per particle can be used for the coupling reaction.

The avidin-labeled particles of the present invention can be produced by incubating latex particles in the presence of hydroxysuccinimide and carbodiimide at 4° C. The pH of the mixture is then raised to about 9.0, and avidin is added. The latex-avidin complex can be recovered by chromatographic means (such as by Sepharose CL-6B purification, or ultrafiltration using large pore membranes), preferably after dialysis to remove the coupling reagents.

In a particularly preferred method for coupling these reagents, carboxylated latex is suspended in a solution of approximately 0.1M [3(N-morpholino)] propanesulfonic acid ("MOPS") (pH 6.0), approximately 0.5% polyoxyethylene (20) sorbitan ("Tween-20") (pH 6). The suspension is cooled to approximately 4° C. and provided with ⅕ volume of cold 0.1M MOPS (pH 6) containing 63 mg /ml of N-hydroxysuccinimide. One tenth volume of 0.1M MOPS (pH 6) containing 46 mg /ml of a water soluble carbodiimide is then added. The resulting mixture is then adjusted to pH 5.5–6, and stirred for approximately 1 hour at about 4° C. Thereafter, the pH is raised to about 9, and the reactants are permitted to react for an additional 5 hours with about 2 volumes of cold 0.02M borate buffer (pH 9) containing dissolved avidin at about 0.6 mg/ml.

BSA is then added to a final concentration of approximately 2 mg/ml, and the solution is stirred overnight at about 4° C. After this incubation, the latex-avidin mixture is dialyzed against 3 changes of 0.02M Tris (pH 9) buffer, containing 0.2% Tween-20 for 1.5 days, and purified, either by passage through a sepharose CL-6B column, or by other means (such as the Pellicon Cassette system (PCS)) and membrane having a molecular weight cutoff (MWCO) of 300 k. Such avidin-labeled particles may be used in conjunction with any of the immunoassay formats described herein that employ a biotinylated bidentate reagent.

Heat stressing the latex-avidin before coupling to the bidentate or the latex-avidin-bidentate conjugate itself for 3 to 6 days at 45° C. enhances the immunoreactivity and assay sensitivity in terms of steeper dose response.

The particle-enhanced bidentate assay offers several advantages as compared to the liquid formulated bidentate method. The use of particles provides better sensitivity and requires less reagent and smaller sample volumes than in the liquid-based methods. An improvement of a factor of 10 or more in antibody usage and a reduction of 1.3 to 5 times in sample volume can be achieved for the same or a steeper dose response. The use of more diluted antibody and less sample also lowers contribution background signal from these materials and sample-to-sample matrix variations. Such use additionally reduces interference from the sample and antibody matrices including non-specific precipitations and provides greater flexibility with regard to the selection of a suitable calibrator matrix. For example, lipemic samples or triglyceride-rich samples interfere substantially with the liquid formulated bidentate assays. At triglyceride concentrations of 250 mg/dl or higher, a quantitation error of more than 10% in the measurement of analyte concentration has been observed. Such interference was not observed with the latex formulation.

Two embodiments of the particle-enhanced immunoassay are particularly preferred: a 3-reagent system, and a 2-reagent system. The embodiments are described with reference to avidin, however, as indicated above, other biotin-binding agents may be employed. The use of such particles is illustrated below with respect to immunoassays for detecting any of a variety of pharmacological agents (e.g., benzoylecgonine, cocaine, digoxigenin, acetaminophen, carbamazepine, primidone, theophylline, aminoglycoside antibiotics, vancomycin, quinidine and cannabinoids).

A. THE 3-REAGENT SYSTEM

In the "3-reagent system" embodiment of the invention, the immunoassay is conducted using three components: the avidin-labeled particles, the bidentate and the anti-analyte antibody.

The immune complex is formed by a reaction of the avidin-coated particles with the bidentate reagent in the presence of an anti-analyte antibody. This aspect of the invention is illustrated in FIG. 1.

As shown in FIG. 1, the formation of an immune complex is dependent upon the binding of the latex-avidin particles to the biotin portion of the bidentate, and the binding of the antianalyte antibody to its binding site on the analyte portion of the bidentate. Extensive complex formation is possible because both the antibody and the latex avidin particles are capable of binding multiple bidentate molecules. As illustrated, because the analyte has only a single epitope, the presence of analyte in the sample being evaluated blocks immune complex formation by competing with the bidentate for antibody binding sites. The extent of complex formation is thus inversely proportional to the concentration of analyte in the sample.

B. THE 2-REAGENT SYSTEM

In the "2-reagent system" embodiment of the invention, the immunoassay is conducted using only two components: an avidin-labeled particle in which all biotin binding sites have been saturated with the biotin member of a bidentate biotin-analyte reagent, and an anti-analyte antibody. This aspect of the invention is illustrated in FIG. 2.

Figure 2:
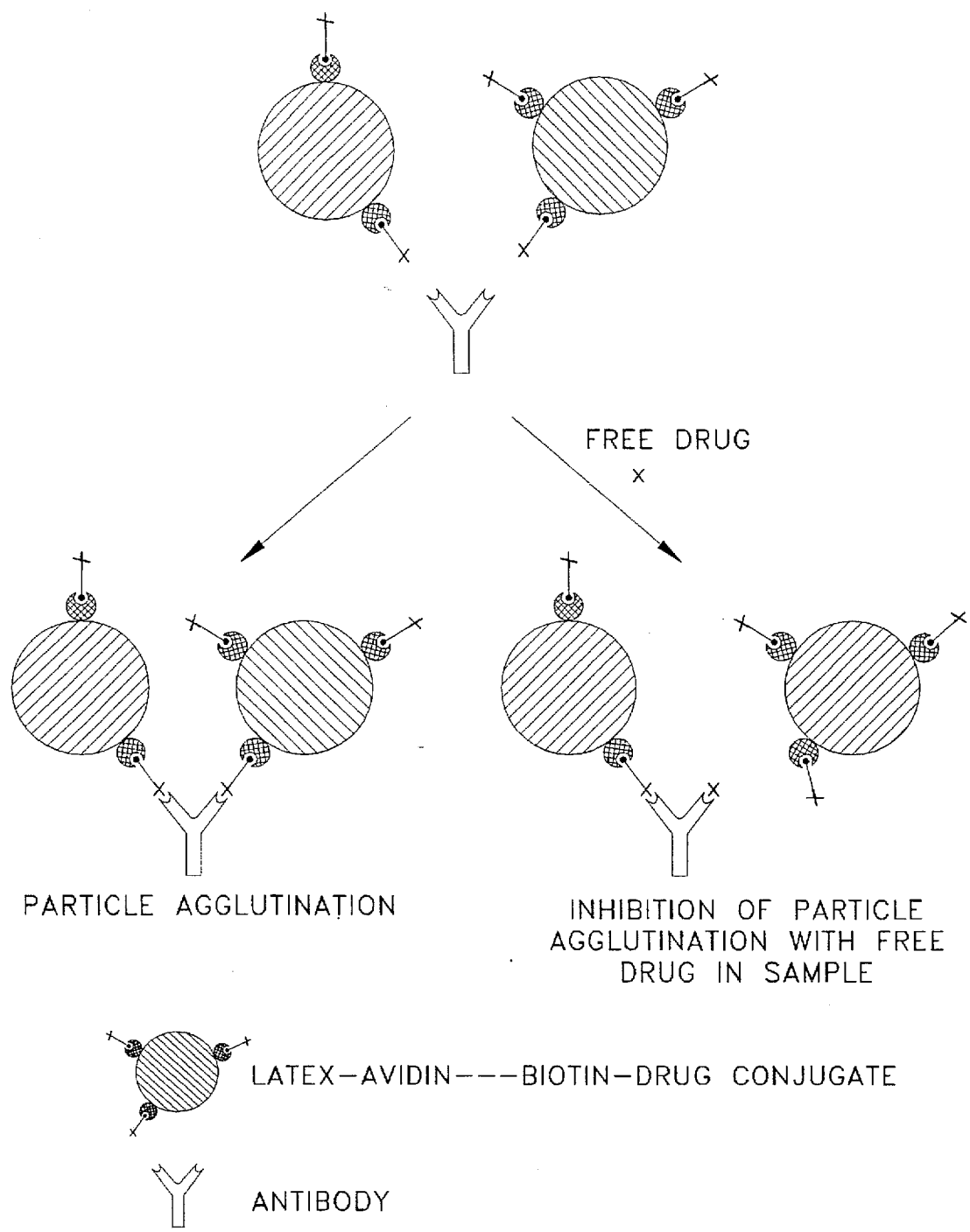
FIG. 2 shows a diagrammatic representation of the 2-reagent system for the particle-enhanced immunoassay of the present invention.

As indicated in FIG. 2, in this embodiment of the invention, the latex-avidin particles are preincubated with the bidentate under conditions of bidentate excess, such that substantially all of the biotin binding sites are filled with the biotin member of the bidentate. After removal of the excess bidentate by size exclusion column chromatography, dialysis, or other means, the resulting latex-avidin-analyte particle will thus be conjugated to the bidentate in a manner that permits the analyte portion of the bound bidentate to be accessible for subsequent binding with an anti-analyte antibody. This reagent can thus serve as the conventional "developer antigen" in an inhibition immunoassay and hence can form an immune complex when incubated in the presence of anti-analyte antibody. As in the 3-reagent system, the presence of analyte in the sample being evaluated will compete for analyte binding sites, and will attenuate the extent of complex formation. The extent of immune complex formation is inversely proportional to the concentration of analyte in the sample.

An inherent advantage of the preferred 2-reagent system is the simplicity of the manufacturing process in terms of reducing the number of reagents to manufacture and hence documentation and quality control. On the other hand, in the 3-reagent system, the avidin-latex reagent is a "universal" reagent for any small molecular weight analyte, and can be used in conjunction with different bidentate reagents and antibodies for different agglutination test kits. The 2-reagent system is more amenable for use with automated processing methods, since these methods generally allow only two reagents to be picked up into the reaction chamber after the buffer and sample are introduced.

There are additional differences between the 3- and the 2-reagent systems in the area of assay and reagent optimization. In the 2-reagent system, which uses the avidin-latex-bidentate conjugate, the dose-response curve is not readily changed by modifying the conjugate:antibody ratio in contrast to conventional liquid reagent systems. However, the dose response can be changed by varying the avidin loading on the latex and, to some extent, the particle size. In this regard, the use of the latex-avidin universal reagent from the 3-reagent system offers the flexibility to achieve the desired dose response. Depending upon the triggering bidentate concentration, various dose-response curves can be obtained. Thus, the 3-reagent system is more amenable for assay and reagent optimization.

Because the bidentate triggering reagent of the 3-reagent system is separately formulated, it is possible to select an optimal buffer composition for the ultimate chemical stability of the immunochemical reagent component. The buffer selection is important as some bidentates such as the cocaine bidentate contain hydrolytically unstable ester linkage. In the case of the cocaine bidentate, for example, the buffer is kept at around pH 6, and a considerably longer storage life for the ester linkage is achieved.

In the 3-reagent system, varying the bidentate concentration at fixed antibody dilution and latex-avidin concentration results in an expected "bell-shaped" rate profile (see, Eisen, H. N., In: *Microbiology*, 2nd Edition (Davis, B. D. et al., Eds.), Harper & Row, NY, pp. 370–386 (1973)). Use of excess amount of bidentate saturated the antibody binding sites and/or avidin prevented it from participating in latex agglutination thus resulting in decrease of reaction rate. On the other hand, when an insufficient amount of bidentate was used, only a small number of avidin binding sites on the latex particles was used in agglutination, and a low reaction rate was observed.

III. THE DETECTION OF ANALYTE

The immunoassays of the present invention may be used to assay the presence or concentration of analytes in biological samples (such as blood, serum, sputum, urine, cerebrospinal fluid (CSF), etc.) as well as forensic samples (such as clothing, chemical residues, dust or powders, etc.).

In a preferred embodiment, the detection of the analyte is accomplished using the above-described nephelometric or turbidometric immunoassays of Harris, P. C. et al. (U.S. Pat. No. 5,196,351).

The reagents of the present invention can, however, be used in any of a variety of alternative heterogeneous or homogeneous immunoassay formats. For example, a defined amount of the bidentate reagent could be incubated with an aliquot of a sample in the presence of an antibody that is capable of binding the analyte member of the bidentate. In such an assay, the amount of bidentate reagent that becomes bound to the antibody will be inversely proportional to the amount of hapten present in the sample. In one embodiment, the biotin member of the bidentate reagent could be radiolabelled. If desired, the antibody can be immobilized to a solid support, and the extent of binding determined using an avidin-enzyme, or avidin-biotin-enzyme complex. Alternatively, such detection can be accomplished through the use of anti-biotin antibodies. As indicated, the use of larger particles permits the detection of the immune complex by thermal detectors.

In one homogeneous immunoassay format, avidin can be used as a modulator of the capacity of the biotin member of the reagents of the present invention to function as a co-factor of a biotin-requiring enzyme. Thus, they can be used in a method that is analogous to that described by Bacquet et al. (U.S. Pat. No. 4,550,075) or Horaby et al. (U.S. Pat. No. 4,238,565).

In particular, however, the bidentate reagents of the invention and the biotin-binding particles can be used to define novel two-site or "sandwich" immunoassays for haptenic analytes. In a sandwich assay, one component of the reaction (either the antigen, or an antibody that binds to the antigen) becomes bound (i.e. "sandwiched") by a second antibody. In a preferred "sandwich" assay of the present invention, the bidentate reagent (by virtue of the binding of its analyte member and its biotin member) becomes "sandwiched" by an anti-analyte antibody and a biotin binding molecules. Significantly, such a structure differs from that created in conventional "sandwich" assays in that it may form- using only a single antibody species.

Conventional immunoassays involve multi-epitopic molecules. A variety of such sandwich immunoassay formats have been described. In one common format, two antibodies are employed. The first antibody is capable of binding the antigen of interest and is bound to a solid support (such as a microtiter plate, test tube, dipstick, etc.). The support is placed in contact with the sample that is being evaluated and used to immobilize any antigen present in the sample. The support is then washed, and placed into contact with the second antibody. The second antibody is typically labeled, and is capable of binding a second epitope of the antigen. After a second incubation period to permit the labeled antibody to complex with the immobilized antigen, the support would be washed a second time to remove the unreacted labeled antibody. This type of forward sandwich assay may be a simple "yes/no" assay to determine whether antigen is present or may be made quantitative by comparing the amount of retained labeled antibody with that obtained for a samples containing known quantities of antigen. Such assays are described by Wide, In: *Radioimmune Assay Method*, (Kirkham et al., Ed.), E. & S. Livingstone, Edinburgh, pp 199–206 (1970), herein incorporated by reference). The amount of detectably labeled antibody to become immobilized to the support is directly proportional to the concentration of antigen in the sample being evaluated.

In an alternate conventional format, an immobilized antibody specific for a particular antigen is incubated with the sample along with a detectably labeled unbound antibody. After the incubation is completed, the solid support is washed to remove the residue of fluid sample and uncomplexed labeled antibody. The presence of labeled antibody associated with the solid support is then determined as it would be in a conventional "forward" sandwich assay. The avidin-latex particles of the invention and the bidentate reagents may be used to define a simultaneous immunoassay by merely incubating the immobilized molecule and the sample together in the presence of the labeled molecule.

Unlabeled antigen may be bound to the support. In such an immunoassay, an unlabelled antibody capable of binding the antigen is incubated with the sample and then placed in contact with the solid support. Antibody that has not bound to antigen of the sample binds to the immobilized antigen and can be detected using a second, labeled antibody that is capable of binding the first antibody. In a reverse assay, the amount of the second labeled antibody bound to the support is inversely porportional to the amount of antigen in the sample.

As indicated, the reagents of the present invention may be used to design sandwich immunoassays for haptens. In one embodiment, for example, the avidin-latex particles of the invention may be immobilized to a solid support and used in conjunction with a bidentate reagent whose analyte member is capable of binding an anti-hapten antibody) and a labeled anti-analyte antibody (i.e. an anti-hapten antibody) in a sandwich immunoassay. A variety of solid supports may be used for this purpose. Indeed, in one embodiment, the latex particle may be replaced with a latex sheet, cylinder, etc. and the avidin molecules can be linked directly to such support. Alternatively, the support may be biotinylated, such that the avidin-labeled particles will become immobilized to the support through a biotin-avidin interaction.

In one sub-embodiment, a limiting amount of detectably labeled molecule is employed, and the amount of non-immobilized labeled molecule is determined. The amount of detectably labeled molecule that is not immobilized to the support will be directly proportional to the concentration of analyte in the sample being evaluated.

By immobilizing the biotin member of the bidentate directly to the solid support, the present invention can be used to define an alternative sandwich immunoassay. In this embodiment, the analyte portion of the immobilized bidentate would be incubated with a labeled anti-analyte antibody in the presence of the sample (or after incubation with the sample). Analyte present in the sample will compete with the immobilized analyte for antibody binding. The extent of antibody binding will thus be inversely proportional to the amount of analyte in the sample.

In its most preferred embodiment, the immunoassays of the present invention will employ monoclonal antibodies. Most preferably, such antibodies are generated by immunizing a mouse, rat, rabbit, etc. with the analyte of interest conjugated to an antigenic protein, or in concert with an adjuvant, harvesting the splenic leukocytes of the animal, and fusing them with a suitable myeloma cell. In one embodiment, such monoclonal antibodies can be directly employed in an immunoassay format. Alternatively, such antibodies may be cleaved or processed to form fragments that retain the capacity to bind the analyte. Examples of such fragments include (F(ab'), F(ab')$_2$ fragments.

The solid supports discussed above may be composed, for example, of materials such as glass, paper, polystyrene, polypropylene, polyethylene, dextran, nylon, amylases, natural and modified celluloses, polyacrylamides, agaroses, or magnetite. The nature of the support can be either soluble to some extent or insoluble for the purposes of the present invention. The support material may have virtually any possible structural configuration. Thus, the support configuration may be spherical, as in a bead, or cylindrical, as in the inside surface of a test tube, or the external surface of a rod.

Alternatively, the surface may be flat such as a sheet, test strip, etc. Those skilled in the art will note many other suitable carriers for binding monoclonal antibody, or will be able to ascertain the same by use of routine experimentation. In one embodiment, the support will be a polystyrene microtiter plate.

Regardless of format, the processing of the immunoassay is most preferably automated using an automated sample processing system. Although any suitable system may be employed using the bidentate reagents of the present invention, the automated method of Pang, W. S. et al. described in U.S. Pat. No. 5,162,236 (herein incorporated by reference) is particularly preferred. In general, the method of Pang et al. employs an apparatus to control the temperature and volume of the reagents. The immunoassay is conducted in a cuvette within a nephelometric optics module. A sensor of the apparatus senses the temperatures of reaction buffer liquids as they flow into the cuvette, and a heat exchanging device increases or decreases the temperatures of the buffer liquids, as necessary. A control circuit responsive to the temperature sensor controls the heat exchanging device to maintain the temperature of the buffer liquids and the cuvette within a selected temperature range. The system preferably includes a sample pickup station, a sample probe for withdrawing a selected sample from the sample pickup station, a sample preparation station, and a sample transport for carrying said sample from the sample preparation station to the reaction cuvette. In preferred embodiments, the system also includes an antibody pickup station, an antibody probe for withdrawing an antibody from the antibody pickup station, an antibody preparation station, and an antibody transport for carrying the antibody from the antibody preparation station to the reaction cuvette.

IV. THE REAGENTS OF THE PRESENT INVENTION

The invention preferably employs the above-described immobilized support (especially a latex particle), a bidentate conjugate that contains an analyte member, and an anti-analyte antibody. Most preferably, the present invention uses the bidentate conjugate reagents described by Harris, P. C. et al. (U.S. Pat. No. 5,196,351). Such reagents contain two chemical members, separated by a spacer member. The first member is an analyte member. As used herein, an "analyte" is either the pharmacological agent which is to be detected, or an "analogous" agent. As used herein, an agent is "analogous" to a pharmacological agent if both agents can be bound to an antibody that is capable of binding the pharmacological agent.

The second member of the conjugate is most preferably biotin, and is capable of binding to avidin, streptavidin or an anti-biotin antibody. In the simplest embodiment, the analyte member of the present invention comprises a derivatized form of the preselected pharmacological agent itself (such as an acetaminophen-biotin derivative to be used in an assay for acetaminophen). Alternatively, the analyte member may comprise a metabolite or other compound whose structure is related to that of the preselected pharmacological agent. Thus, for example, in an immunoassay directed against cocaine, the analyte member may comprise a biotinylated derivative of the d, l, or d,l forms of cocaine, benzoylecgonine, ecgonine methyl ester, ecgonine, benzoylnorecgonine, norcocaine, etc. Similarly, either digoxin or its aglycone derivative, digoxigenin, may be conjugated to biotin in order to create a reagent that could be used in an immunoassay for digoxin. The present invention further provides methods for forming bidentate reagents suitable for detecting carbamazepine, primidone, theophylline, aminoglycoside antibiotics, vancomycin, quinidine, a cannabinoid, as well as other pharmacological agents

V. SYNTHESIS OF THE BIDENTATE REAGENTS OF THE PRESENT INVENTION

Many methods have been described in the art for linking together the members of a bifunctional conjugate through a spacer member. See, for example, U.S. Pat. No. 4,134,792, U.S. Pat. No. 4,238,565, and Green, N. M., Konieczny, L., Toms, E. J., and Valentine, R. C., The Use of Bifunctional Biotinyl Compounds to Determine the Arrangement of Subunits in Avidin, Biochem. J., 125, 781–791 (1971). These methods generally involve typical condensation, addition, and substitution reactions between chemical moieties which may or may not have been activated prior to such reactions.

As disclosed by Harris, P.C. et al. (U.S. Pat. No. 5,196,351), spacers of about 20 atoms are capable of tethering the members of the conjugate to one another without adversely effecting their respective capacities to bind to their binding partners. Longer or shorter spacers can, however be employed. The bidentate molecules described in U.S. Pat. No. 5,196,351, are formed by reacting a hydroxysuccinimide ester with an amine. Thus, for example, by reacting an N-hydrosuccinimide ester of biotin with an alkyl diamine (such as hexanediamine) derivative of the pharmacological agent of interest, a bidentate molecule can be formed in which the pharmacological agent of interest is linked to the biotin molecule via a 20 atom spacer. Use of alkylamidobiotin derivatives whose alkyl chain is longer or shorter than 20 carbon atoms permits one to modulate the length of the spacer.

The nature of the preferred spacer will depend upon the nature of the functional group(s) of the analyte member. Where the analyte member contains a carboxyl group, and it is desired to link the biotin member to this carboxyl group, the spacer is preferably formed using a alkyldiamine and an alkylamino acid. Thus, the carboxyl group of the analyte may be reacted with an amine group of the alkyldiamine (e.g., a hexane diamine), to form a peptide bond, and the unreacted amine group of the alkyldiamine reacted with the carboxyl group of the alkylamino acid (e.g., n-amino haxanoic acid) to form a second peptide bond. The resulting molecule thus contains a spacer having a free amino group (derived from the alkylamino acid). This group can be reacted with the carboxyl group of biotin to form the bidentate molecule.

Where the analyte member contains a hydroxyl group, and it is desired to link the biotin member to this hydroxyl group, the spacer is preferably formed using a alkyldiamine and a halogenated acid. Thus, the hydroxyl group of the analyte may be reacted with the halogen of the halogenated alkyl acid (e.g., 1-Bromo-n-pentanoic acid), to yield an alkylated adduct having a free carboxyl group. The carboxyl group of the adduct is reacted with an amine group of the alkyldiamine. The free amine of the alkyldiamine can then create the desired bidentate by forming a peptide bond with a carboxyl group of the biotin.

Where the analyte member contains an amine group, and it is desired to link the biotin member to this amine group, several preferred methods are available. A hexane diamine succinic anhydride spacer is preferred. The spacer length of the derivative may be modulated by using 2 hexane diamine derivatives in combination with an amino acid, or by using alkyldiamines of greater or lesser length. A preferred alkylamidobiotin derivative can be formed in four steps. Biotin is activated by incubation in anhydrous dimethylformamide (DMF) with 1,1'-carbonyldiimidazole (CDI) at elevated temperature (60–80° C.) and then cooled to ambient temperature. 1,6-hexanediamine (HD), dissolved in DMF, is then added to the activated biotin. After permitting the reaction to occur, the biotin-hexanediamine (BIOTIN-HD) product can be purified by column chromatography over silica gel. The side arm of biotin hexane amine can then be extended with succinic anhydride (SA) in pyridine to yield BIOTIN-HD-SA. The final step of the synthesis involves activation of the BIOTIN-HD-SA with CDI followed by the addition of 1,8-octanediamine (OD) and purification over silica gel of the desired BIOTIN-HD-SA-OD alkylamidobiotin derivative. In lieu of the above, the alkylamidobiotin derivative, caproamidobiotin may be employed. Where desired, the length of the spacer may be increased by bonding the free amine group of the above-described diamine to an amino acid having a desired length.

In an alternate embodiment, the spacer may be formed by reacting the amine group of the analyte with the carboxyl group of an amino acid (i.e. conducting the above reaction without either the diamine or the succinic anhydride).

The above-described methods may also be used where the analyte contains a isothiocyanate group, and the coupling of that group to the biotin member is desired.

Thus, the present invention provides alternative synthetic routes for producing the desired bidentate molecules. In accordance with the present invention, a first general method for forming such molecules entails converting a reactive amine of an analyte into an isothiocyanate group, and then condensing that group with an amine group of one of the above-described alkylamidobiotin derivatives.

Figure 3:
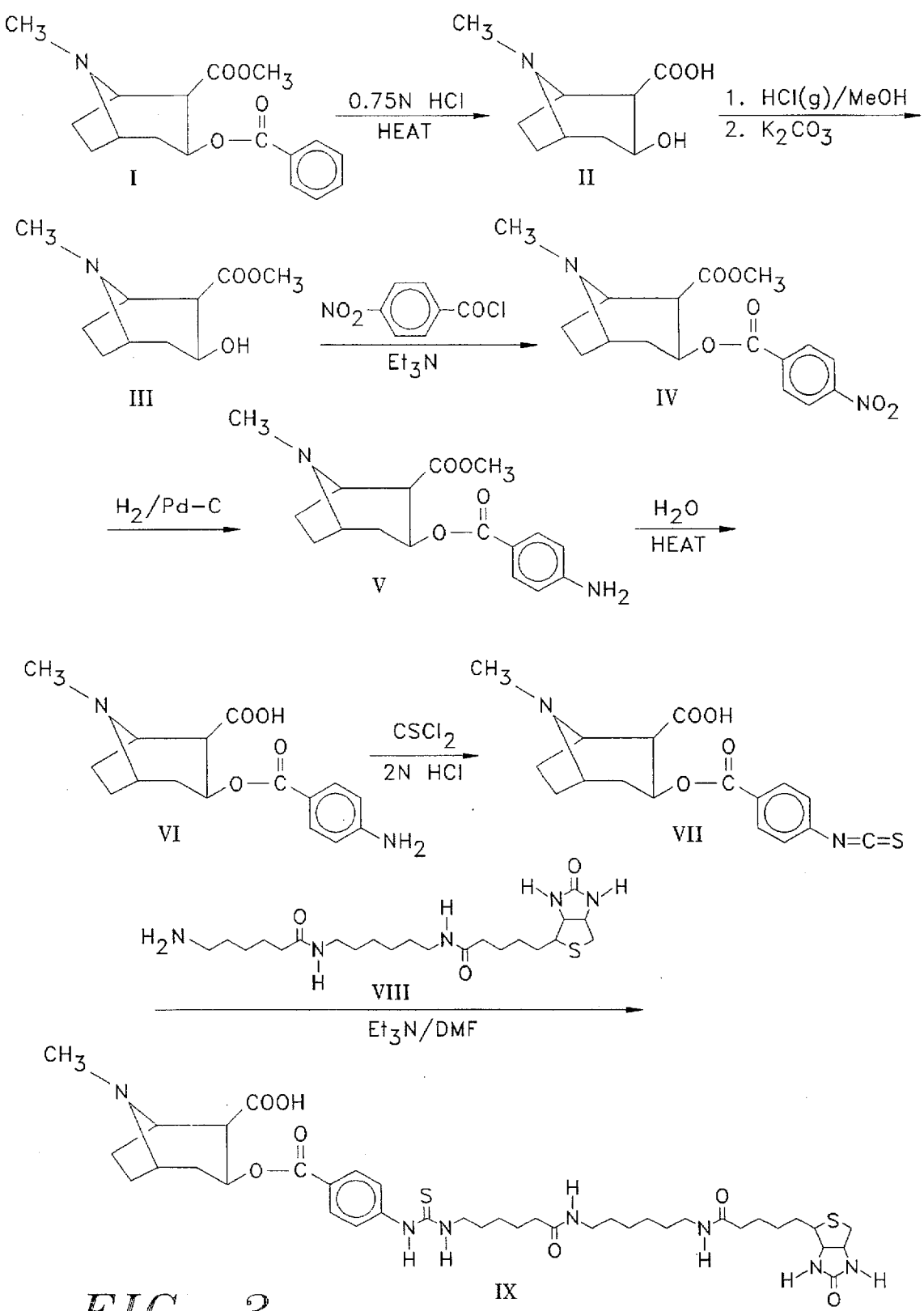
FIG. 3 shows a synthetic scheme for producing the benzoylecgonine-biotin reagent of the present invention.

In some situations, such as in the preparation of a benzoylecgonine-biotin derivative, the analyte may have multiple reactive groups. Preferably, such groups can be protected, for example, by conversion to an alkyl ester. This aspect of the invention is illustrated in FIG. 3 with respect to the preparation of a benzoylecgonine-biotin derivative.

In a preferred method of synthesizing such a derivative, cocaine (I) is hydrolyzed with acid (such as 0.75N HCl) and heat to form ecgonine (II). The newly formed carboxyl group of ecgonine is then reacted with acid and methanol to produce ecgonine methyl ester (III). Ecgonine methyl ester is then reacted with 4-nitrobenzoylchloride and triethylamine to yield 4-nitrobenzoylecgonine methyl ester (IV). The nitro group of the nitrobenzoate moiety is converted to an amine (V), as described above, using hydrogen and Pd—C. Once this is done, the methyl ester group is de-esterified, by reaction with water and heat, to yield 4-aminobenzoylecgonine (VI). Reaction with thiophosgene and acid (such as 2N HCl) converts the amine group into an isothiocyanate group, yielding benzoylecgonine isothiocyanate (VII).

The benzoylecgonine isothiocyanate (VII) can then be reacted directly with the alkylamidobiotin derivative (VII) to yield the desired benzoylecgonine-biotin bidentate conjugate.

In an alternative second general method, a suitable amine group of the analyte can be converted into a carboxyl group. Indeed, by appropriate selection of reagents, such chemistry can be used to convert related molecules into the desired analyte agent. In accordance with this embodiment of the present invention, an amine group of the analyte is reacted with an alkyl anhydride in the presence of an organic base, such as pyridine or a pyridine derivative. By selecting longer or shorter alkyl anhydrides, the spacer of the bidentate molecule can be modulated. A preferred alkyl anhydride is N-succinyl anhydride. The incubation reaction joins one of the anhydride's carbonyl carbons to the amine group of the analyte, and thereby forms an amidated derivative of the analyte that has a free carboxyl group. This carboxyl group can then be reacted with the amine of an alkylamidobiotin derivative to form the desired bidentate conjugate.

Figure 4:
FIG. 4 shows a synthetic scheme for producing the acetaminophen-biotin reagent of the present invention.
Figure 4:
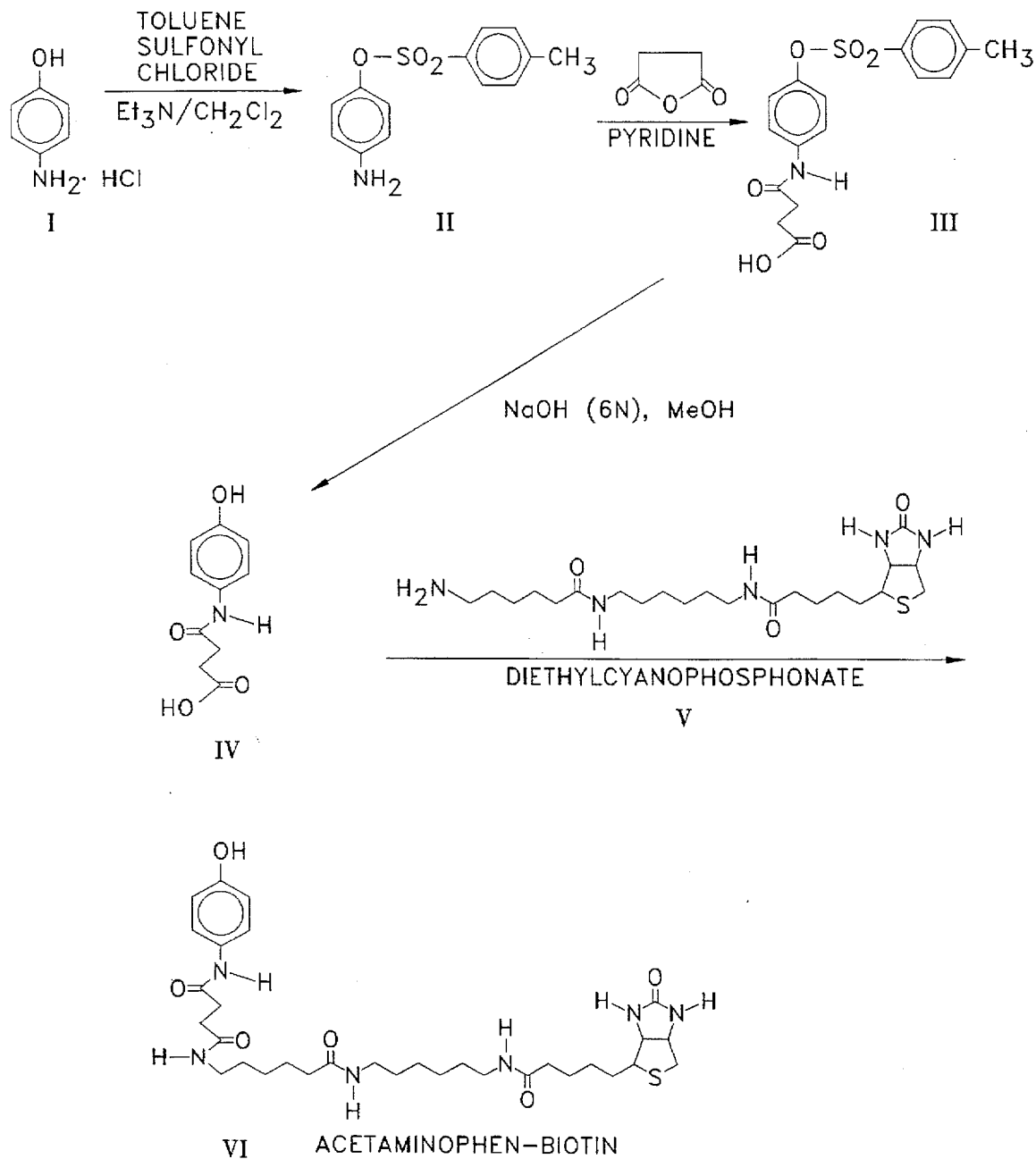

This aspect of the invention is illustrated in FIG. 4 with respect to the preparation of an acetaminophen-biotin derivative.

In a preferred method of synthesizing such a derivative, parahydroxyaniline (I), a compound that is structurally related to acetaminophen, is reacted with toluene sulfonyl chloride in the presence of triethylamine and methylene chloride. This reaction converts the hydroxyl group of the parahydroxyaniline into a sulfonyl toluene group (II). Reaction with succinic anhydride in the presence of pyridine results in a succinylation of the amine group of the aniline (III). The succinylated product is reacted with base (such as 6N NaOH) and methanol in order to remove the sulfonyl toluene group and restore the aromatic hydroxyl group (IV). The restored molecule can then be directly coupled to the amine of an alkylamidobiotin derivative to form the desired bidentate conjugate.

In a third alternative general method, a hydroxyl group of the analyte of interest is converted to an amine group in order form the bidentate molecule. Preferably, this can be accomplished by reacting the agent of interest in a methanolic solution of anhydrous ammonium acetate and sodium cyanoborohydride at ambient temperature in a nitrogen atmosphere. In some circumstances, as for example when the agent of interest contains reactive moieties, such as an ether or lactone ring, it is necessary to protect the reactive moiety prior to conducting the amination reaction.

In a preferred method of synthesizing such a derivative, digoxigenin (I), the aglycone derivative of digoxin, is prepared by hydrolyzing digoxin in ethanol and hydrochloric acid, followed by neutralization and recrystallization. Digoxigenin possesses three hydroxyl groups, however, amination of the molecule at carbon 3 is preferred. Digoxigenin also possesses a lactone ring moiety, and hence it is preferable to protect the ring prior to conducting the amination.

A preferred protection scheme entails reacting the digoxigenin with a metal oxide, such as platinum [IV] oxide monohydrate in the presence of hydrogen. This reaction hydrogenates the ether linkage of the lactone, thereby splitting the ring and forming a carboxylic acid derivative intermediate (II) of digoxigenin. This intermediate undergoes further hydrogenation to yield a gem diol derivative (III). The gem diol derivative (III) exists in a keto-enol equilibria with its keto form (IV), with the keto form being greatly preferred. The keto derivative (IV) and catalyst are then incubated in a digoxigenin-acetone solution with air and agitation. This reaction produces digoxigenone (V), which can be recrystallized using, for example, ethyl acetate.

At this stage, the lactone moiety has been protected, and the digoxigenone may be incubated in the methanolic solution of anhydrous ammonium acetate and sodium cyanoborohydride in order to aminate the 3 carbon of digoxigenone, thereby yielding 3-aminodigoxigenone (V). Treatment of 3-aminodigoxigenone (V) with alkaline reforms the ring, and thereby produces 3-aminodigoxigenin (VI).

Reaction of the 3-aminodigoxigenin with succinic anhydride in anhydrous pyridine gives the 3-amidosuccinic acid of digoxigenin after purification on silica gel. This compound can then be directly coupled to the amine of an alkylamidobiotin derivative to form the desired bidentate conjugate.

Having now generally described the invention, the same will be more readily understood through reference to the following examples which are provided by way of illustration, and are not intended to be limiting of the present invention, unless specified.

EXAMPLE 1
HOMOGENEOUS IMMUNOASSAY FOR DIGOXIN

The above-described digoxigenin-biotin bidentate was used to define a homogeneous immunoassay for digoxin. The immunoassay is based on the immunoprecipitin reaction and can be monitored by nephelometry or turbidimetry. The assay employs avidin, streptavidin, modified avidin or avidin preferably attached to carrier material (i.e., particles, macromolecules, colloidal metals, colloidal metal oxides). The details of the synthesis of the bidentate molecule and the immunoassay are described below.

Preparation of 3-Amidosuccinic Acid of Digoxigenin

Digoxin was hydrolyzed by refluxing in ethanol and hydrochloric acid for two hours. After neutralization and recrystallization the digoxigenin aglycone was obtained. Platinum (IV) oxide monohydrate and water were placed on a Parr reactor at 45 psi hydrogen for one hour then hydrogen was removed under vacuum. The catalyst was transferred to a digoxigenin-acetone solution and air was passed through the stirred solution until thin layer chromatographic ("TLC") analysis of the reaction indicated that the reaction was near completion. The catalyst was then removed and the digoxigenone was recrystallized from ethyl acetate.

A methanolic solution of anhydrous ammonium acetate was then combined with sodium cyanoborohydride and added to digoxigenone and stirred at ambient temperature overnight under a nitrogen atmosphere.

The reaction was evaporated to dryness and residue redissolved in 0.1M hydrochloric acid. After extraction with dichloromethane to remove impurities, the solution was made alkaline and extracted with dichloromethane to recover the 3-aminodigoxigenin.

Reaction of the 3-aminodigoxigenin with succinic anhydride in anhydrous pyridine gave the 3-amidosuccinic acid of digoxigenin after purification on silica gel.

Preparation of BIOTIN-HD-SA-OD

The BIOTIN-HD-SA-OD was prepared in four steps. Biotin was activated in anhydrous DMF with 1,1'-carbonyldiimidazole (CDI) at 70° C. for 30 minutes and cooled to ambient temperature. 1,6-Hexanediamine was dissolved in DMF, then added to the activated biotin; the mixture was then stirred overnight at ambient temperature. The biotin-hexane amine (BIOTIN-HD) was purified by column chromatography over silica gel. The side arm of the biotin-hexane amine was extended with succinic anhydride in pyridine and was then purified to give BIOTIN-HD-SA. The final step was activation of the BIOTIN-HD-SA with CDI followed by the addition of 1,1-octanediamine and purification over silica gel.

Preparation of DIG-NH-SA-OD-SA-HD-BIOTIN

The digoxigenin-3-amidosuccinic acid (DIG-NH-SA) was dissolved in anhydrous dimethyl formamide. N-hydroxysuccinamide and dicyclohexylcarbodiimide were then added, and the solution was stirred for three hours at ambient temperature. A thin layer chromatograph of the mixture indicated that the starting material had disappeared and that a new spot had appeared at higher relative migration value ("Rf value," i.e., the ratio of the migration of a particular species relative to the total distance traversed by the chromatography solvent). BIOTIN-HD-SA-OD was added to the reaction mixture and stirred overnight at ambient temperature. The reaction was evaporated to dryness; the residue washed with methanol and column chromatographed to give the bidentate, DIG-NH-SA-OD-SA-HD-BIOTIN.

Preparation of DIG-NH-SA-OD-SA-HD-BIOTIN-AVIDIN

Avidin was dissolved at 10 mg /ml in 0.1M phosphate buffer pH 7.4 which was then made 10 mM in HABA [2(4-hydroxyphenyl-azo)benzoic acid]. The solution turned a yellow-pink. a 5.0 mg /ml DIG-NH-SA-OD-SA-HD-Biotin stock solution was prepared in DMF, and 50 µl aliquots were added to the avidin-HABA solution. The addition was done dropwise, with mixing between drops until the solution became light yellow. The solution was then permitted to stand for one hour. The reaction mixture was then transferred to 6.4 mm dialysis tubing having a 12–14,000 MW cutoff using 0.2 ml of citrate buffered saline (CBS) pH 6.0. Dialysis was performed at 4° C. in CBS pH 6.0, 250 ml, with 6 changes of dialysate in three days.

Reaction solutions were recovered and quantitated by UV spectra at 280 nm (1 mg /ml Avidin has a 280 nm absorbance of approximately 1.45). The results indicated that the recovered material had an avidin concentration of 7.5 mg /ml.

The titer of the digoxigenin-biotin conjugate and antibody was assessed using an ICS II™ M33 card. The M33 card is a gain-setting adjustor that is included with the ICSIITM analyzer. Substantially equivalent results can be obtained using the ARRAY analyzer, or with other similar apparati. The assay protocol was as follows, and the results are shown in Table 1:

ICS™ Buffer: 600 µl

Antibody: 42 µl (1/10, 1/15, or 1/20 in CBS or ICS™ buffer)

Sample: 42 µl (in CBS or ICS™ buffer)

Conjugate: 42 µl

TABLE 1

| Avidin Conc. (mg/ml) | Rate Units Antibody dilution | | |
|---|---|---|---|
| | 1/10 | 1/15 | 1/20 |
| 0.250 | 1620 | 817 | 576 |
| 0.200 | 1550 | 731 | 492 |
| 0.150 | 1550 | 708 | 420 |
| 0.125 | 1480 | 734 | 397 |
| 0.100 | 1330 | 668 | 384 |
| 0.075 | 1060 | 657 | 332 |
| 0.050 | 650 | 463 | 287 |
| 0.013 | 347 | 115 | 357 |

In order to further calibrate the assay, a standard curve was developed using 0.10 mg /ml of conjugate and a 1/10 dilution of antibody. For such calibration, a digoxin standard solution of 10 mg /ml was prepared in DMF containing 8% BSA. The standard was diluted to 1000, 100, 10, 1.0, 0.1 µg/ml in dimethyl formamide that was 8% bovine serum albumin ("BSA"). The assay was done in duplicate. The assay conditions (using an ICS II™, M33 card) were:

ICS™ Buffer: 600 µl

Antibody: 42 µl (1/10 in ICS™ buffer)

Sample: 42 µl (1/20 in ICS™ buffer)

Conjugate: 42 µl (at 0.10 mg/ml)

The results of the assay are shown in Table 2.

TABLE 2

| Digoxin Conc. (µg/ml) | Rate Units | |
| --- | --- | --- |
| 1000 | 158 | 131 |
| 100 | 157 | 141 |
| 10 | 678 | 678 |
| 1.0 | 1320 | 1320 |
| 0.1 | 1320 | 1320 |
| 0.0 | 1385 | 1395 |

EXAMPLE 2

LATEX PARTICLE-ENHANCED HOMOGENEOUS IMMUNOASSAY FOR DIGOXIN

The reagents and immunoassays described in Example 1 can be modified to produce a highly sensitive latex particle-enhanced homogeneous digoxin assay.

An initial step in such an assay is the formation of the latex-avidin particle. Suitable particles were obtained using either of the following methods:

Method A 1. 3.5 ml of MOPS buffer (0.1M, pH 6.0), 0.28 ml of 10% Tween-20 and 0.64 ml of carboxylate modified latex ("CML"), 38 nm in diameter, 10% solid solution from Duke Scientific) were combined in a 50 ml Erlenmeyer flask.

2. 44 mg of N-hydroxysuccinimide (NHS) in 0.86 ml of MOPS buffer (0.1M, pH 6.0) and 30 mg of 1-ethyl-3-(3-dimethylaminopropyl) carbodiimide (EDAC) in 0.8 ml of MOPS buffer (0.1M, pH 6.0), were added to the reaction, and stirred for an hour at approximately 40° C.

3. The pH was measured, and then adjusted to approximately 8.0 with 3N NaOH.

4. An avidin solution was prepared by mixing 11 mg of avidin in 16 ml of MOPS buffer (20 mM, pH 8.0). The solution was added to the reaction, and the reaction was then stirred for five hours at 4° C.

5. The pH was then re-measured, and BSA was added to a final concentration of 2 mg /ml BSA.

6. The resulting preparations of latex-avidin were purified from other reactants using tube dialysis (conducted at 4° C., 3 changes, 100×volume dialysis tubing MWCO 12–14,000, equilibrated with 20 mM TRIS buffer pH 9.0, 0.2% Tween-20 and 0.09% sodium azide.

7. After purification and concentration back to original volume, 200 mg BSA was added to make the solution 2 mg /ml in BSA. The reaction was allowed to mix at room temperature for one hour or until the BSA completely dissolved.

8. The container of latex reagent was completely sealed and incubated for 3 days (72 hours) in a 45° C. oven.

9. After incubation, the reagent was removed from the oven, cooled to room temperature, and adjusted to a pH of approximately 7.0. 120 µl of a solution of 2-(4-hydroxyphenylazo)benzoic acid (HABA), 10 mM in PBS, pH 7.4 ("HABA solution") was added, turning the solution orange-yellow in color.

The desired digoxin-biotin bidentate-avidin complex was prepared by weighing out 2 mg of digoxin-biotin reagent, and dissolving the material in 1 ml of dimethyl formamide. 300 µl of the biotin analyte (2 mg /ml solution) was combined with 100 µl of DMF and 600 µl of Tris buffer (20 mM TRIS, pH 7.0, 0.2% Tween-20, 0.01% sodium azide). The final solution had a digoxin-biotin concentration of 600 µg/ml.

The orange-yellow solution was titrated with the digoxin-biotin solution. This was done by adding 100 µl aliquots until the solution turned light yellow, then 10% excess was added, totalling approximately 400 µl. The reactants were allowed to stir for approximately 30 minutes at room temperature.

Unbound reactants were removed by dialysis using 25 mm dialysis tubing having a molecular weight cut off of 12–14 kd (Baxter). Dialysis was against 20 mM Tris, pH 9.0, 0.2% Tween-20, and 0.01% sodium azide. Dialysis was conducted at 40° C. and used 4 changes of buffer (approximately 10 liters each).

Method B (used for the immunoassays of Examples 8–12)

1. 19.5 ml of D.l. water, 6.0 ml of MOPS buffer (0.1M, pH 6.0), 1.5 ml of 10% Tween-20 and 3.0 ml of carboxylate modified latex (CML, 60 nm in diameter, 10% solid solution from Seradyn Inc.) were combined in a 200 ml Erlenmeyer flask, and mixed slowly at room temperature for approximately 5 min.

2. 199 mg of N-hydroxysuccinimide (NHS) and 148 mg of 1-ethyl-3-(3-dimethylaminopropyl)carbodiimide (EDAC), were added to the reaction, and stirred for an hour at approximately 4° C.

3. The pH was measured, and then adjusted to approximately 9.0±0.1 with 1N NaOH.

4. An avidin solution was prepared by mixing 75 mg of avidin, 3.4 ml of 10% Tween-20 and 67.5 ml of MOPS buffer (20 mM, pH 9.0). The solution was added to the reaction, and the reaction was then stirred for five hours at 4° C.

5. The pH was then re-measured, 200 mg of BSA was added, and the reactants were permitted to mix at 40° C. overnight.

The resulting preparations of latex-avidin were purified from other reactants using either of two methods, depending on the volume.

a. for small scale preparations, tube dialysis (conducted at 4° C., 3 changes, 100×volume dialysis tubing MWCO 12–14,000) was used in conjunction with a Sepharose CL-6B sizing column (equilibrated with 20 mM TRIS buffer pH 9.0, 0.2% Tween-20 and 0.09% sodium azide.

b. for larger scale preparations, the Pellicon Cassette system (PCS) and membrane MWCO 300K were employed.

7. After purification and concentration back to original volume, 200 mg BSA was added to make the solution 2 mg/ml in BSA. The reaction was allowed to mix at room temperature for one hour or until the BSA completely dissolved.

8. The container of latex reagent was completely sealed and incubated for 3 days (72 hours) in a 45° C. oven.

9. After incubation, the reagent was removed from the oven, cooled to room temperature, and adjusted to a pH of approximately 7.0. 200 µl of a solution of 2-(4-hydroxyphenylazo)benzoic acid (HABA), 10 mM in PBS, pH 7.4 ("HABA solution") was added, turning the solution orange-yellow in color.

The desired digoxin-biotin bidentate-avidin complex was prepared by weighing out 3 mg of digoxin-biotin reagent, and dissolving the material in 5 ml of a 40:60 mixture of dimethyl formamide: 20 mM TRIS, pH 7.0. The final solution had a digoxin-biotin concentration of 600 µg/ml.

The orange-yellow solution was titrated with the digoxin-biotin solution. This was done by adding 50 µl aliquots until the solution turned light yellow, then 10% excess was added, totalling approximately 500 µl. The reactants were allowed to stir for approximately 30 minutes at room temperature.

Unbound reactants were removed by dialysis using 25 mm dialysis tubing having a molecular weight cut off of 12–14 kd (Baxter Travenol, Inc.). Dialysis was against 20 mM Tris, pH 9.0, 0.2% Tween-20 , and 0.9% sodium azide. Dialysis was conducted at 4° C. used 4 changes of buffer (approximately 10 liters each.

The above-described reagent was used in a latex particle-enhanced homogeneous digoxin assay (Table 3). The assay exhibited high sensitivity and throughput, while reducing the amount of antiserum required. The method also eliminated or reduced matrix problems and was particularly amenable to automated processing.

TABLE 3

| Digoxin Conc. (ng/ml) | Rate Units | B/B₀ |
|---|---|---|
| 0 | 2971 | 100 |
| 0.5 | 2633 | 89 |
| 1 | 2380 | 80 |
| 2 | 1850 | 62 |
| 3 | 1472 | 50 |
| 4 | 1168 | 39 |
| 5 | 929 | 31 |
| 10 | 280 | 8 |

EXAMPLE 3

HOMOGENEOUS IMMUNOASSAY FOR COCAINE

As indicated, benzoylecgonine is a major metabolite of cocaine in urine, and its chemical structure is related to cocaine (FIG. 3). An immunoassay was developed using the benzoylecgonine-biotin bidentate described above. The details of the synthesis of this molecule and the immunoassay are described below.

I. Benzoylecgonine-Biotin Bidentate (IX, FIG. 3)

A. Outline of Preparation (FIG. 3)

1. Acid hydrolysis of cocaine (I) to ecgonine (II)
2. Conversion of ecgonine (II) to ecogonine methyl ester (III) by esterification
3. Reaction of (III) with p-nitrobenzoylchloride to give cocaine with a nitro group at the para position of the aromatic ring (IV)
4. Hydrogenation of (IV) to yield the aminococaine derivative (V)
5. Hydrolysis of (V) to afford the aminobenzoylecgonine derivative (VI)
6. Treatment of (VI) with thiophosgene to afford the benzoylecgonine isothiocyanate (VII)
7. Reaction of the alkyloamidobiotin (VIII) with (VII) to give the desired benzoylecgonine-biotin bidentate derivative (IX) (TLC: Rf≈0.07 in 1:1 MeOH/CHCl₃)

B. Test of immunoreactivity of Benzoylecgonine-Biotin Bidentate (IX)

The novel benzoylecgonine-biotin bidentate compound described above can be used in a homogeneous immunoassay for the screening of cocaine and benzoylecgonine in urine samples. The immunopotency of the benzoylecgonine-biotin (IX) was assessed with the EMIT® cocaine metabolite kit reagents as described below.

1. Solutions of the benzoylecgonine-biotin bidentate(x) were prepared at 500, 100, 10 and 1 µg/ml in the EMIT® buffer as described by the manufacturer
2. The prepared samples were then assayed as unknowns with the EMIT® reagents, and the results are shown Table 4.

TABLE 4

| Target Conc. of VI by WT (µg/ml) | Observed Conc. by EMIT® (µg/ml) | % Observed/Target |
|---|---|---|
| 500 | >3 | — |
| 100 | >3 | — |
| 10 | >3 | — |
| 1 | ≈3 | 300 |

The above EMIT® results indicated that the benzoylecgonine-biotin bidentate was immunoreactive.

II Latex-Avidin Preparation

Avidin was conjugated to latex to form an avidin-latex conjugate for use in the immunoassay. Thus, to 4.65 ml of MOPS buffer (0.1M) containing 0.59% Tween-20 were added a suspension of 0.62 ml of 38-nm size latex particles obtained from Duke Scientifics, a solution of 41 mg of N-hydroxysuccimide in 0.66 ml of cold MOPS, and a solution of 28.8 mg water soluble carbodiimide in 0.63 ml of cold MOPS. After gentle stirring for one hour at 4° C., the latex reaction mixture was raised to pH 9, and allowed to react with 9 mg of avidin in 15 ml of borate buffer (0.02M, pH 9) at 4° C. for another five hours. Bovine serum albumin (BSA; 44 mg ) was added, and stirring was continued at ambient temperatures for one hour after which the latex-avidin mixture was dialyzed overnight against 0.02 M TRIS containing 0.2% Tween-20 at pH 8 or pH 9. The latex-avidin was then purified on a Sepharose CL-6B column using the TRIS dialysis buffer as the eluent. The U.V. spectrum of fraction pools of the two lots of latex-avidin were substantially identical, and evidenced a substantial adsorption peak at approximately 230 nm.

After the UV spectra was taken, BSA was added to the latex-avidin to a final concentration of 0.2% and the resulting material was heat-stressed at 45° C. for 3 days before coupling to the above-described benzoylecgonine-biotin bidentate.

III. Latex-Avidin-Biotin-Benzoylecgonine Conjugate

A. Preparation of the Conjugate

The latex-avidin-biotin-benzoylecgonine conjugate was prepared by adding a small volume of 5 mM HABA (2(4-hydroxyphenyl-azo)benzoic acid) in phosphate buffer to a suspension of 15 ml of the latex-avidin prepared at pH 8, and adjusting the suspension to pH 7. The HABA bound to the avidin and turned the color of the solution from colorless to pink. A solution containing 7.5 mg /ml of the benzoylecgonine-biotin bidentate (VI) in methanol was then added dropwise to the avidin solution until the pink color disappeared when complete displacement of HABA from avidin by the bidentate was indicated. The amount of the bidentate added was 0.68 mg. The reaction mixture was let stand for one hour at room temperature, and elution with 0.02M TRIS containing 0.2% Tween-20 at pH 8 on a Sepharose CL-6B column yielded the latex-avidin-biotin-benzoylecgonine conjugate. The conjugate was scanned from 200 nm to 500 nm on the Beckman DU-70 spectrometer, and found to have a single peak of adsorption at approximately 230 nm.

Latex-avidin-biotin-benzoylecgonine conjugate was also prepared from the latex-avidin prepared at pH 9, with the exception that the pH of the TRIS buffer used in both the latex-avidin and the conjugate steps was 9 instead of 8. The conjugate was scanned from 200 nm to 500 nm on the Beckman DU-70 spectrometer, and found to have a single peak of adsorption at approximately 230 nm, however, a substantial shoulder at 260 nm was also detected.

B. Test of Immunoreactivity on ICS II™

The immunoreactivity of the benzoylecgonine-biotin-avidin conjugate lot prepared at pH 9 was assessed using an ICS II™ utilizing an antibody obtained from BiosPacific. The assay protocol was as follows Gain: 3

RATX: 10

ICS™ Buffer: 600 µl

Antibody: 42 µl (1/50 dilution in ICS™ buffer)

Sample: 42 µl (1/6 dilution in ICS™ buffer)

Conjugate: 42 µl (neat, 1/2 or 1/3 dilution in ICS™ buffer)

The results are shown in Table 5

TABLE 5

| EMIT® | Latex Conjugate Titer | | | | | |
|---|---|---|---|---|---|---|
| Stds | 1/2 | | 1/3 | | Neat | |
| (µg/ml) | Rate | % B/B$_0$ | Rate | % B/B$_0$ | Rate | % B/B$_0$ |
| 0 | 772 | 100 | 414 | 100 | 1710 | 100 |
| 0.3 | 636 | 83.4 | — | — | 1550 | 90.6 |
| 3 | 243 | 33.7 | — | — | — | — |

The above ICS™ results indicated that: (a) the latex-benzoylecgonine-biotin-avidin conjugate exhibited good immunoreactivity and dose response for benzoylecgonine when paired the antibody from Biodesign, Inc., and (b) the dose response of the standard curve was acceptable for a screening test for benzoylecgonine in urine.

IV. Application of Benzoylecgonine-Biotin-Avidin-Latex Conjugate to Screening of Benzoylecgonine in Urine Sample The benzoylecgonine-biotin-avidin and antibody reagents were optimized on an ARRAY 360 analyzer using benzoylecgonine standards prepared in urine. After optimization, the reagents and the standards were applied to the screening of benzoylecgonine in urine samples on the ARRAY and the results were compared to those obtained by GC/MS. The assay buffers and reagents, the assay protocol, the ARRAY dose-response curve, and the correlation result with GC/MS are shown below. The ARRAY dose response curve is shown in Table 6.

Buffers and Reagents a. Benzoylecgonine-biotin bidentate-avidin conjugate in TRIS buffer (0.02M, 0.2% BSA, pH 9.0)

b. Benzoylecgonine antibody obtained from BiosPacific in Antibody Diluent (Beckman P/N 668,579)

c. ICS™ buffer (Beckman Instruments, ICS™ Reagent) as the assay buffer

ARRAY Assay Protocol No.: 24, RATX=10

Buffer: 500 µl

Antibody: 43.5 µl (1.75.5 dilution)

Sample: 100 µ(at 1/6 on-line dilution)

Conjugate: 42 µl (1/3 dilution)(Trigger reagent)

TABLE 6

| Standard (µg/ml) | Rate Unit | % B/B$_0$ |
|---|---|---|
| 0 | 1075 | 100 |
| 0.15 | 888 | 82.6 |
| 0.3 | 777 | 72.3 |
| 1 | 469 | 43.6 |
| 2 | 267 | 24.8 |

TABLE 6-continued

| Standard (µg/ml) | Rate Unit | % B/B$_0$ |
|---|---|---|
| 3 | 185 | 17.2 |

Correlation vs GC/MS

To test the validity of the immunoassay, the assay was run on 85 urine samples that had been found by GC/MS to be benzoylecgonine positive. The results of this test are shown in Table 7.

TABLE 7

| N = 85 | GC/MS + |
|---|---|
| ARRAY CUT-OFF 0.15 µg/ml (888 Rate Units) + | 84 |
| − | 1 |

As indicated by Table 7, a good correlation with GC/MS was obtained using the above immunoassay. Using an ARRAY cut-off value of 0.15 µg/ml, the benzoylecgonine bidentate method resulted in only one false negative out of 85 GC/MS positive samples, or a predictive power of 98.8%. Thus, the benzoylecgonine bidentate reagents offer a simple, rapid and reliable homogeneous assay for the screening of benzoylecgonine in urine samples.

To further test the validity of the assay, 17 urine samples donated by volunteers were tested. All 17 urine samples were shown to be negative using the benzoylecgonine bidentate method.

EXAMPLE 4

LATEX PARTICLE-ENHANCED HOMOGENEOUS IMMUNOASSAY FOR COCAINE

An immunoassay for cocaine was also conducted using a latex-avidin conjugate produced via an alternate synthetic method.

In the alternative method for forming the avidin-latex conjugate, 3.5 ml of MOPS buffer (0.1M, pH 6.0) was combined with 0.28 ml of 10% Tween-20, and 0.64 ml of carboxylate modified latex (CML, 60 nm in diameter, 10% solid solution from Seradyn, Inc.) in a 50-ml Erlenmeyer flask.

0.86 ml of a freshly prepared N-hydroxysuccinimide-MOPS solution (containing 44 mg of N-hydroxysuccinimide (NHS) in 0.86 ml of 0.1M, pH 6.0 MOPS) was added to the flask along with 0.8 ml of a freshly prepared 1-ethyl-3-(3-dimethylaminopropyl) carbodiimide (EDC)-MOPS solution (30 mg EDC in 0.8 ml of MOPS, 0.1M, pH 6.0). The solution was stirred for one hour at approximately 4° C.).

After such incubation, the pH was adjusted to approximately 8.0 with 3N NaOH. Avidin solution (6 mg in 16 ml of MOPS, 20 mM, pH 8.0) was added and the mixture was allowed to stir for five additional hours at approximately 4° C.).

BSA was then added to the solution to a final concentration of 2 mg/ml.

To purify the latex-avidin conjugate thus formed, the solution was transferred to 100×volume dialysis tubing having a molecular weight cut-off of 12–14,000, and dialyzed at 4° C. against 20 mM TRIS, pH 9.0, 0.2% Tween-20 and 0.01% NaN₃. The dialysate was changed 3 times.

The dialyzed material was then sieved with a 200 ml Sepharose CL-6B sizing column, equilibrated and eluted with 20 mM TRIS, pH 9.0, 0.2% Tween-20 and 0.01% NaN₃.

After purification and reconstitution back to its original volume, BSA was added to the solution to a final concentration of 2 mg /ml. The resulting solution was stored in a 45° C. oven for 72 hours.

After removal from the oven, and cooling to room temperature, the pH of the solution was adjusted to approximate neutrality, followed by the addition of 120 µl of HABA solution (2-(4-hydroxyphenylazo)benzoic acid, 10 mM in PBS, pH 7.4) to turn the solution orange-yellow.

To prepare the cocaine-biotin solution, 2 mg of cocaine-biotin was dissolved in 1 ml of DMF, and 300 µl of the solution was mixed with 100 µl DMF and 600 µl TRIS. The final solution has a cocaine-biotin concentration of 600 µg/ml in a 40/60 mixture of DMF/TRIS buffer.

The orange-yellow avidin-HABA solution described above was titrated with 100 µl aliquots of the cocaine-biotin solution until it turned light yellow. A 10% excess of cocaine-biotin was then added, bringing the final volume to 400 µl. The mixture was stirred for approximately 30 minutes at room temperature.

The final step in the preparation of the reagent entailed dialysis, and used 25 mm dialysis tubing (Baxter) having a molecular weight cut-off of 12–14,000. Dialysis was conducted at 4° C. against 3 liters of 20 mM TRIS 20 mM, pH 9.0, 0.2% Tween-20, and 0.01% NaN₃. The dialysate was changed 4 times, each time using 3 liters.

The latex-avidin conjugate could be used in the place of avidin in the immunoassay formats described herein. The presence of the latex co-conjugate increased assay sensitivity, reduced the amount of antiserum used, and reduced (or eliminated) matrix problems. Moreover, no sample pretreatment was needed and the assay could be readily automated.

EXAMPLE 5

HOMOGENEOUS IMMUNOASSAY FOR ACETAMINOPHEN

The above-described acetaminophen-biotin bidentate compound was synthesized and successfully used in a homogeneous immunoassay of acetaminophen (FIG. 4) in serum samples. The details of the synthetic method, and assay protocols are described below.

I. Acetaminophen-Biotin Bidentate (VI, FIG. 4)

A. Outline of Preparation (FIG. 4)

1. Protection of the OH group of p-hydroxyanline (I) with p-toluenesulfonyl group to give (II).
2. Succinylation of the amino group in (II) with succinic anhydride in pyridine to give (III).
3. Removal of the p-toluenesulfonyl group in (III) with NaOH/MeOH to yield (IV).
4. Coupling of (IV) to the alkyloamidobiotin (V) with diethylcyanophosphonate to give the desired acetaminophen-biotin bidentate (VI) (m.p. 180° C., dec) (TLC Rf≈0.25 in EtOAc/MeCOH/CH₃Cl/ NH₄OH≈3:3:1:0.6)

B. Test of immunoreactivity of Acetaminophen-Biotin Bidentate

The immunopotency of the acetaminophen-biotin (VI) was assessed with the EMIT® acetaminophen kit reagents as follows.

1. Solutions of the acetaminophen-biotin bidentate (VI) were prepared at 1100, 550, 370 and 220 µg/ml in the EMIT® buffer
2. The samples were then assayed as unknowns with the EMIT® reagents. The results are shown in Table 8.

TABLE 8

| Target Conc. of (VI) by Wt (µg/ml) | Observed Concentration by EMIT ® (µg/ml) | % Observed/Target |
|---|---|---|
| 1100 | 20.2 | 1.8 |
| 550 | 10.8 | 2.0 |
| 370 | 6.6 | 1.8 |
| 220 | 3.95 | 1.8 |

The EMIT® results in Table 8 indicated that the acetaminophen-biotin bidentate was immunoreactive.

II. Acetaminophen-Biotin-Avidin Conjugate

The acetaminophen-biotin-avidin conjugate was prepared by adding a few drops of 10 mM HABA (2(4-hydroxyphenylazo)benzoic acid) in phosphate buffer to a solution of avidin in 0.1M phosphate buffer (pH 7.4), as described above. The HABA bound to the avidin and turned the color of the solution from colorless to yellow-pink. A solution containing the acetaminophen-biotin bidentate (VI) in methanol was then added dropwise to the avidin solution until the pink color disappeared when complete displacement of HABA from avidin by the bidentate was indicated. The reaction mixture was let stand for one hour and then dialyzed extensively with the conjugate buffer (citrate buffered saline at pH 6.0) at 4° C. to give the conjugate concentrate, as described above.

The concentrate was diluted 1:10 with the citrate buffered saline and the resulting solution was scanned from 340 nm to 240 nm on a Beckman DU-70 spectrometer. The conjugate was found to adsorb in a broad peak at 280 nm, whose leading edge troughed at approximately 80% of the peak value at a wavelength of approximately 255 nm. adsorption rose sharply at wavelengths below 250 nm. The concentration of the conjugate concentrate was expressed in $A_{280}$ units, which was determined by the absorbance at peak maximum near 280 nm (conjugate at 1/10 dilution=1.184 $A_{280}$ units) to be 11.84 $A_{280}$ units. The conjugate concentrate was then diluted with the citrate buffered saline to an appropriate working concentration for assays.

The immunoreactivity of the above-described acetaminophen-biotin-avidin conjugate was assessed on a ICS II™ analyzer utilizing two antibodies obtained from Biodesign, Inc. The assay protocol was:

Buffer: 600 µl

Antibody: 42 µl (1/20 and 1/10 dilutions in ICS™ Buffer)

Sample: 42 µl (1/6 dilution in ICS™ Buffer)

Conjugate: 42 µl (concentration=0.58 $A_{280}$ units)

The results of the assay are shown in Table 9.

TABLE 9

| EMIT ® Stds | Sheep Antibody Rate Unit & % B/B₀ | | | | Rabbit Antibody Rate Unit |
|---|---|---|---|---|---|
| (µg/ml) | 1/10 | % B/B₀ | 1/20 | % B/B₀ | 1/10 |
| 0 | 4960 | 100 | 2980 | 100 | 859 |
| 10 | 4370 | 88.1 | 2760 | 92.6 | |
| 25 | 3550 | 71.6 | 2270 | 76.2 | 849 |

TABLE 9-continued

| EMIT® Stds (μg/ml) | Sheep Antibody Rate Unit & % B/B₀ | | | | Rabbit Antibody Rate Unit |
|---|---|---|---|---|---|
| | 1/10 | % B/B₀ | 1/20 | % B/B₀ | 1/10 |
| 50 | 3070 | 61.9 | 1840 | 61.7 | |
| 100 | 2300 | 46.4 | 1490 | 50.0 | |
| 200 | 1640 | 33.1 | 1270 | 42.6 | |

The results in Table 9 indicated that (a) the acetaminophen-biotin-avidin conjugate exhibited good immunoreactivity and dose response when paired with the sheep antibody (lot 339) from Biodesign, Inc., and (b) the dose response of the standard curve was acceptable for quantitation of acetaminophen.

III. Application of Acetaminophen-Biotin-Avidin Conjugate to Quantitation of Acetaminophen in Serum Samples The acetaminophen-biotin-avidin and antibody reagents were optimized on the ARRAY 360 and with the use of acetaminophen standards prepared in normal human serum. After optimization, the reagents and the standards were applied to the quantitation of acetaminophen in serum samples on the ARRAY and the results were compared to those obtained by TDx®. Summarized below are the assay buffers/reagents, the ARRAY assay protocol, the ARRAY dose-response curve and the correlation result with TDX®.

Buffers and Reagents

1. Acetaminophen-biotin bidentate-avidin conjugate in ICS™ Drug Conjugate Diluent (Beckman P/N 663, 574)
2. Acetaminophen antibody obtained from Biodesign, Inc. in ICS™ Antibody Diluent (Beckman P/N 663,579)
3. ICS™ buffer (Beckman P/N 662,612) as the assay buffer ARRAY Assay Protocol No.: 27

Buffer: 621 μl

Antibody: 43.5 μl (1/20 dilution)

Sample: 21 μl (at 1/12 on-line dilution)

Conjugate: 42 μl (concentration=0.145 $A_{280}$ units) (Trigger reagent)

The results of the above-described dose response assay is shown in Table 10.

TABLE 10

| Standard (μg/ml) | Rate Unit | % B/B₀ |
|---|---|---|
| 0 | 2665 | 100 |
| 10 | 2240 | 84.1 |
| 20 | 1965 | 73.7 |
| 50 | 1505 | 56.5 |
| 100 | 1125 | 42.2 |
| 200 | 802 | 30.1 |

A correlation of the assay with TDX® was made. The correlation revealed that the assay results were linearly proportional to those obtained by TDx®. The relationship calculated was:

ARRAY=1.0043*TDX®+1.3(N=25)

where:

0.99

ARRAY (Mean)=35.5 μg/ml

TDX® (Mean)=34.0 μg/ml

The results indicated that the assay could be used to quantitatively determine the concentration of acetaminophen in a sample.

EXAMPLE 6

LATEX PARTICLE-ENHANCED HOMOGENEOUS IMMUNOASSAY FOR ACETAMINOPHEN

The above-described acetaminophen-biotin bidentate was used in a 2-reagent latex particle-enhanced homogeneous immunoassay. For such use, the bidentate was conjugated to latex-avidin in the following manner.

A suspension containing 8.75 ml of 0.1M MOPS (pH 6.0), 0.55 ml of 0.1M MOPS with 10% Tween-20 (pH 6) and 1.25 ml (approximately 125 mg) of carboxylated latex (60 nm in diameter) was prepared. After cooling the suspension to 4° C. and with stirring, a solution of 82 mg of N-hydroxysuccinimide in 1.31 ml of cold 0.1M MOPS (pH 6) and a solution of 57.5 mg of water soluble carbodiimide in 1.25 ml of cold 0.1M MOPS (pH 6) were introduced.

The resulting mixture was then adjusted to pH 5.5–6, and stirred for approximately 1 hour at about 4° C., raised to pH 9, and allowed to react with 18 mg of avidin in 30 ml of cold 0.02M borate buffer (pH 9) at 4° C. for another 5 hours. BSA (88 mg) was added and stirring was continued overnight at 4° C. after which the latex-avidin mixture was dialyzed against 3 changes of 0.02M Tris (pH 9) containing 0.2% Tween-20 for 1.5 days. The resulting latex-avidin was purified on sepharose CL-6B columns using the Tris dialysis buffer as the eluent. The materials were subsequently heat stressed at 45° C. for 3 days. The materials had an A500 of between 0.41 and 0.46, and had an A600 of between 0.19 and 0.21.

To form the latex-avidin-acetaminophen conjugate, 30 μl of 10 mM HABA (2(4-hydroxyphenyl-azo)benzoic acid) in 0.1M phosphate buffer (pH 7.4) was added to a latex-avidin suspension.

The HABA bound to the avidin and turned the color of the suspension slightly pinkish. The color change was only barely visible. A solution containing 6.5 mg /ml of the acetaminophen bidentate in methanol was then added dropwise to the latex-avidin solution after which the pink color disappeared. The amount of bidentate added was 0.455 mg or 70 μl. The reaction was let stand for 1 hour at room temperature, and eluted with 0.02M Tris containing 0.2% Tween-20 at pH 9 on a Sepharose CL6B column to yield 25 ml of the latex-avidin-acetaminophen bidentate conjugate. The conjugate exhibited absorbencies of 0.3333 and 0.1726 at 500 and 600 nm, respectively.

The conjugate was used in the above-described homogeneous immunoassay for acetaminophen. Acceptable dose response curves were obtained for concentrations of acetaminophen ranging from 5–200 μg/ml. The reaction rate was approximately 0.30 Δ(absorbance units)/min. The "within run" variation of the assay was less than 5.5%.

A group of 52 samples, ranging from 0 μg/ml to nearly 200 μ/ml in acetaminophen were evaluated by the TDx system and the Synchron system (adapted to employ the conjugate of the present invention). Table 11 outlines the formulation of reagents used. Table 12 provides the Synchron assay parameters.

TABLE 11

| REAGENTS BUFFER SAMPLE | DILUTION/ CONCENTRATION | DILUENT COMPOSITION |
|---|---|---|
| Buffer | — | 80% APO Diluent 20% RHF Diluent |
| Latex-Avidin-Bidentate Conjugate | Latex = 1.5–2 mg/ml | 0.02 M Tris 0.2% Tween-20 0.2% BSA (pH 9) |
| Antibody | 1/150 | ARRAY Antibody Diluent (PBS, 0.2% BSA, pH 7) |
| Sample | Neat | — |

TABLE 12

| ASSAY PARAMETER | SETTING/VALUE/ASSIGNMENT |
|---|---|
| Buffer | 220 µl (Reagent Cartridge A) |
| Latex-Avidin-Bidentate Conjugate | 32 µl (Reagent Cartridge C) |
| Antibody | 40 µl (Reagent Cartridge B) |
| Sample | 3 µl (Sample cup) |
| Sample Add Time | 320 sec |
| Bidentate Trigger Add Time | 336 sec |
| Reaction Read Window | 344–348 sec |
| Blank Read Window | 250–280 sec |
| Detection Wavelength | 340 nm |
| Flash Correction Wavelength | 650 nm |
| Relative Extinction Coefficient 340 nm:650 nm | 1:0.1936 |
| Math Model | 8 |
| Reaction Type, Direction | Rate 1, Positive |

A linear regression of the data gave the equation:

Synchron=0.9855TDx+2.63 r=0.9952

Synchron mean=26.49 µg/ml

TDx mean=24.41 µg/ml

The results thus indicated that the 2-reagent system latex particle-enhanced assay of the present invention was capable of accurately measuring acetaminophen concentration.

EXAMPLE 7

LATEX PARTICLE-ENHANCED HOMOGENEOUS IMMUNOASSAY FOR ACETAMINOPHEN

The above-described acetaminophen-biotin bidentate was used in a 3-reagent latex particle-enhanced homogeneous immunoassay. As indicated above, this immunoassay differs from the 2-reagent system in several respects, but most notably in that the bidentate reagent is not "precomplexed" to the latex-avidin particle. Thus, the assay is conducted by adding biotinylated bidentate reagent, anti-acetaminophen antibody, and latex-avidin to a sample suspected of containing an unknown amount of acetaminophen. The presence of acetaminophen in the sample inhibits the agglutinization of the latex-avidin particles and the biotinylated bidentate.

As in the case of the 2-reagent system, acceptable dose response curves were obtained for concentrations of acetaminophen ranging from 5–200 µg/ml. The reaction rate was approximately 0.22 Δ(absorbance units)/min. The "within run" variation of the assay was less than 5.4%.

A group of 57 samples, ranging from 0 µg/ml to nearly 200 µg/ml in acetaminophen were evaluated by the TDx system and the Synchron system (adapted to employ the conjugate of the present invention). Table 13 outlines the formulation of reagents used. Table 14 provides the Synchron assay parameters.

TABLE 13

| Reagents/Buffer/ Sample | Dilution/Concentration | Diluent Composition |
|---|---|---|
| Buffer | | 80% APO Diluent 20% RHF Diluent |
| Latex-Avidin/Ab Mixture | Latex-Avidin/Ab = 1:1 (by vol.) | |
| Latex-Avidin | Latex = 1.5–2 mg/ml | 0.02 M Tris (pH 9) 0.2% Tween-20 0.2% BSA |
| Antibody | 1/150 | ARRAY Antibody Diluent (PBS, 0.2% BSA, pH 7) |
| Acetaminophen-Biotin Bidentant | 1.5 µg/ml | 0.02 M Tris (pH 9) 0.2% Tween-20 0.2% BSA |
| Sample | Neat | — |

TABLE 14

| ASSAY PARAMETER | SETTING/VALUE/ASSIGNMENT |
|---|---|
| Buffer | 220 µl (Reagent Cartridge A) |
| Latex-Avidin/Antibody Mixture | 62 µl (Reagent Cartridge B) |
| Acetaminophen-Biotin Bidentate | 20 µl (Reagent Cartridge B) |
| Sample | 3 µl |
| Sample Add Time | 320 sec |
| Bidentate Trigger Add Time | 336 sec |
| Reaction Read Window | 344–348 sec |
| Blank Read Window | 250–280 sec |
| Detection Wavelength | 340 nm |
| Flash Correction Wavelength | 650 nm |
| Relative Extinction Coefficient 340 nm:650 nm | 1:0.1936 |
| Math Model | 8 |
| Reaction Type, Direction | Rate 1, Positive |

A linear regression of the data gave the equation:

Synchron=0.9719TDx+3.86 r=0.9927

Synchron mean=28.58 µg/ml

TDx mean=25.44 µg/ml

The results thus indicated that the 3-reagent system latex particle-enhanced assay of the present invention was also capable of accurately measuring acetaminophen concentration.

As indicated, both the 2-reagent and the 3-reagent latex-based bidentate assay used substantially less reagents and sample than those employed in the corresponding liquid formulated method. Without the incorporation of latex reagent, the acetaminophen assay developed on the ARRAY[10] required, for acceptable dose response, 2.18 µl of neat antiserum (43.5 µl at 1/20 dilution) and 1.75 µl of neat sample. Since the reagent and sample usage on the ARRAY are at least 2.5 times less than those for the Synchron, as much as 5.45 µl of neat antiserum and 4.38 µl of neat sample would have to be used for the assay on the Synchron. With the latex reagents, 3 µl of neat sample and 0.21 µl of neat antiserum (31 µl at 1/150 dilution) were found to be sufficient to give dose response steeper than the liquid formatted counterpart. Thus, the latex method used 27 times less antibody and 1.46 times less sample.

EXAMPLE 8

LATEX PARTICLE-ENHANCED HOMOGENEOUS IMMUNOASSAY FOR PROCAINAMIDE

The methods and reagents described above can be modified to produce a highly sensitive latex particle-enhanced homogeneous assay for procainamide or N-acetyl procainamide.

An initial step in such an assay is the formation of the latex-avidin particle. Suitable particles were obtained using the method of Example 2.

Solutions containing either the N-acetyl procainamide-biotin or procainamide-biotin reagents were prepared for use in the assay. The solution of N-acetyl procainamide-biotin reagent was prepared by weighing out 3 mg of N-acetyl procainamide-biotin reagent, and dissolving the material in 5 ml of a 40:60 mixture of dimethyl formamide:20 mM TRIS, pH 7.0. The final solution had a N-acetyl procainamide-biotin concentration of 600 µg/ml. The solution of procainamide-biotin reagent was prepared by weighing out 10 mg of procainamide-biotin reagent, and dissolving the material in 2 ml of methanol. The final solution had a procainamide-biotin concentration of 5 mg /ml.

The HABA bound to the latex-avidin was titrated by adding 50 µl aliquots of the biotin-bidentate reagent solution to the orange-yellow HABA-latex-avidin solution until the solution turned light yellow, then 10% excess was added, totalling approximately 500 µl. The reactants were allowed to stir for approximately 30 minutes at room temperature.

Unbound reactants were removed by dialysis using 25 mm dialysis tubing having a molecular weight cut off of 12–14 kd (Baxter). Dialysis was against 20 mM Tris, pH 9.0, 0.2% Tween-20, and 0.9% sodium azide. Dialysis was conducted at 4° C. and used 4 changes of buffer (approximately 10 liters each).

The recovered latex-avidin-biotinylated bidentate reagent conjugates were used in homogeneous immunoassays. For, procainamide, a linear regression of the data based on the analysis of 21 samples gave the equation:

Array=1.04TDx+0.24 r=0.9954

For, N-acetyl procainamide, a linear regression of the data based on the analysis of 20 samples gave the equation:

Array=0.996TDx−0.183 r=0.9946

The results thus indicated that the latex particle-enhanced assays of the present invention were capable of accurately measuring procainamide or N-acetyl procainamide concentration. The latex particle-enhanced homogeneous N-acetyl procainamide and procainamide assays both exhibited high sensitivity and throughput, while reducing the amount of antiserum required. The method also eliminated or reduced matrix problems and was particularly amenable to automated processing.

EXAMPLE 9

LATEX PARTICLE-ENHANCED HOMOGENEOUS IMMUNOASSAY FOR AMINOGLYCOSIDE ANTIBIOTICS

Aminoglycoside antibiotics, such as kanamycin, tobramycin, amikacin and gentamycin, are powerful broad spectrum antibiotics that are widely used in the treatment and management of gram negative bacterial infections, especially Pseudomonas (Pancoast, S. J., *Med. Clin. Nor. Amer.* 72:581–612 (1988)). The antibiotics are also active against certain stains of Staphylococcus (Truchet, A. et al., *Ann. Biol. Clin.* 48:541–546 (1990)) and certain species of gram positive bacteria, such as Corynebacteria and Neisseria. The respective spectra of activities, and clinical uses of these antibiotics are quite similar (Pancoast, S. J., *Med. Clin. Nor. Amer.* 72:581–612 (1988)).

Amikacin has the broadest spectrum of available aminoglycoside antibiotics. It is therefore used to manage post-surgical infection, and, in combination with other antibiotics, to manage secondary bacterial infections in AIDS patients (Pancoast, S. J., *Med. Clin. Nor. Amer.* 72:581–612 (1988)).

The usage of aminoglycoside antibiotics has been limited by side-effects (such as nephrotoxicity and ototoxicity) (Costa Silva, V. L. et al., *Renal Physiol.* 10:327–337 (1987); Fee, W. E. et al., *Rev. Infect. Dis.* 5 (*Suppl.* 2):S304 (1983); Lane, A. Z. et al., *Amer. J. Med.* 62:911 (1977)). A narrow margin, however, exists between the therapeutic dosage and toxicity-inducing overdosages (Witchitz, J. L. et al., *Nouv. Presse Méd.* 11:489–491 (1982); Damien, J. M. et al., *Ann. Biol. Clin.* 48:217–220 (1984)). Thus, accurate monitoring of the serum concentration of the drug can decrease the incidence of adverse side effects (Damien, J. M. et al., *Ann. Biol. Clin.* 48:217–220 (1984)). Aminoglycoside levels are monitored by rapid bioassay, enzyme-linked immunoassays (such as EMIT®, Syva) and fluoro-immunoassays (Ames TDA) (Damien, J. M. et al., *Ann. Biol. Clin.* 48:217–220 (1984); White, L. O. et al. *Antimicrob. Agents Chemother.* 19:1064–1066 (1981)).

The methods and reagents described above can be modified to produce highly sensitive latex particle-enhanced homogeneous assays for aminoglycoside antibiotics, such as tobramycin, amikacin, or gentamycin.

An initial step in such an assay is the formation of the latex-avidin particle. Suitable particles were obtained using the method of Example 2.

A solution containing the aminoglycoside antibiotic-biotin bidentate of the aminoglycoside to be assayed was prepared for use in the assay. For example, to assay tobramycin, gentamycin or amikacin, a solution of the aminoglycoside-biotin reagent (i.e., tobramycin-biotin reagent, gentamycin-biotin reagent or amikacin-biotin reagent) was prepared. To produce the reagent solution 15 mg of the aminoglycoside-biotin reagent was dissolved in 2 ml of a freshly prepared the 1:1 methanol:water mixture. The final solution had an aminoglycoside-biotin concentration of 7.5 mg /ml.

The HABA bound to the latex-avidin was titrated by adding 50 µl aliquots of the biotin bidentate reagent solution to the orange-yellow HABA-latex-avidin solution until the solution turned light yellow, then 10% excess was added, totalling approximately 500 µl. The reactants were allowed to stir for approximately 30 minutes at room temperature.

Unbound reactants were removed by dialysis using 25 mm dialysis tubing having a molecular weight cut off of 12–14 kd (Baxter). Dialysis was against 20 mM Tris, pH 9.0, 0.2% Tween-20, and 0.9% sodium azide. Dialysis was conducted at 4° C. and used 4 changes of buffer (approximately 10 liters each).

The above-described reagents thus permitted latex particle-enhanced homogeneous assays of aminoglycoside antibiotics. The assays were each found to exhibit high sensitivity and throughput, while reducing the amount of antiserum required. The method also eliminated or reduced matrix problems and was particularly amenable to automated processing.

The above-described assays were compared against the TDx assay. For the immunoassay for tobramycin, a linear regression of the data based on the analysis of 45 samples gave the equation:

Synchron=1.04TDx+0.16 r=0.9847

For the immunoassay for gentamicin, a linear regression of the data based on the analysis of 33 samples gave the equation:

Synchron=1.1TDx−0.34 r=0.9516

For the immunoassay for amikacin, a linear regression of the data based on the analysis of 15 samples gave the equation:

Array=0.991TDx+0.36 r=0.9618

The results thus indicated that the latex particle-enhanced assays of the present invention were capable of accurately measuring the concentrations of aminoglycoside antibiotics.

EXAMPLE 10

LATEX PARTICLE-ENHANCED HOMOGENEOUS IMMUNOASSAY FOR VANCOMYCIN

Vancomycin is an amphoteric glycopeptide antibiotic (Anon., *J. Antimicrob. Chemother.* 14 (Suppl. D):1–109 (1984); Jordan et al., In: *Antibiotics*, Vol. 3, Corcoran, J. W. et al., Eds., Springer-Verlag, NY, pp 704–718 (1975)). Since use of the drug has been associated with adverse side-effects, a capacity to accurately determine vancomycin serum concentrations is extremely important.

The above described methods for producing vancomycin-biotin bidentate reagents were therefore exploited in order to define an accurate immunoassay for vancomycin. Despite the structural complexity of vancomycin, it has only three non-hydroxyl functional groups that are amenable to coupling with biotin or other agents using mild conditions. These groups include one primary amino group, one secondary amino group, and a carboxyl group. Of these groups, the carboxyl group is quite sterically hindered, and the amino groups either failed to react, or formed products having insufficient vancomycin immunogenicity.

The following method was, however, in producing a suitable vancomycin bidentate. The method can be used to conjugate any a variety of ligands to vancomycin's non-functional carboxyl group. In particular, bidentates of BSA and of biotin were prepared.

The bidentates were prepared by adding:

100 mg (0.24 mmoles) of a biotinylated amine, 28 mg (0.24 mmoles) of N-hydroxysuccinimide, 50 mg (0.24 mmoles) of dicyclohexylcarbodiimide, and a trace (70 µl) of triethylamine to a solution of 300 mg (0.2 mmoles) of vancomycin hydrochloride (in 20 ml of DIMF). After 6 hours of stirring at 50° C., the reaction was completed as indicated by the appearance of a new spot in a thin layer chromatograph. The new spot exhibited UV absorption and was positive to cinnamaldehyde spray (showing the presence of biotin).

Figure 5:
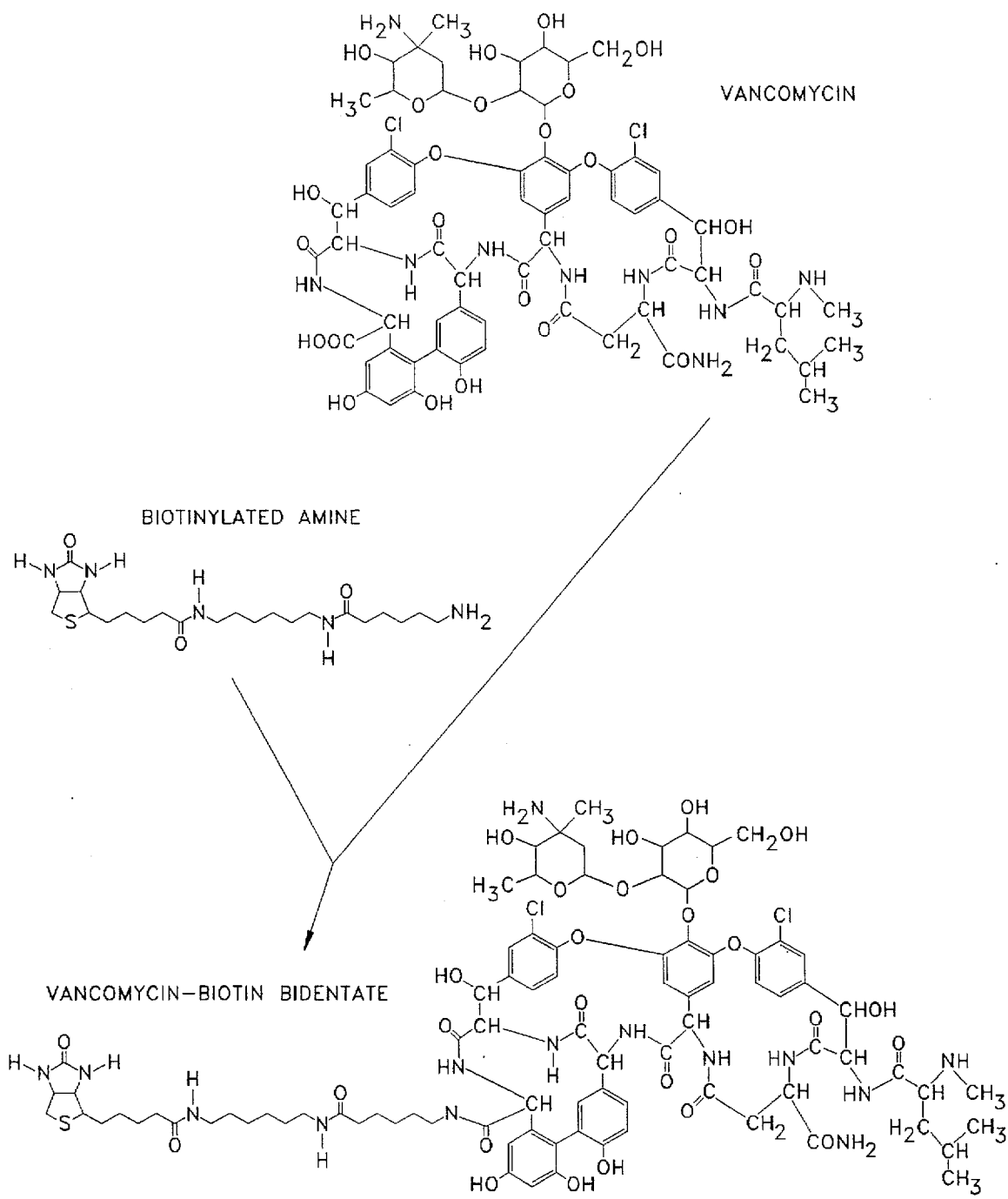
FIG. 5 shows a synthetic scheme for producing a vancomycin-biotin bidentate.

After the solvent was removed under reduced pressure, the reaction mixture was chromatographed on a silica gel column using methanol/15% ammonium hydroxide (9:1) to give the desired final product. Recrystallization from methanol yielded the pure vancomycin-biotin bidentate (180 mg ). The structures of the reactants and the synthetic scheme of the reaction are shown in FIG. 5.

The immunogenicity of the vancomycin-biotin bidentate was assessed with both the Syva EMIT® and the Abbott TDx kits. The values used to form the Syva EMIT® standard curve are shown in Table 15.

TABLE 15

| EMIT ® Standard Curve for Vancomycin | |
|---|---|
| Concentration (µg/ml) | Rate |
| 0 | 562 |
| 5 | 578 |
| 10 | 590 |
| 20 | 616 |
| 30 | 651 |
| 50 | 691 |

The values obtained for the vancomycin bidentate run as unknown with the MIT reagent are shown in Table 16.

TABLE 16

| Vancomycin Bidentate | | |
|---|---|---|
| Concentration (µg/ml) | Rate | Recovery (µg/ml) |
| 50 | 741 | >50 |
| 100 | 802 | >50 |

The values obtained for the vancomycin bidentate run as unkown with the Abbott TDx kits are shown in Table 17.

TABLE 17

| Concentration | Recovery (µg/ml) by TDx | | |
|---|---|---|---|
| (µg/ml) | Rep. 1 | Rep. 2 | Avg. |
| 50 | 77.9 | 65.8 | 71.9 |
| 100 | >50 | >50 | >50 |

The available anti-vancomycin antibodies exhibit low avidity to vancomycin, and hence the sensitivity of vancomycin immunoassays may be improved through the development of more avid antibodies. Such antibodies may be obtained by conjugating an immunogenic molecule to vancomycin, and then injecting the conjugate into animals, or incubating the conjugate in the presence of antibody producing cells. Vancomycin conjugated to BSA is particularly suitable for eliciting the production of such anti-vancomycin antibodies.

Figure 6:
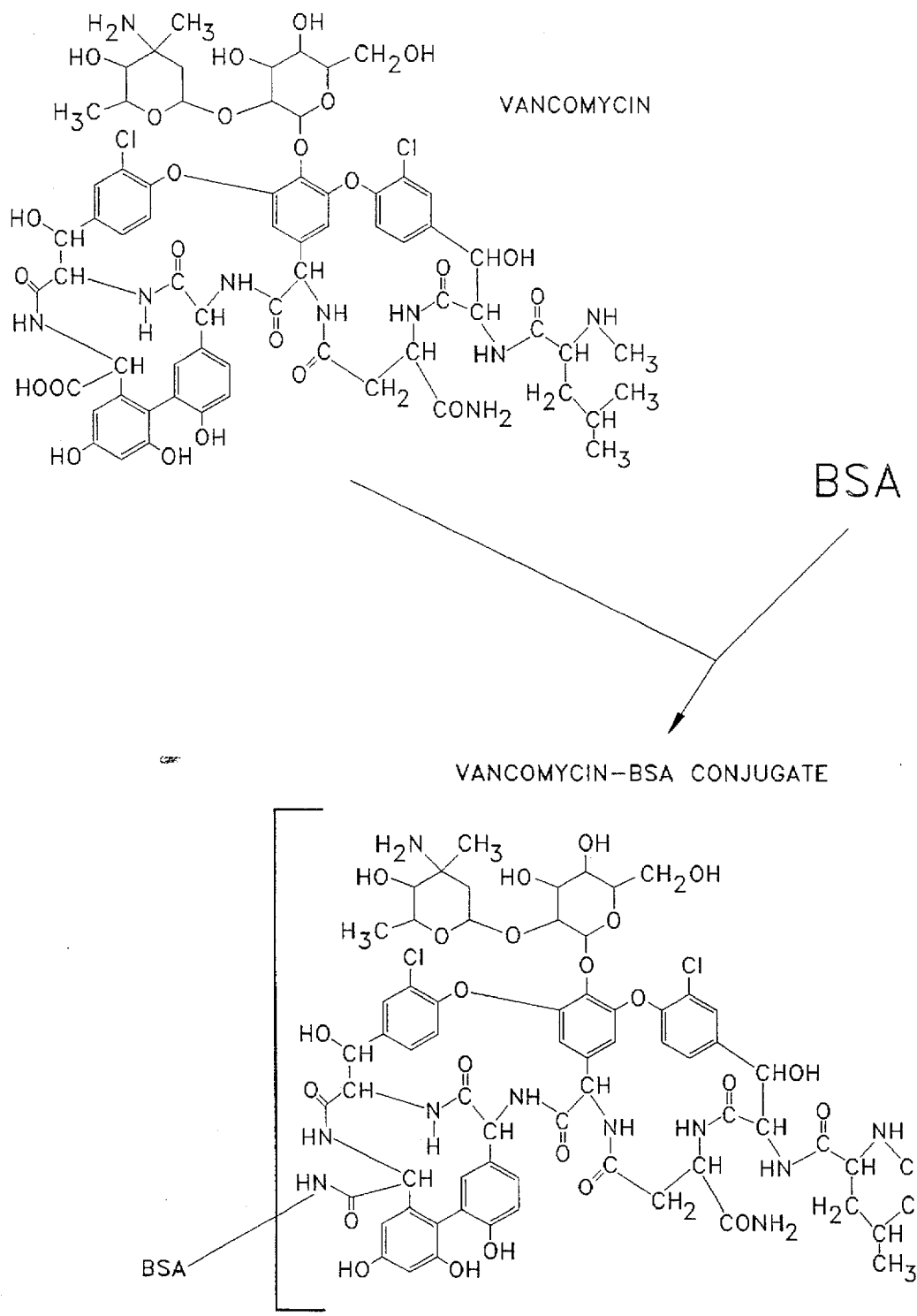
FIG. 6 shows the structure of a vancomycin-BSA conjugate.

Such vancomycin-BSA conjugates were produced in the following manner. Triethylene (1 ml), N-hydroxysuccinimide (140 mg, 1.2 mmoles) and dicyclohexylcarbodiimide (250 mg, 1.2 mmoles) were introduced into a suspension of 1485 mg (1 mmole) of vancomycin hydrochloride in 20 ml of DMF. After stirring for 1 hour at room temperature, the reaction mixture was concentrated under vacuum at below 35° C. to approximately 5 ml. 140 mg of BSA (dissolved in 25 ml of water was then added). The reactants were stirred at room temperature for 3 hours after which the reaction mixture was filtered and the filtrate was dialyzed in saline at 4° C. to give the vancomycin-BSA conjugate (40 ml ). The structure of the conjugate is shown in FIG. 6. The conjugate was found to have a BSA concentration of 3.5 mg /ml and a vancomycin concentration of 34.1 µg/ml, based on results obtained using the TDx assay. These values indicate that the conjugate had a vancomycin-:BSA molar ratio of 5:1.

The vancomycin-BSA conjugate was found to exhibit good immunoreactivity, as shown by TDx assay results (Table 18).

TABLE 18

Vancomycin-BSA Conjugate

| Dilution Factor | BSA conc. (µg/ml) | Recovery (µg/ml) by TDx | | |
|---|---|---|---|---|
| | | Rep.1 | Rep.2 | Avg |
| 1:10 | 0.35 | 34.4 | 33.8 | 34.1 |
| 1:4 | 0.875 | >50 | >50 | >50 |

The results thus demonstrated the capacity of the methods of the present invention to produce vancomycin-biotin bidentates that can be used in immunoassays of vancomycin. In particular, such bidentates can be used in the latex particle-enhanced homogeneous immunoassays described herein by permitting the biotinylated vancomycin bidentate to conjugate with avidin-latex particles, as described herein. The results further indicated that the methods of the invention could be used to produce highly immunogenic vancomycin-protein conjugates. The results obtained using a latex-avidin bidentate assay for vancomycin are shown in Table 19. The assay was conducted on an ARRAY 360 at a sample dilution of 1/54.

TABLE 19

| µg/ml | Rate Unit | Rate Unit | Mean | B/B₀ |
|---|---|---|---|---|
| 0 | 1330 | 1340 | 1335 | 100.00 |
| 5 | 1190 | 1190 | 1190 | 89.14 |
| 10 | 1040 | 1040 | 1040 | 77.90 |
| 25 | 648 | 667 | 658 | 49.25 |
| 50 | 267 | 267 | 267 | 20.00 |
| 100 | 125 | 138 | 132 | 9.85 |

EXAMPLE 11

LATEX PARTICLE-ENHANCED HOMOGENEOUS IMMUNOASSAY FOR THEOPHYLLINE

Theophylline (1,3 dimethylxanthine) is used to prevent or alleviate asthma and acute exacerbation of obstructive airways disease. In adults, theophylline has been used to treat acute pulmonary edema, and congestive cardiac failure (Dal Negro, R. et al., *J. Int. Med. Res.* 15:391–396 (1987)). The drug is also used to treat recurrent neonatal apnoea (Frowe, D. J. et al., *Ann. Clin. Biochem.* 25:4–26 (1988)). The ability to accurately measure theophylline serum or plasma levels is extremely important, since theophylline overdose may have life-threatening side effects (Frowe, D. J. et al., *Ann. Clin. Biochem.* 25:4–26 (1988)). The structural similarity between theophylline and caffeine significantly complicates efforts to accurately determine the serum theophylline level (Frowe, D. J. et al., *Ann. Clin. Biochem. 25:4–26* (1988)). Theophyl-line concentration is generally determined by immunoassay, such as the Beckman ICS system, the Abbott fluorescent polarized immunoassay TDx system (Klotz, U., *Ther. Drug. Monitor.* 15:462–464 (1993)), or the EMIT® system (Hill, M., *J. Allergy Clin. Immunol.* 82:30–34 (1988)).

The methods and reagents described above were used to produce a highly sensitive latex particle-enhanced homogeneous assay for theophylline.

An initial step in such an assay is the formation of the latex-avidin particle. Suitable particles were obtained using the method of Example 2.

A reagent solution of theophylline-biotin bidentate was prepared for use in the assay. Theophylline-biotin bidentate was prepared as described by Harris. P.C. et al. (U.S. Pat. No. 5,196,351). To produce the reagent solution, 10 mg of the theophylline-biotin bidentate reagent was dissolved in 2 ml of methanol. The final solution had a theophylline-biotin concentration of 5.0 mg/ml.

The HABA bound to the latex-avidin was titrated by adding 50 µl aliquots of the biotin bidentate reagent solution to the orange-yellow HABA-latex-avidin solution until the solution turned light yellow, then 10% excess was added, totalling approximately 500 µl. The reactants were allowed to stir for approximately 30 minutes at room temperature.

Unbound reactants were removed by dialysis using 25 mm dialysis tubing having a molecular weight cut off of 12–14 kd (Baxter). Dialysis was against 20 mM Tris, pH 9.0, 0.2% Tween-20, and 0.9% sodium azide. Dialysis was conducted at 4° C. and used 4 changes of buffer (approximately 10 liters each).

The above-described reagent was used in a latex particle-enhanced homogeneous assays of theophylline. A linear regression of the data based on the analysis of 51 samples gave the equation:

$$Synchron = 1.06 TDx - 0.14$$

$$r = 0.9836$$

The assay was found to exhibit high sensitivity and throughput, while reducing the amount of antiserum required. The method also eliminated or reduced matrix problems and was particularly amenable to automated processing.

EXAMPLE 12

LATEX PARTICLE-ENHANCED HOMOGENEOUS IMMUNOASSAY FOR CARBAMAZEPINE

Carbamazepine is widely used in the treatment and management of affective diseases, such as epilepsy, acute mania and depression (Ballenger, J. C., *J. Clin. Psychiatry* 49 (*Suppl.*):13–19 (1988); Loiseau, P. et al., In: *Antiepilectic Drugs*, 3rd. Ed. (Levy, R. et al., Eds.), Raven Press, NY, pp. 533–554 (1989). Despite its therapeutic value, use of carbamazepine is associated with skin rashes, adverse behavioral effects, and, in rare instances aplastic anemias (Loiseau, P. et al., In: *Antiepilectic Drugs*, 3rd. Ed. (Levy, R. et al., Eds.), Raven Press, NY, pp. 533–554 (1989)). Thus an ability to accurately determine serum carbamazepine levels is central to the therapeutic use of the drug.

The methods and reagents described above were used to produce a highly sensitive latex particle-enhanced homogeneous assay for carbamazepine.

An initial step in such an assay is the formation of the latex-avidin particle. Suitable particles were obtained using the method of Example 2.

A solution containing the carbamazepine-biotin bidentate was prepared for use in the assay. To produce the reagent solution, 10 mg of the carbamazepine-biotin bidentate reagent was dissolved in 2 ml of methanol. The final solution had a carbamazepine-biotin concentration of 5.0 mg /ml.

The HABA bound to the latex-avidin was titrated by adding 50 µl aliquots of the biotin bidentate reagent solution to the orange-yellow HABA-latex-avidin solution until the solution turned light yellow, then 10% excess was added, totalling approximately 500 µl. The reactants were allowed to stir for approximately 30 minutes at room temperature.

Unbound reactants were removed by dialysis using 25 mm dialysis tubing having a molecular weight cut off of 12-14 kd (Baxter). Dialysis was against 20 mM Tris, pH 9.0, 0.2% Tween-20, and 0.9% sodium azide. Dialysis was conducted at 4° C. and used 4 changes of buffer (approximately 10 liters each).

The above-described reagent was used in a latex particle-enhanced homogeneous assays of carbamazepine. A linear regression of the data based on the analysis of 50 samples gave the equation:

$$\text{Synchron} = 1.09 \text{TDx} - 0.2$$

$$r = 0.9886$$

The assay was found to exhibit high sensitivity and throughput, while reducing the amount of antiserum required. The method also eliminated or reduced matrix problems and was particularly amenable to automated processing.

EXAMPLE 13

LATEX PARTICLE-ENHANCED HOMOGENEOUS IMMUNOASSAY FOR PRIMIDONE

Primidone (5-ethyldihydro-5-phenol-4,6 (1H,5H) pyrimidinedione) is an anticonvulsant drug of the barbiturate analog. It is used in the treatment and management of grand mal, pyschomotor and focal epileptic seizures and other convulsive disorders (Smith, D. B., In: *Antiepilectic Drugs*, 3rd. Ed. (Levy, R. et al., Eds.), Raven Press, NY, pp. 533–554 (1989)). There is wide variation between the administered dosage and the resultant plasma levels in different individuals; however, plasma levels do correlate well with the brain concentrations of primidone (Smith, D. B., In: *Antiepilectic Drugs*, 3rd. Ed. (Levy, R. et al., Eds.), Raven Press, NY, pp. 533–554 (1989)). Thus, the effective use of the drug requires accurate determinations of the drug's serum concentration.

The methods and reagents described above were used to produce a highly sensitive latex particle-enhanced homogeneous assay for primidone.

An initial step in such an assay is the formation of the latex-avidin particle. Suitable particles were obtained using the method of Example 2.

Figure 7:
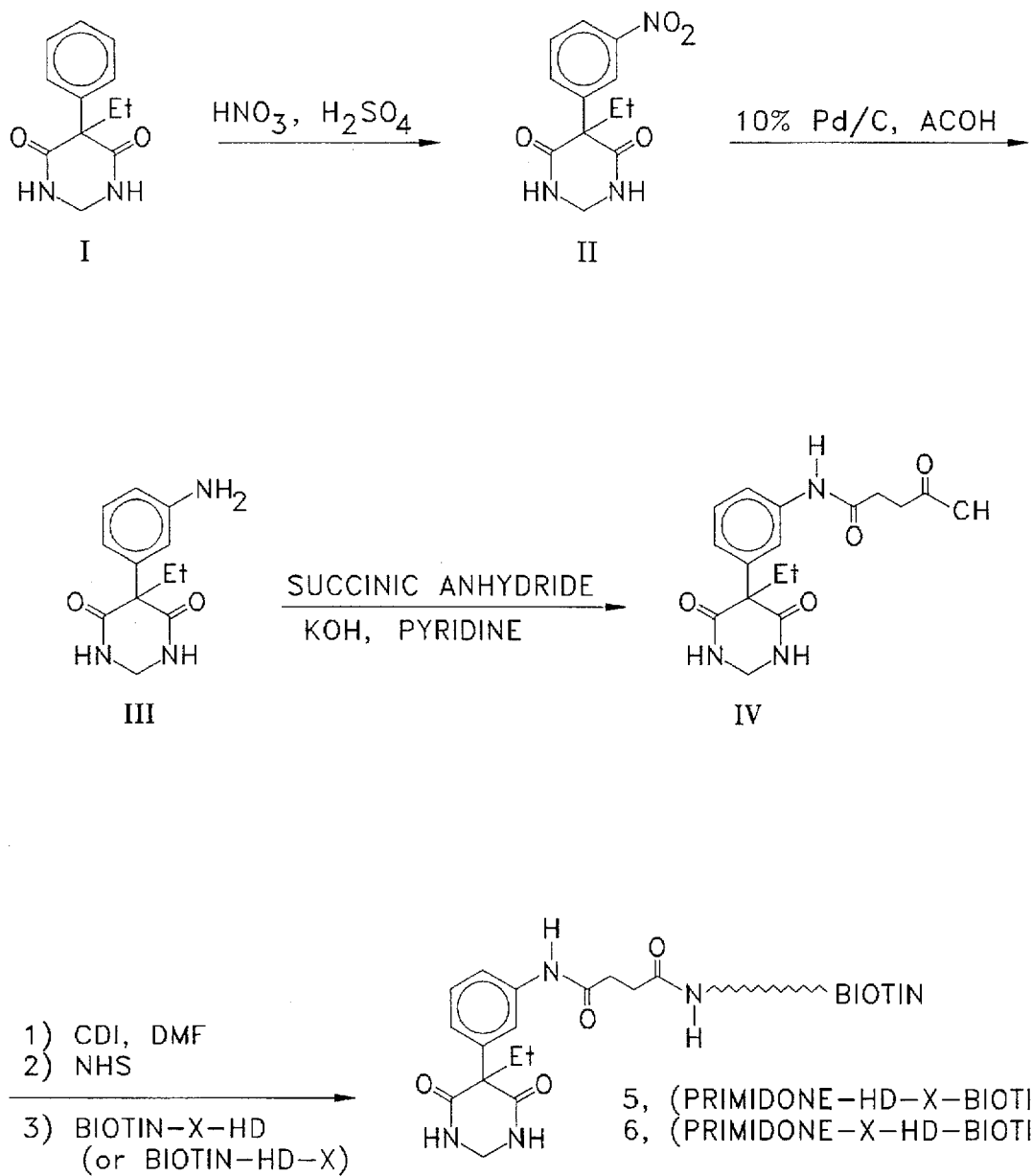
FIG. 7 shows a synthetic scheme for producing a primidone-biotin bidentate.

A primidone-biotin bidentate was prepared by first forming a carboxyl primidone derivative, and then condensing this derivative with an alkyloamidobiotin. A preferred method for synthesizing the carboxyl primidone derivative is described in FIG. 7. In the initial step of the synthesis, primidone (1) is nitrated, using nitric acid and sulfuric acid, to give the corresponding nitro derivative (2). The nitro derivative is subjected to catalytic hydrogenation (10% Pd/C; Acetyl alcohol) to reduce the nitro group to an amine group (3). The amiminated derivative (3) is then alkylated via a nucleophilic substitution of the amino group with succinic anhydride (KOH, pyridine) to yield carboxyl primidone (4). The carboxyl primidone (4) is coupled to an amidobiotin (such as HD-biotin) via reaction with N-hydroxysuccinimide and carbonyidiimidazole (CDI) in dimethyl formamide as described above.

A solution containing the primidone-biotin bidentate was prepared for use in the assay. To produce the reagent solution, 10 mg of the primidone-biotin bidentate reagent was dissolved in 2 ml of methanol. The final solution had a primidone-biotin concentration of 5.0 mg/ml.

The HABA bound to the latex-avidin was titrated by adding 50 µl aliquots of the biotin bidentate reagent solution to the orange-yellow HABA-latex-avidin solution until the solution turned light yellow, then 10% excess was added, totalling approximately 500 µl. The reactants were allowed to stir for approximately 30 minutes at room temperature.

Unbound reactants were removed by dialysis using 25 mm dialysis tubing having a molecular weight cut off of 12-14 kd (Baxter). Dialysis was against 20 mM Tris, pH 9.0, 0.2% Tween-20, 0.9% and sodium azide. Dialysis was conducted at 4° C. and used 4 changes of buffer (approximately 10 liters each).

The above-described primidone-biotin avidin conjugates were evaluated as a rate nephelometric TDM reagent using the Beckman ICS Analyzer II using the following conditions: reagents were used: primidone-HD-biotin avidin conjugate (0.3 mg/ml in CBS buffer); goat anti-primidone antibody (1/15 dilution); primidone standards in 8% BSA. The results of the shown in Table 20.

TABLE 20

| Evaluation of Primidone Conjugate with Anti-Primidone Antibody | | |
|---|---|---|
| Concentration (µg/ml) | Rate Unit | % |
| 0 | 1715 | 100 |
| 1 | 1480 | 86.3 |
| 2 | 1330 | 77.7 |
| 4 | 1130 | 65.9 |
| 8 | 764 | 44.6 |
| 12.5 | 558 | 32.5 |
| 25 | 338 | 19.7 |
| 50 | 280 | 16.3 |

The assay was thus found to exhibit high sensitivity and throughput while reducing the amount of antiserum required. The method also eliminated or reduced matrix problems and was particularly amenable to automated processing. The above-described reagent can alternatively be used in a latex particle-enhanced homogeneous assay of primidone.

EXAMPLE 14

LATEX PARTICLE-ENHANCED HOMOGENEOUS IMMUNOASSAY FOR QUINIDINE quinidine (6-methoxy-a-(5-vinyl-2-quinuclidinyl)-4-quinolinemethanol or 6' methoxycinchonine-9-ol) is a Cinchona alkaloid that is used in the treatment and management of cardiac arrythmia (Ariado, M. et al., *J. Clin. Pharmacol.* 15:477 (1975)). Quinidine's therapeutic utility requires a careful monitoring of the serum levels of the drug in recipient patients (Dietmann, K. et al., *Arzneimittel-Forsch.* 27:589 (1977)).

The methods of the present invention were employed to produce a quinidine-biotin bidentate that could then be used with the above-described latex-avidin particles to provide a homogeneous immunoassay for quinidine.

Figure 8:
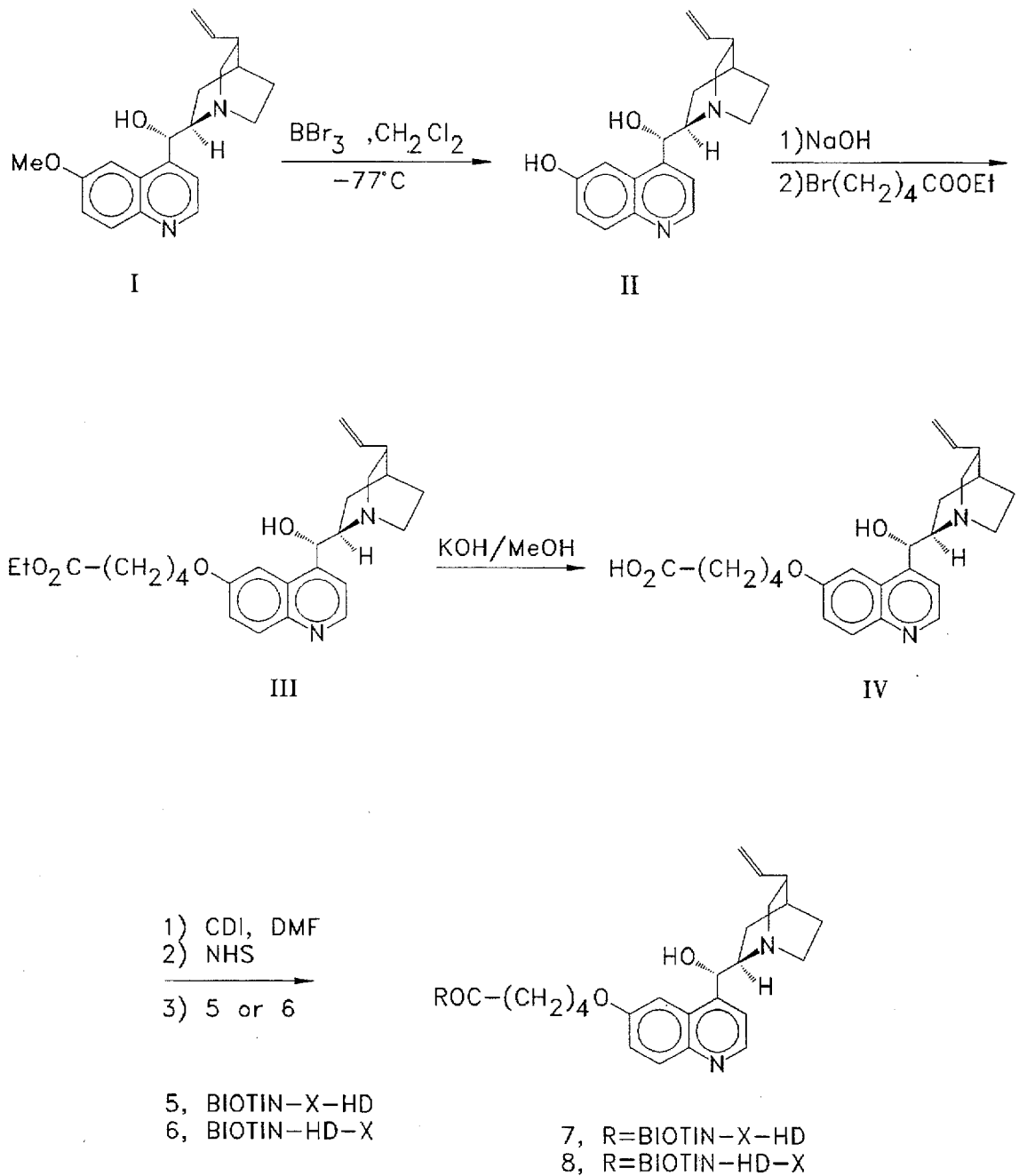
FIG. 8 shows a synthetic scheme for producing a quinidine-biotin bidentate.

The synthetic scheme used to prepare the quinidine-biotin bidentate is shown in FIG. 8. As shown in FIG. 8, quinidine (1) was first demethylated in a reaction using boron tribromide in methylene chloride at low temperature (−78° C.) to yield the corresponding phenol (2). This reaction did not cause any rearrangements to the remainder of the molecule. The phenol (2) was then alkylated using ethyl 5-bromovalerate to five the ethyl ester (3). Hydrolysis of the ethyl ester (3) using potassium hydroxide in methanol yielded the acid (4). The acid (4) was then coupled to an amidobiotin (5 or 6) using the N-hydroxysuccinimide/carbonyldiimidazole methods described above to give the desired biotinylated quinidine (8).

The biotinylated quinidine (8) was coupled to avidin-coated latex particles and subjected to dialysis, as described above, in order to obtain a bidentate reagent that could be used in a homogeneous immunoassay for quinidine. The assay was optimized using a Synchron CX5 Analyzer (Beckman Instruments). Antibody was goat anti-quinidine; DADE TDM controls were run to confirm that the assay was detecting the proper amount of quinidine in the sample. The assay was found to be both sensitive reliable. The results are summarized in Tables 21 and 22.

TABLE 21

Quinidine Assay Synchon CX5

| Standards (μg/ml) | Rate | B/B$_0$ |
|---|---|---|
| 0 | 0.13453 | 1.000 |
| 1 | 0.09566 | 0.711 |
| 2 | 0.07438 | 0.553 |
| 4 | 0.03696 | 0.275 |
| 8 | 0.02033 | 0.151 |
| 12 | 0.0145 | 0.108 |

TABLE 22

| DADE TDM Control | Rate (mean of 2 replicates) | Range | Recovered |
|---|---|---|---|
| Level 1 | 0.09688 | 0.8–1.2 | 1 |
| Level 2 | 0.04451 | 2.8–3.6 | 3.5 |
| Level 3 | 0.02718 | 5.5–7 | 6.4 |

EXAMPLE 15

LATEX PARTICLE-ENHANCED HOMOGENEOUS IMMUNOASSAY FOR CANNABINOIDS

Figure 9:
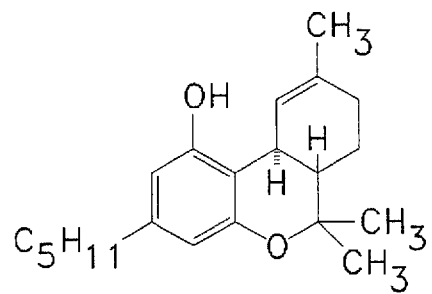
FIG. 9 shows the structures of tetrahydrocannabinol (1), and its metabolite, $\Delta^9$-THC-carboxylic acid (2).
Figure 9:
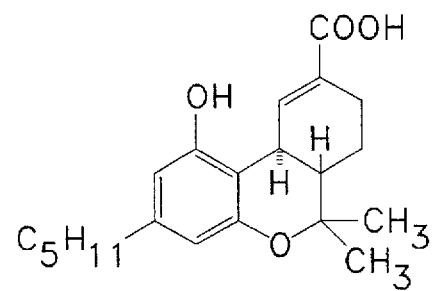

The methods of the present invention were employed to define a homogeneous immunoassay for cannabinoids, and in particular, for tetrahydrocannabinol ("THC," FIG. 9 (1)), and its metabolites, such as $\Delta^9$-THC-carboxylic acid (FIG. 9 (2)).

Figure 10:
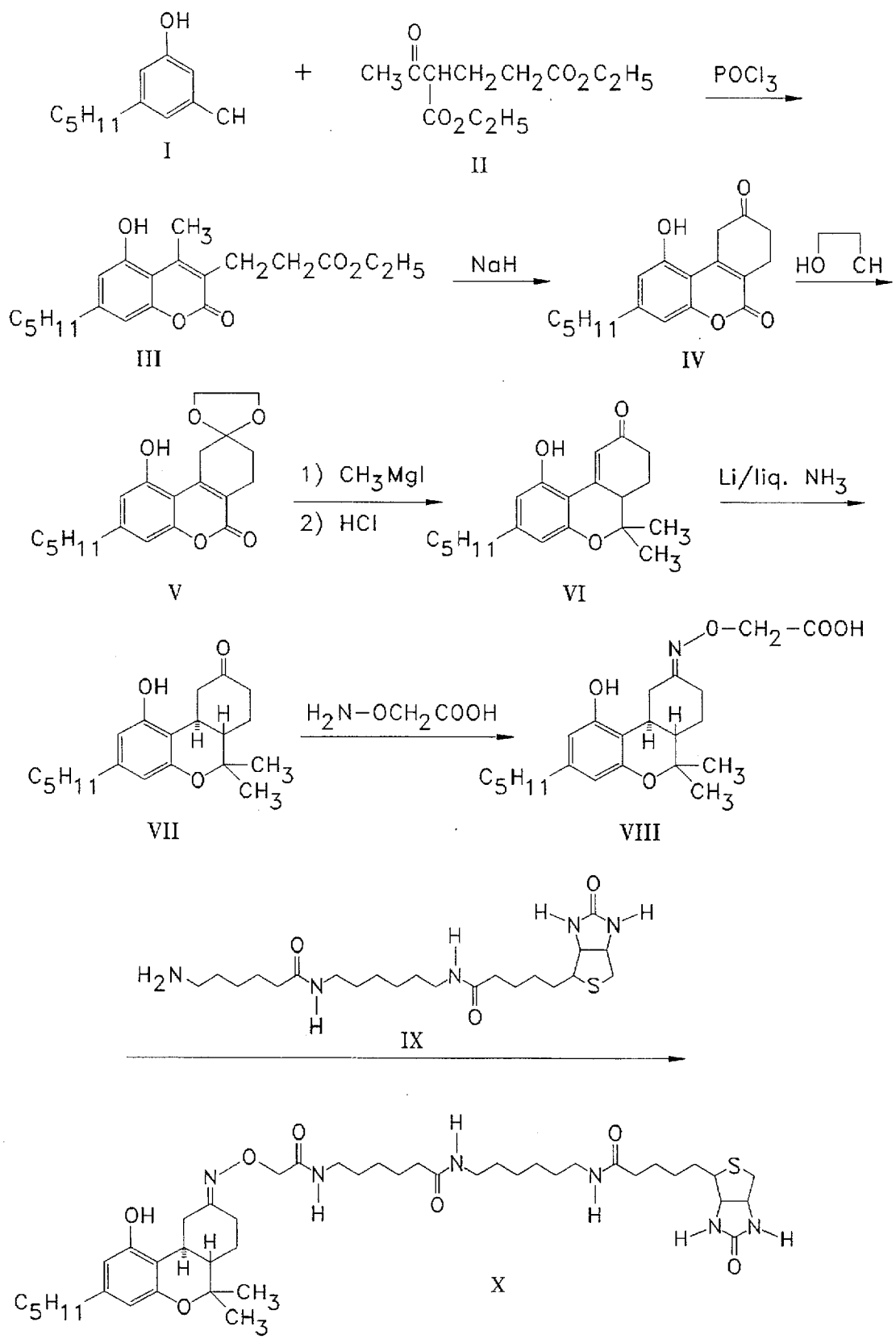
FIG. 10 shows the synthetic scheme used to synthesize a tetrahydrocannabinol-biotin bidentate.

The assay employed a tetrahydrocannabinol-biotin bidentate which was synthesized as shown in FIG. 10. The synthetic scheme started with olivetol (I) and a-acetoglutaric acid (II) in the presence of phosphorus oxychloride to give the coumarin derivative (III). Sodium hydride was used to cyclize the alkyl ester group to yield (IV). The keto group of IV was then protected with ethylene glycol to yield (V). Compound V was converted to VI using methyl magnesium iodide followed by removal of the ethylene glycol protecting group in acid (HCl) medium. Compound VI was reacted with lithium in liquid ammonium in order to reduce the double bond, thereby yielding (VII). The product (VII) was found to have a melting point of 162°–163° C., thus indicating its purity.

Compound VII was converted to the carboxyl THC derivative (VIII) by reaction with carboxylmethoxylamine. The purity of the product was determined by thin layer chromatography. The product exhibited an Rf of approximately 0.13 in 1:4 methanol:chloroform.

Compound VII was reacted with an alkyloamidobiotin (IX) to give the desired THC-biotin bidentate (X). The compound had a melting point of 80–82° C., and exhibited an Rf of 0.34 in thin layer chromatography in a 5:5:14:1 mixture of ethyl acetate:methanol:chloroform:ammonium.

The immunoreactivity of the THC-biotin bidentate was assessed using the Syva EMIT® THC kit reagents. Thus, solutions of the THC-biotin bidentate (X) were prepared at 8500, 850, and 100 ng/ml by dissolving X with the EMIT® negative calibrator. The samples were then assayed using the EMIT® reagents. The assay results are shown in Table 23.

TABLE 23

| Target Concentration of THC-Biotin (ng/ml) | Observed Concentration of THC-Biotin by EMIT® (ng/ml) | % Observed/Target |
|---|---|---|
| 8500 | >100 | — |
| 850 | >100 | — |
| 100 | 80 | 60 |

A latex-enhanced immunoassay format was designed. The latex-avidin conjugates used in the immunoassay were prepared as follows. To 9.3 ml of MOPS buffer (0.1M) containing 0.59% of Tween-20 were added: (1) a suspension of 1.25 ml of carboxylate modified 60 nm latex particles (Seradyn), (2) a solution of 82 mg of N-hydroxysuccinimide in 1.32 ml of cold MOPS buffer, and (3) a solution of 58 mg of a water soluble carbodiimide in 1.25 ml of cold MOPS buffer. After one hour of gentle stirring at pH 6 at 4° C., the latex reaction mixture was raised to pH 9, and allowed to react with 18 mg of avidin in 30 ml of borate buffer (0.02M, pH 9) at 4° C. for another 5 hours. BSA (88 mg) was added, and stirring was continued at 4° C. overnight after which the latex-avidin mixture was dialyzed against 0.02M Tris containing 0.2% Tween-20 at pH 9. After dialysis, the latex-avidin was purified on a Sepharose CL-6B column using Tris-Tween buffer as the eluent. A yield of 47 ml was attained. After addition of BSA (0.2% final concentration) the resulting material was heat stressed at 45° C. for 3 days before coupling to the THC-biotin bidentate.

A suspension of 10 ml of the latex-avidin material was adjusted to pH 7. A small volume of 5 mM HABA in phosphate buffer was then added to the suspension. The HABA bound to the avidin, and turned the color of the mixture slightly pinkish. A solution containing 5.8 mg/ml of the THC-biotin bidentate in methanol was then added dropwise to the latex-avidin solution until the pink color disappeared, indicating the that the THC-biotin bidentate had completely displaced the HABA from the latex-avidin. A total of 0.17 mg of THC-biotin was added.

The reaction mixture was let stand for 1 hour at room temperature, and then eluted with 0.02M Tris containing 0.2% Tween-20 at pH 9 on a sepharose CL-6B column. The yield of latex-avidin-biotin-THC conjugate was 12 ml.

The above-described latex-avidin-biotin-THC conjugate as used in a homogeneous immunoassay for THC and its metabolites. The assay protocol used a Beckman ICS Analyzer II under the following conditions:

ICS Buffer: 60 µl

Antibody: 42 µl

Calibrator $\Delta^9$-THC-COOH in urine 42 µl (neat)

Latex-Avidin-Biotin-THC

Conjugate (Trigger Reagent) 42 µl (neat)

(Conjugate in 0.02M Tris buffer, 0.2% Tween, pH 9)

Gain: 2

RatX: 10

The results of the assay are presented in Table 24.

TABLE 24

| Urine Standards (ng/ml) | Rate Unit | % B/B$_0$ |
|---|---|---|
| 0 | 1415 | 100 |
| 50 | 1030 | 72.8 |
| 100 | 934 | 66.0 |

The results thus indicated that $\Delta^9$-THC-carboxylic acid, a major metabolite of THC in urine could be detected at extremely low concentrations by nephelometric inhibition immunoassay using the Latex-Avidin-Biotin-THC conjugate in accordance with the methods of the present invention.

EXAMPLE 16

LATEX PARTICLE-ENHANCED HOMOGENEOUS IMMUNOASSAY FOR PCP

Phencyclidine, also known as "PCP," is a drug of abuse used solely for its potent hallucinogenic effects. A novel biotinylated PCP derivative was synthesized and used in accordance with the methods of the present invention to define a homogeneous immunoassay for phencyclidine.

Figure 11:
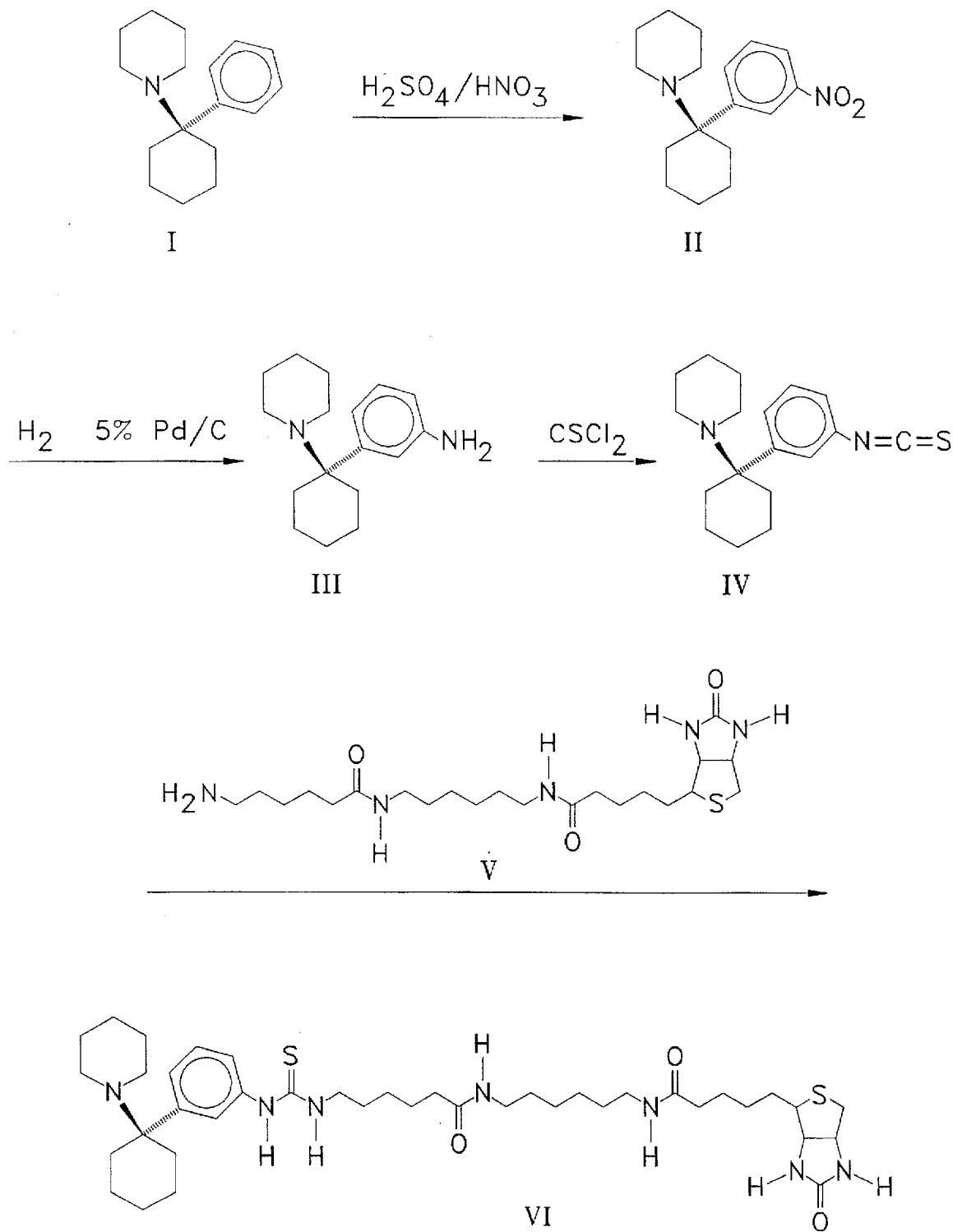
FIG. 11 shows the synthetic scheme used to synthesize a phencyclidine-biotin bidentate.

The synthetic scheme used to produce the PCP derivative is shown in FIG. 11. With reference to FIG. 11, PCP (I) was nitrated with $H_2SO_4/HNO_3$ to give a nitrated PCP derivative (II). The nitrated PCP derivative (II) was hydrogenated with 5% Pd/C as catalyst to yield an amino PCP derivative (III). The amino PCP derivative (III) was reacted with phosgene to form a PCP isothiocyanate (IV). The isothiocyanate derivative (IV) is then reacted with a biotin amine (V) to yield the desired PCP-biotin bidentate (V).

The capacity of the PCP-biotin bidentate (V) to be recognized by anti-PCP antibodies (i.e., the immunoreactivity of the bidentate) was assessed using an EMIT®) PCP kit. Samples of the PCP-biotin bidentate (VI) were prepared at 1000, 100 and 10 ng/ml by diluting the bidentate (VI) with EMIT® buffer. The PCP-biotin bidentate samples were then assayed as unknowns with the EMIT reagents on the Cobas Bio to determine the immunoreactivity of the PCP-biotin bidentate (VI). The results of this experiment are shown in Table 25, and indicate that the PCP-biotin bidentate was immunoreactive.

TABLE 25

| Actual PCP-Biotin Bidentate Concentration (ng/ml) | Concentration of PCP-Biotin Bidentate Observed by EMIT (ng/ml) | % Obs/Target |
|---|---|---|
| 1000 | >25 | — |
| 100 | ≈15 | ≈15% |
| 10 | ≈10 | ≈100% |

The PCP-biotin bidentate was used in a latex-enhanced immunoassay to detect PCP in urine. The latex-avidin conjugates used in such an immunoassay were obtained as follows. To 8.75 ml of MOPS buffer (0.1M) containing 0.55% Tween-20 were added a suspension of 1.25 ml of 60-nm size latex particles obtained from Seradyn, a solution of 82 mg of N-hydroxysuccinimide in 1.32 ml of cold MOPS, and a solution of 57.6 mg of water soluble carbodiimide in 1.26 ml of cold MOPS. After gentle stirring for 1 h at 4° C., the pH of the latex reaction mixture was raised to a pH of 9, and the mixture was allowed to react with 18 mg of avidin in 30 ml of borate buffer (0.02M, pH 9) at 4° C. for 5 h. Bovine serum albumin (BSA) (88 mg ) was added, and the mixture was stirred overnight at 4° C., thus yielding the desired latex-avidin particles. The latex-avidin mixture was then dialyzed against 0.02M TRIS containing 0.2% Tween-20 at pH 9. The latex-avidin particles were purified on a Sepharose CL-6B column using 0.02M TRIS containing 0.2% Tween-20 at pH 9 as the eluent.

The above-described PCP-biotin bidentate was permitted to bind to the latex-avidin particles in order to form a reagent that could be used to assay PCP in accordance with the 2-reagent system embodiment of the invention. Thus, to a suspension of 25 ml of the latex-avidin particles, adjusted to pH 7, was added in 10 µl increments, a solution containing 6.5 mg /ml of the PCP-biotin bidentate (VI) in methanol. The amount of the bidentate added was 0.52 mg (80 µl). The reaction mixture was gently mixed on a rocker for 1 hour after it was applied to a Sepharose CL-6B column. The latex-avidin-PCP-biotin conjugate was eluted from the column with 0.02M TRIS containing 0.2% Tween-20 at pH 9. The conjugate was scanned on the Beckman DU-70 spectrometer. Several of the observed spectral properties are shown in Table 26.

TABLE 26

| | Absorbance | | Absorbance |
|---|---|---|---|
| Sample | 500 nm | 600 nm | (500 nm/600 nm) |
| Tris Buffer (0.2% BSA) | 0.0686 | 0.0580 | 1.182 |
| Latex-Avidin (Replicate 1) | 0.4710 | 0.2471 | 1.905 |
| Latex-Avidin (Replicate 2) | 0.4713 | 0.2474 | 1.904 |

The latex-avidin-PCP-biotin conjugate and antibody reagents were optimized on the ARRAY 360 with the use of PCP solutions of defined concentration, prepared in urine. After optimization, the latex-enhanced bidentate methodology of the present invention was used with the ARRAY analyzer to screen the standards as well as several urine samples for PCP.

The assay buffers and reagents used in the ARRAY analyzer were:

a. PCP-biotin bidentate-avidin conjugate diluted in Tris buffer (0.02M, 0.2% BSA, pH 9.0)
b. Sheep anti-PCP antibody obtained from Biodesign, Inc. and diluted in the ARRAY Antibody Diluent
c. ICS buffer (employed as the assay buffer)
d. Calibrators (prepared in a urine pool donated from human volunteers)

In the ARRAY assay protocol employed:
RATX=10, gain=2.
Buffer: 500 μl
Antibody: 43.5 μl(1/1 20 dilution), trigger reagent
Sample 100 μl (1/6 on-line dilution)
Latex Conjugate: 42 μl (1/2 dilution)

The values obtained for the ARRAY dose-response curve are shown in Table 27.

TABLE 27

| Standard (ng/ml) | Rate Unit (N = 2) | % B/B0 |
|---|---|---|
| 0 | 1320 | 100 |
| 15 | 1070 | 81.1 |
| 25 | 882 | 66.8 |
| 50 | 603 | 45.7 |
| 75 | 394 | 29.8 |
| 100 | 250 | 18.9 |

The ARRAY results were compared to those obtained by the Gas Chromatography/Mass Spectroscopy ("GC/MS") method. The results of this comparison are shown in Table 28. As indicated in Table 28, a correlation was observed between the GC/MS confirmatory test and the ARRAY assay. Based on a cut-off concentration of 30 ng/ml, the ARRAY PCP screening method correctly predicted all positive samples (n=13) and all negative samples (n=17) confirmed by GC/MS for PCP. Thus the predictivities of the latex-bidentate method were 100% for both the PCP positive and PCP negative samples.

TABLE 28

|  | GC/MS (CUT-OFF = 25 ng/ml) | |
|---|---|---|
| N = 30 | + | − |
| ARRAY CUT-OFF + | 13 | 0 |
| 30 ng/ml − | 0 | 17 |

The same samples were run with the Syva EMIT® reagents on a Cobas Bios analyzer. The EMIT® reagents resulted in one false negative and no false positive, or predictivities of 91.7% for positive samples and 100% for negative samples. The results are shown in Table 29.

TABLE 29

|  | GC/MS (CUT-OFF = 25 ng/ml) | |
|---|---|---|
| N = 30 | + | − |
| EMIT ® CUT-OFF + | 12 | 0 |
| 25 ng/ml − | 1 | 17 |

Thus, a novel PCP-biotin bidentate (FIG. 11, VI) was prepared and used to define a highly sensitive latex-enhanced immunoassay for PCP. The PCP-biotin bidentate reagent may be used in any of a variety of immunoassay formats to define alternate or equivalent assays for PCP.

EXAMPLE 17

LATEX PARTICLE-ENHANCED HOMOGENEOUS IMMUNOASSAY FOR OPIATES

When heroin is ingested, some of the drug is metabolized to morphine and codeine. Thus, heroin, morphine and codeine might all be found in the urine of the heroin drug abuser. The methods of the present invention were used to produce a novel $O^3$-(biotinyl) morphine derivative. This novel morphine derivative was used to define a latex-enhanced homogeneous immunoassay that can be used to screen for the presence of opiates in blood or urine.

Figure 12:
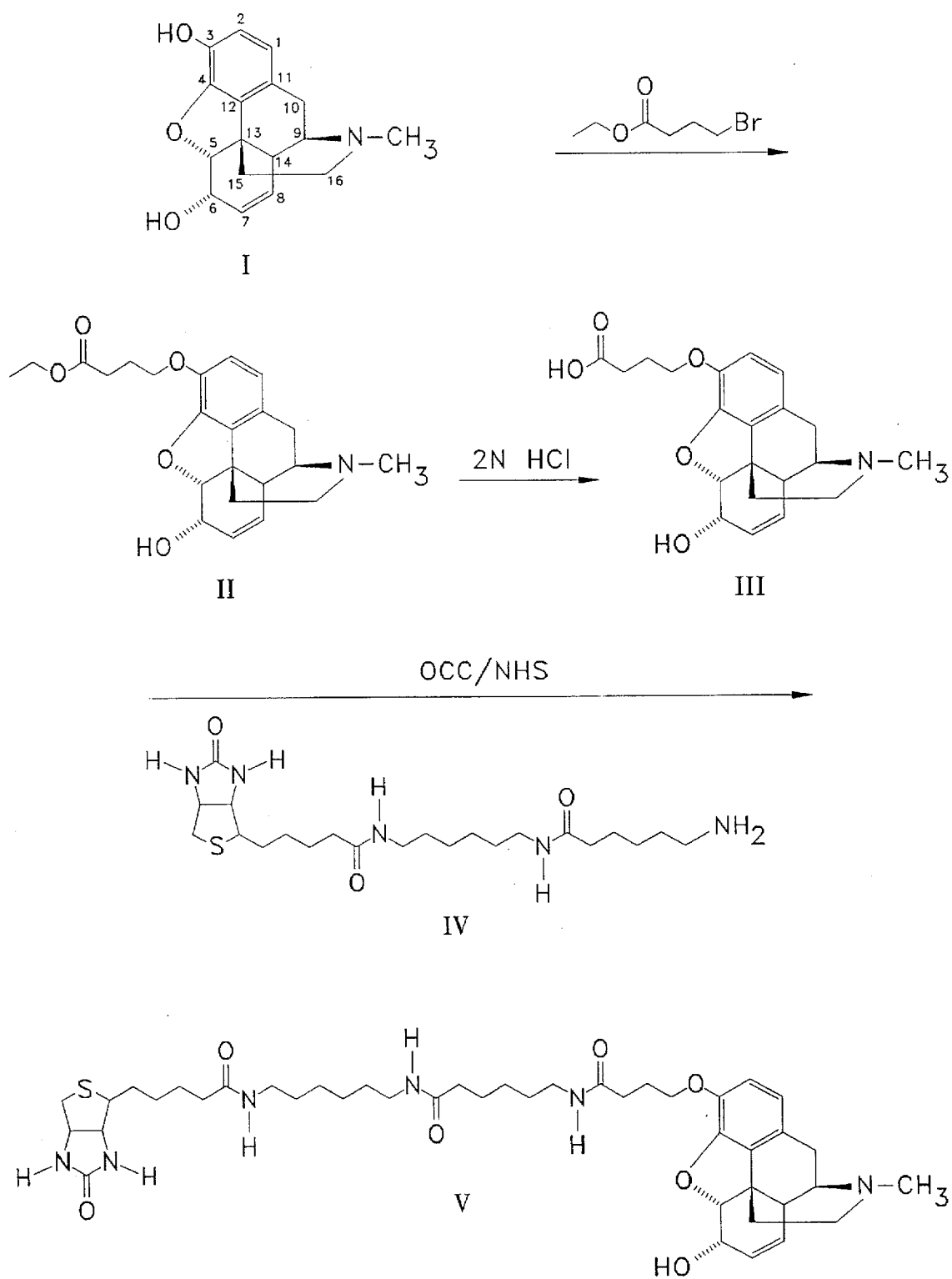
FIG. 12 shows the synthetic scheme used to synthesize a novel $O^3$-(biotinyl) morphine derivative.

The synthesis of the novel $O^3$-(biotinyl) morphine derivative is shown in FIG. 12. With reference to FIG. 12, morphine (I) was alkylated with ethyl 4-bromobutyrate resulting in the formation of an ester derivative (II). The ester was reacted with acid to yield an $O^3$-alkylated morphine carboxylic acid (III). The carboxylic acid (III) is then coupled to an aminobiotin (IV) to yield the desired morphine-biotin bidentate (V).

The immunoreactivity of the morphine-biotin bidentate (V) was assessed with an EMIT® opiate kit. Samples of the morphine-biotin bidentate (V) were prepared at 375, 37.5, 3.75 and 0.375 μg/ml by diluting the bidentate (V) with EMIT® buffer. The morphine-biotin bidentate samples were then assayed as unknowns with the EMIT reagents on a Cobas Bio analyzer to determine the immunoreactivity of the morphine-biotin bidentate (V). The result of this experiment is shown in Table 30, and indicate that the morphine-biotin bidentate was immunoreactive.

TABLE 30

| Actual PCP-Biotin Bidentate Concentration (μg/ml) | Concentration of PCP-Biotin Bidentate Observed by EMIT (μg/ml) | % Obs/Target |
|---|---|---|
| 375 | >1 | — |
| 37.5 | >1 | — |
| 3.75 | >1 | — |
| 0.375 | ≈0.1 | ≈27% |

The morphine-biotin bidentate was used in a latex-enhanced immunoassay to detect morphine in urine. The late-avidin conjugates used in such an immunoassay were obtained as follows. To 8.75 ml of MOPS buffer (0.1M) containing 0.55% Tween-20 were added a suspension of 1.25 ml of 60-nm size latex particles obtained from Seradyn, a solution of 82 mg of N-hydroxysuccinimide in 1.32 ml of cold MOPS, and a solution of 57.6 mg of water soluble carbodiimide in 1.26 ml of cold MOPS.

After gentle stirring for 1 h at 4° C., the pH of the latex reaction mixture was raised to a pH of 9, and the mixture was allowed to react with 18 mg of avidin in 30 ml of borate buffer (0.02M, pH 9) at 4° C. for 5 h. Bovine serum albumin (BSA) (88 mg ) was added, and the mixture was stirred overnight at 4° C., thus yielding the desired latex-avidin particles. The latex-avidin mixture was then dialyzed against 0.02M TRIS containing 0.2% Tween-20 at pH 9. The latex-avidin particles were purified on a Sepharose CL-6B column using 0.02M TRIS containing 0.2% Tween-20 at pH 9 as the eluent.

The above-described morphine-biotin bidentate was permitted to bind to the latex-avidin particles in order to form a reagent that could be used to assay morphine in accordance with the 2-reagent system embodiment of the invention. Thus, to a suspension of 25 ml of the latex-avidin particles, adjusted to pH 7, was added in 10 µl increments, a solution containing 7.6 mg /ml of the morphine-biotin bidentate (V) in methanol. The amount of the bidentate added was 0.76 mg (100 µl). The reaction mixture was gently mixed on a rocker for 1 hour after it was applied to a Sepharose CL-6B column. The latex-avidin-morphine-biotin conjugate was eluted from the column with 0.02M TRIS containing 0.2% Tween-20 at pH 9. The conjugate was scanned on the Beckman DU-70 spectrometer. Several of the observed spectral properties are shown in Table 31.

TABLE 31

| Sample | Absorbance 500 nm | Absorbance 600 nm | Absorbance (500 nm/600 nm) |
|---|---|---|---|
| Lot I | | | |
| Tris Buffer (0.2% BSA) | 0.0569 | 0.0543 | 1.047 |
| Latex-Avidin (Replicate 1) | 0.4983 | 0.2757 | 1.807 |
| Latex-Avidin (Replicate 2) | 0.4986 | 0.2759 | 1.807 |
| Lot II | | | |
| Tris Buffer (0.2% BSA) | 0.0544 | 0.0521 | 1.043 |
| Latex-Avidin (Replicate 1) | 0.5201 | 0.2779 | 1.872 |
| Latex-Avidin (Replicate 2) | 0.5203 | 0.2783 | 1.870 |

The latex-avidin-morphine-biotin conjugate and antibody reagents were optimized on the ARRAY 360 with the use of morphine solutions of defined concentration, prepared in urine. After optimization, the latex-enhanced bidentate methodology of the present invention was used with the ARRAY analyzer to screen the standards as well as several urine samples for morphine.

The assay buffers and reagents used in the ARRAY analyzer were:

a. morphine-biotin bidentate-avidin conjugate diluted in Tris buffer (0.02M, 0.2% BSA, pH 9.0)

b. Morphine antibody (obtained from Biostride and diluted in the ARRAY Antibody Diluent)

c. ICS buffer (employed as the assay buffer)

d. Calibrators (prepared in a urine matrix purchased from Utak)

In the ARRAY assay protocol employed:

RATX=10, gain=2.

Buffer: 614 µl

Antibody: 43.5 µl (1/120 dilution), trigger reagent

Sample 28 µl (1/18 on-line dilution) Latex Conjugate: 42 µl (1/2 dilution)

The values obtained for the ARRAY dose-response curve are shown in Table 32.

TABLE 32

| Standard (µg/ml) | Rate Unit (N = 2) | % B/BO |
|---|---|---|
| 0 | 1645 | 100 |
| 0.15 | 1355 | 82.4 |

TABLE 32-continued

| Standard (µg/ml) | Rate Unit (N = 2) | % B/BO |
|---|---|---|
| 0.3 | 1100 | 67.5 |
| 1 | 399 | 24.3 |

The ARRAY results were compared to those obtained by the Gas Chromatography/Mass Spectroscopy ("GC/MS") method. The results of this comparison are shown in Table 33. As indicated in Table 33, a good correlation was observed between the GC/MS confirmatory test and the ARRAY assay. Based on a cut-off concentration of 0.3 µg/ml, the ARRAY morphine screening method correctly predicted all positive samples (n=46) and 15 out of 16 negative samples confirmed by GC/MS for morphine.

Thus the predictivities of the latex-bidentate method for morphine positive and morphine negative samples were 100% and 93.3%, respectively

TABLE 33

| | | GC/MS (CUT-OFF = 0.3 µg/ml) | |
|---|---|---|---|
| N = 62 | | + | − |
| ARRAY CUT-OFF 0.3 µg/ml | + | 46 | 1 |
| | − | 0 | 15 |

The ARRAY results were, however, in complete agreement with those obtained with the Syva EMIT® reagents run on a Cobas Bio analyzer as indicated in Table 34.

TABLE 34

| | | EMIT® (CUT-OFF = 0.3 µg/ml) | |
|---|---|---|---|
| N = 62 | | + | − |
| ARRAY CUT-OFF 0.3 µg/ml | + | 46 | 0 |
| | − | 0 | 16 |

The morphine-biotin-avidin conjugate and antibody reagents were also optimized to detect morphine in urine samples using the Synchron. The assay buffers and reagents used in the Synchon were as follows:

a. Morphine-biotin bidentate-avidin conjugate diluted in Tris buffer (0.02M, 0.2% BSA, pH 9.0)

b. Morphine antibody (obtained from Biostride and diluted in the ARRAY Antibody Diluent)

c. ICS buffer (employed as the assay buffer)

d. Calibrators (prepared in an urine matrix purchased from Utak)

The assay was run under the following conditions:

Buffer: ICS buffer, 220 µl

Antibody: 30 µl (1/50 dilution), trigger reagent

Sample: 5 µl (neat)

Latex Conjugate: 60 µl (neat)

Read Window: 8 seconds after addition of trigger for 24 seconds

The values obtained for the ARRAY dose-response curve are shown in Table 35.

TABLE 35

| Standard (µg/m) | ΔAbs/Min (N = 2) | % B/BO |
| --- | --- | --- |
| 0 | 132 | 100 |
| 0.15 | 89 | 67.5 |
| 0.3 | 59 | 44.5 |
| 1 | 15 | 11.2 |

The same samples used in the ARRAY-GC/MS correlation described above were employed in the Synchron study. As indicated by the correlation results shown in Table 36, the latex-bidentate opiate assay on the Synchron exhibited 100% predictivities for both the GC/MS morphone positive (n=46) and negative samples (n=16).

TABLE 36

| N = 62 | GC/MS (CUT-OFF = 0.3 µg/ml) | |
| --- | --- | --- |
|  | + | − |
| SYNCHRON CUT-OFF 0.3 µg/ml + | 46 | 0 |
| SYNCHRON CUT-OFF 0.3 µg/ml − | 0 | 16 |

Thus, a novel morphine-biotin bidentate (FIG. 12, V) was prepared and used to define a highly sensitive latex-enhanced immunoassay for opiates. Similar to the Abbott and the Emit® assays, the above-described latex-based bidentate assay for opiates recognized not only morphine, but also other opiates such as codeine, hydrocodeine and hydromorphone in urine. The bidentate reagent may be used in any of a variety of immunoassay formats to define an assay for such opiates.

EXAMPLE 18

LATEX PARTICLE-ENHANCED HOMOGENEOUS IMMUNOASSAY FOR PHENYTOIN

Phenytoin is an anticonvulsant agent used in the treatment of epilepsy and other affective diseases (Philip, J. et al., In: Analytical Profiles of Drug Substances," vol. 13, Florey, K. et al. (eds.), Academic Press, NY (pp. 417–445 (1984); Dreifus et al., Amer. Heart J. 80:709–713 (1970), both herein incorporated by reference). Because phenytoin is a potential carcinogen (*IARC Monogr.* 13:201–225 (1977)), it is important to monitor patient phenytoin levels so as to avoid overdosage.

The methods of the present invention were used to produce a phenytoin-biotin bidentate. This novel bidentate was used to define a latex-enhanced homogeneous immunoassay that can be used to screen for the presence of opiates in blood or urine.

Figure 13:
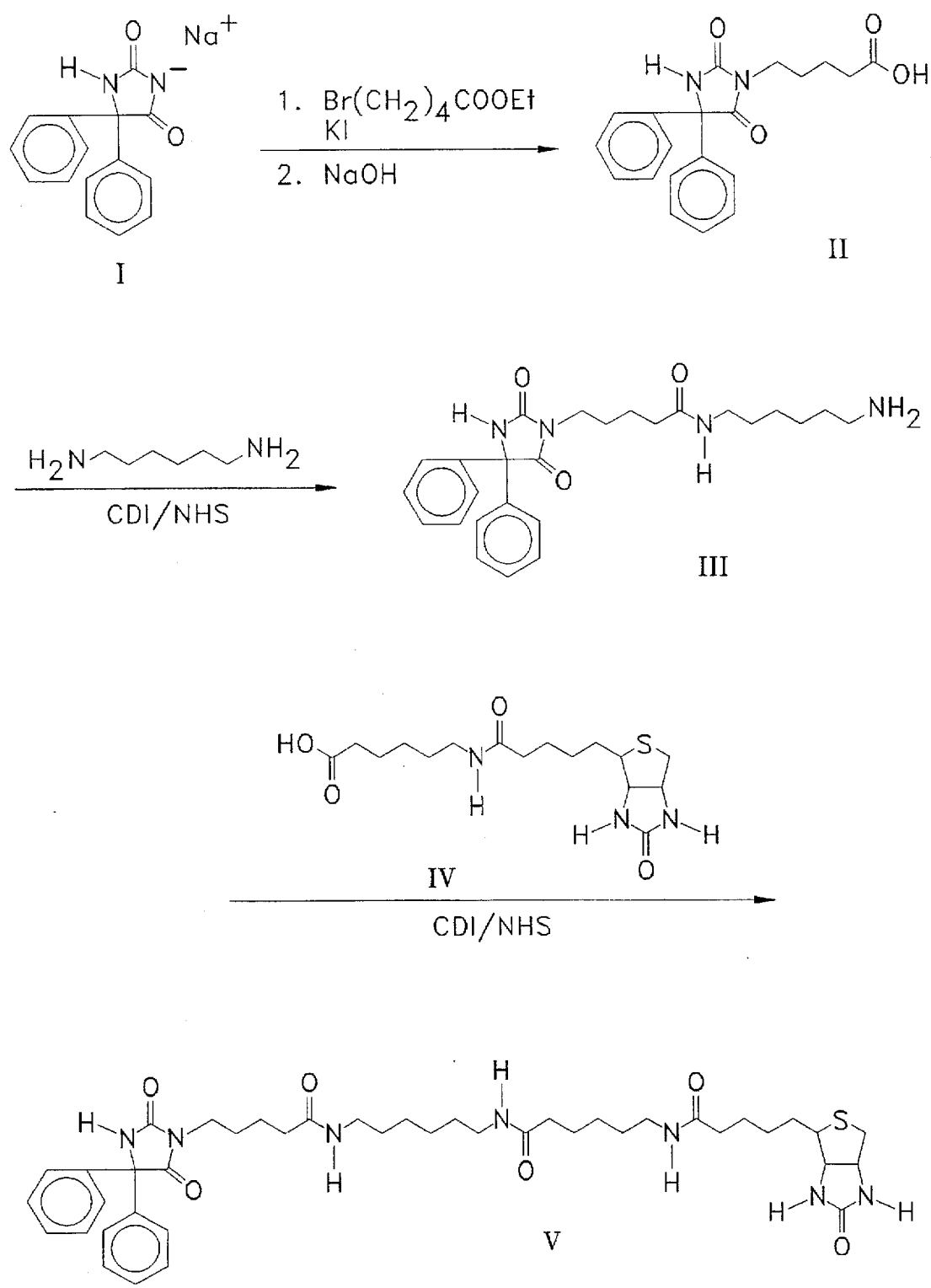
FIG. 13 shows the synthetic scheme used to synthesize a novel phenytoin-biotin bidentate.

The synthesis of the novel phenytoin-biotin bidentate is shown in FIG. 13. With reference to FIG. 13, phenytoin (I) was N-alkylated with (o bromovalerate followed by hydrolysis in NaOH to yield the phenytoin acid derivative (II). The phenytoin acid derivative (II) was then coupled with hexanediamine using carbonyidiimidazole (CDI) and N-hydroxysuccinimide (NHS) to give a phenytoin amine derivative (III). The phenytoin amine derivative (III) was then coupled to a carboxylic acid biotin derivative (IV) using CDI and NHS to yield the desired phenytoin-biotin bidentate (V).

The phenytoin-biotin bidentate was used to detect phenytoin in urine samples using both the above-described 3-reagent system configuration and the 2-reagent system configuration. In both assays, analysis was conducted using a Synchron analyzer.

Detection of phenytoin was accomplished using anti-phenytoin monoclonal antibodies produced from hybridoma clones AS3 or AS8. The antibodies produced from these clones are substantially equivalent. Suitable alternative monoclonal antibodies can be obtained commercially from BioSpecific, Inc. and BioDesign, Inc., or from other sources, such as those listed in the Linscott's Directory.

In the 3-reagent system configuration, the bidentate (V) itself was used as to trigger the immunoreaction (i.e., as the trigger reagent). The assay thus consisted of three reagent components:

a. phenytoin-biotin bidentate-avidin conjugate (diluted in Tris buffer (0.02M, 0.2% BSA, pH 9.0))

b. monoclonal anti-phenytoin antibody (produced by clone AS8) and diluted 1:50 with the ARRAY Antibody Diluent)

c. latex-avidin particles (diluted in Tris buffer (0.02M, 0.2% BSA, pH 9.0). The latex material (100 nm) was purchased from Seradyn. The latex particle was coupled to avidin to give the latex-avidin material using a mass ratio of 0.3 mg of avidin to 1 mg of latex.

The assay buffer was a mixture of 80% Apo Diluent (Beckman Instruments) and 20% Rhematoid Buffer (Beckman Instruments). Calibrators were prepared in delipidized human serum. The Synchron analyzer was configured in the following manner for the 3-reagent assay:

a. Assay Buffer in Reagent Cartridge Compartment A: 220 µl b. Antibody (1/50)/Latex Avidin Mixture (1:1 by vol) in Compartment B: 62 µl c. Sample: 3 µl (neat)

d. Phenytoin-Biotin Bidentate (1.5 µg/mL) as trigger in Compartment C: 20 µl e. Trigger Add Time: 16 sec after addition of sample f. Reaction Read Window: 8 seconds after addition of trigger for 36 seconds g. Detection wavelength: 340 nm The assay was conducted using several standards in order to define a standard curve. The values of the standard curve are shown in Table 37.

TABLE 37

| Standard (µg/ml) | ΔAbs/Min | % B/BO |
| --- | --- | --- |
| 0 | 0.26097 | 100 |
| 2.5 | 0.19798 | 75.9 |
| 5.0 | 0.13645 | 52.3 |
| 10 | 0.06723 | 25.8 |
| 20 | 0.02986 | 11.4 |
| 40 | 0.01622 | 6.2 |

The above-described 3-reagent assay was conducted in parallel with a TDx assay on a group of 38 patients. A good correlation was found between the 3-reagent Synchron values and those obtained using the TDx format. The analysis gave the following correlation equation:

Synchron=1.0000(TDx)+0.07 r=0.9470 n=38

As indicated, the Synchron immunoassay was also performed using the above-described 2-reagent configuration. The 2-reagent assay configuration consisted of the latex-avidin-biotin-phenytoin conjugate and the antibody to produce the latex-agglutination reaction. Thus, in the 2-reagent assay format, the phenytoin-biotin bidentate was formulated as a conjugate component. The assay used the following reagents and buffers:

a. Monoclonal phenytoin antibody AS8 produced by Beckman Instruments was used. The antibody was diluted 1:50 with the ARRAY Antibody Diluent (Beckman P/N 668579) for assays.

b. Latex-Avidin-Biotin-Phenytoin conjugate (diluted in Tris buffer (0.02M, 0.2% BSA, pH 9.0). The latex material (100 nm) was purchased from Seradyn. The latex particle was coupled to avidin using a mass ratio of 0.3 mg of avidin to 1 mg of latex. The latex-advin was then complexed with the phenytoin bidentate to give the desired conjugate.

The assay buffer was a mixture of 70% Apo Diluent (Beckman Instruments) and 30% Rhematoid Buffer (Beckman Instruments). Calibrators were prepared in delipidized human serum. The Synchron analyzer was configured in the following manner for the 2-reagent assay:

a. Assay Buffer in Reagent Cartridge Compartment A: 220 μl b. Latex-Avidin-Phenytoin-Biotin Conjugate in Compartment C: 62 μl c. Sample: 3 μl (neat)

d. Antibody trigger in Compartment B: 30 μl e. Trigger Add Time: 16 sec after addition of sample f. Reaction Read Window: 8 seconds after addition of trigger for 36 seconds g. Detection wavelength: 340 nm The assay was thus conducted using several standards in order to define a standard curve. The values of the standard curve are shown in Table 38.

TABLE 38

| Standard (μg/mL) | ΔAbs/Min | % B/BO |
|---|---|---|
| 0 | 0.30155 | 100 |
| 2.5 | 0.25640 | 85.0 |
| 5.0 | 0.18894 | 62.7 |
| 10 | 0.14687 | 48.7 |
| 20 | 0.09664 | 32.0 |
| 40 | 0.05111 | 16.9 |

The above-described 2-reagent assay was conducted in parallel with a TDx assay on a group of 62 patients. A good correlation was found between the 2-reagent Synchron values and those obtained using the TDx format. The analysis gave the following correlation equation:

Synchron=1.10292(TDx)−0.12 r=0.9798 n=62

A comparison was conducted in order to determine the affect of latex-avidin particles on assay sensitivity or assay requirements. Thus, the 2-reagent Synchron assay for phenytoin was conducted with and without the above-described latex-avidin particles. Both assays used the same anti-phenytoin monoclonal antibody (produced by hybridoma clone AS3). The assays were conducted under the optimized conditions shown in Table 39.

TABLE 39

| | Formulation | |
|---|---|---|
| Reagent/Parameter | Liquid | Latex-Enhanced |
| Assay Buffer (ICS Buffer:ICS Diluent) | 60%:40% | 80%:20% |
| Assay Buffer Volume | 235 μl | 230 μl |
| Avidin-biotin-phenytoin conjugate (in citrated buffer saline) | 32 μl | 42 μl |
| clone AS3 Antibody Dilution | 1/3.25 | 1/100 |
| Antibody Volume | 45 μl | 30 μl |
| Sample volume | 3 μl | 3 μl |
| Trigger | Antibody | Antibody |
| Trigger Add Time | 16 seconds after addition of sample | |
| Reaction Read Window | 8 seconds after addition of trigger for 32 seconds | |
| Detection wavelength | 340 nm | 340 nm |

The assay conducted without latex particles (i.e., the "liquid-formulated phenytoin bidentate assay") was found to have required an antibody dilution of 1/3.25. In contrast, when the avidin was coupled to latex particles (i.e., in the "latex-enhanced" immunoassay formulation), an antibody dilution of 1/100 could be employed. Thus, the liquid formulated assay required at least thirty times more antibody than was required in the "latex-enhanced" immunoassay formulation. Moreover, the liquid formulation resulted in a much less sensitive dose-response as compared to the latex formulation.

The assays were evaluated using a set of phenytoin standard solutions in order to define standard curves for the liquid-formulated and the latex-enhanced assay. The standard curves are presented in Table 40 (Abs=absorbance; Min=minutes).

TABLE 40

| Standard | Liquid-Formulation | | Latex-Enhanced | |
|---|---|---|---|---|
| (μg/ml) | ΔAbs/Min | % B/$B_0$ | ΔAbs/Min | % B/$B_0$ |
| 0 | 0.31183 | 100 | 0.45152 | 100 |
| 2.5 | 0.28274 | 90.1 | 0.18168 | 45.2 |
| 5.0 | 0.25311 | 81.1 | 0.09175 | 22.8 |
| 10 | 0.20903 | 67.0 | 0.04749 | 11.9 |
| 20 | 0.12627 | 40.5 | 0.01911 | 4.7 |
| 40 | 0.039901 | 12.8 | 0.01091 | 2.7 |

The results of the liquid formulation and latex-enhanced assays indicated that either assay could be used to accurately determine phenytoin concentrations.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. An assay for determining the presence of a target analyte in a test sample comprising the steps of:
   (A) forming a reaction mixture by contacting a test sample with:
      (i) a bidentate reagent comprising a biotin member, an analyte member, and a spacer member between said biotin and analyte members, wherein:
         (a) said biotin member of said reagent is bound to a biotin-binding agent selected from the group consisting of avidin and streptavidin; said biotin-binding agent being covalently bound to a solid support, said solid support being a latex particle having a particle size of about 38 to 100 nanometers;
         (b) said analyte member of said reagent is capable of specifically binding to an antibody capable of binding to a target analyte;
         (c) said intermediate spacer member is sufficient in length to permit said analyte member to bind to the antibody and said biotin member to bind to the biotin-binding agent; and
      (ii) said antibody;
   (B) incubating said reaction mixture under conditions sufficient to permit the formation of a complex between said bidentate reagent and said antibody; and
   (C) measuring the extent of any formation of said complex using nephelometric or turbidimetric means, said extent being inversely proportional to the concentration of said target analyte in said sample.

2. The assay of claim 1, wherein said spacer member of said bidendate reagent comprises an adduct of a reagent selected from the group consisting of an alkyldiamine, an alkyl anhydride, and an alkylamino acid.

3. The assay of claim 2, wherein said reagent is an alkyldiamine.

4. The assay of claim 3, wherein said alkyldiamine is a pentane diamine, a hexane diamine or an octane diamine.

5. The assay of claim 2, wherein said spacer member has an extended length of about 20 atoms.

6. The assay of claim 1, wherein said spacer member and said biotin member comprise caproamidobiotin.

7. The assay of claim 1, wherein said antibody is capable of binding an analyte selected from the group consisting of benzoylecgonine, cocaine, an opiate and PCP.

8. The assay of claim 1, wherein said target analyte is digoxin.

9. The assay of claim 1, wherein said target analyte is acetaminophen.

10. The assay of claim 1, wherein said target analyte is carbamazepine.

11. The assay of claim 1, wherein said target analyte is selected from the group consisting of primidone and phenytoin.

12. The assay of claim 1, wherein said target analyte is theophylline.

13. The assay of claim 1, wherein said target analyte is an aminoglycoside antibiotic.

14. The assay of claim 13, wherein said aminoglycoside antibiotic is selected from the group consisting of tobramycin, gentamycin and amikacin.

15. The assay of claim 1, wherein said target analyte is vancomycin.

16. The assay of claim 1, wherein said target analyte is quinidine.

17. The assay of claim 1, wherein said target analyte is a cannabinoid.

18. The assay of claim 17, wherein said cannabinoid is tetrahydrocannabinol.

19. The assay of claim 1, wherein said biotin-binding agent is streptavidin.

20. The assay of claim 1, wherein said biotin-binding agent is avidin.

21. The assay of claim 1, wherein said latex is carboxylate modified latex.

22. The assay of claim 1, wherein said latex particle is heat stressed.

23. The assay of claim 1, wherein said biotin-binding agent is avidin, and wherein said avidin is covalently bound to said latex particle by incubating said latex particle and avidin in the presence of N-hydroxysuccinimide and 1-ethyl-3-(3-dimethylaminopropyl) carbodiimide under conditions sufficient to achieve such binding.

24. The assay of claim 1, wherein said target analyte is procainamide.

25. The assay of claim 1, wherein said latex particle has a diameter of about 60 to 100 nanometers.

* * * * *